United States Patent
Goldberg et al.

(10) Patent No.: US 12,098,210 B2
(45) Date of Patent: Sep. 24, 2024

(54) METHODS OF TREATING CANCERS AND ENHANCING EFFICACY OF BCMAxCD3 BISPECIFIC ANTIBODIES

(71) Applicant: JANSSEN BIOTECH, INC., Horsham, PA (US)

(72) Inventors: Jenna Goldberg, Raritan, NJ (US); Jagoda Jasielec, Spring House, PA (US); Raluca Verona, Spring House, PA (US); Brendan Weiss, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 18/052,174

(22) Filed: Nov. 2, 2022

(65) Prior Publication Data
US 2023/0272102 A1    Aug. 31, 2023

Related U.S. Application Data

(60) Provisional application No. 63/348,036, filed on Jun. 2, 2022, provisional application No. 63/288,279, filed (Continued)

(51) Int. Cl.
*C07K 16/28* (2006.01)
*A61K 31/454* (2006.01)
(Continued)

(52) U.S. Cl.
CPC ........ *C07K 16/2878* (2013.01); *A61K 31/454* (2013.01); *A61K 31/573* (2013.01);
(Continued)

(58) Field of Classification Search
None
See application file for complete search history.

(56) References Cited

U.S. PATENT DOCUMENTS 5,223,409 A    6/1993 Ladner et al.
5,403,484 A    4/1995 Ladner et al.
(Continued)

FOREIGN PATENT DOCUMENTS

EP    0999853 B1    1/2003
EP    2762497 A1    8/2014
(Continued)

OTHER PUBLICATIONS

Krishnan et al. Updated phase 1 results of teclistamab, a B-cell maturation antigen (BCMA)xCD3 bispecific antibody, in relapsed/refractory multiple myeloma (MM). Journ. of Clin. Oncology. vol. 39 No. 15 (Year: 2021).*

(Continued)

*Primary Examiner* — Daniel E Kolker
*Assistant Examiner* — Hilary Ann Petrash
(74) *Attorney, Agent, or Firm* — TROUTMAN PEPPER HAMILTON SANDERS LLP

(57) ABSTRACT

Disclosed are methods of treating cancers and enhancing efficacy of BCMAxCD3 bispecific antibodies. In particular, methods are disclosed of using a BCMAxCD3 bispecific antibody, an anti-CD38 antibody and/or pomalidomide to treat cancers, particularly relapsed or refractory multiple myeloma.

10 Claims, 7 Drawing Sheets
Specification includes a Sequence Listing.

Related U.S. Application Data on Dec. 10, 2021, provisional application No. 63/275,368, filed on Nov. 3, 2021.

(51) Int. Cl.
*A61K 31/573* (2006.01)
*A61K 39/00* (2006.01)
*A61K 39/395* (2006.01)
*A61P 35/00* (2006.01)
*C07K 16/30* (2006.01)

(52) U.S. Cl.
CPC .... *A61K 39/3955* (2013.01); *A61K 39/39558* (2013.01); *A61P 35/00* (2018.01); *C07K 16/2809* (2013.01); *C07K 16/2896* (2013.01); *C07K 16/30* (2013.01); *A61K 2039/507* (2013.01); *A61K 2039/545* (2013.01); *C07K 2317/31* (2013.01)

(56) References Cited

U.S. PATENT DOCUMENTS

| | | |
|---|---|---|
| 5,427,908 A | 6/1995 | Dower et al. |
| 5,571,698 A | 11/1996 | Ladner et al. |
| 5,580,717 A | 12/1996 | Dower et al. |
| 5,885,793 A | 3/1999 | Griffiths et al. |
| 5,932,448 A | 8/1999 | Tso et al. |
| 5,969,108 A | 10/1999 | McCafferty et al. |
| 6,172,197 B1 | 1/2001 | McCafferty et al. |
| 6,521,404 B1 | 2/2003 | Griffiths et al. |
| 6,521,427 B1 | 2/2003 | Evans |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,670,127 B2 | 12/2003 | Evans |
| 6,737,056 B1 | 5/2004 | Presta |
| 6,833,441 B2 | 12/2004 | Wang et al. |
| 7,829,673 B2 | 11/2010 | De Weers et al. |
| 7,994,289 B2 | 8/2011 | Waldmann et al. |
| 8,088,896 B2 | 1/2012 | Tesar et al. |
| 8,153,765 B2 | 4/2012 | Park et al. |
| 8,236,308 B2 | 8/2012 | Kischel et al. |
| 9,150,663 B2 | 10/2015 | Labrijn et al. |
| 10,072,088 B2 | 9/2018 | Pillarisetti et al. |
| 2005/0276803 A1 | 12/2005 | Chan et al. |
| 2007/0287170 A1 | 12/2007 | Davis et al. |
| 2009/0182127 A1 | 7/2009 | Kjaergaard et al. |
| 2010/0015133 A1 | 1/2010 | Igawa et al. |
| 2010/0028637 A1 | 2/2010 | Tavsanli et al. |
| 2011/0123532 A1 | 5/2011 | Gurney et al. |
| 2012/0149876 A1 | 6/2012 | Von Kreudenstein et al. |
| 2013/0156769 A1 | 6/2013 | Kufer et al. |
| 2013/0195849 A1 | 8/2013 | Spreter Von Kreudenstein et al. |
| 2014/0154254 A1 | 6/2014 | Kannan et al. |
| 2014/0303356 A1 | 10/2014 | Gramer et al. |
| 2016/0297885 A1 | 10/2016 | Kuo et al. |
| 2018/0118849 A1 | 5/2018 | Klein et al. |
| 2019/0263920 A1 | 8/2019 | Vu et al. |
| 2019/0352421 A1* | 11/2019 | Adams ............... C07K 16/2896 |
| 2019/0367628 A1 | 12/2019 | Abujoub et al. |
| 2020/0179511 A1 | 6/2020 | Daley et al. |
| 2020/0190205 A1 | 6/2020 | Adams et al. |
| 2020/0308284 A1* | 10/2020 | Bandekar ................ A61P 35/00 |
| 2021/0128619 A1 | 5/2021 | Campbell et al. |
| 2022/0041742 A1* | 2/2022 | Adams .................... A61P 35/02 |
| 2022/0373550 A1 | 11/2022 | Pillarisetti et al. |
| 2022/0411525 A1 | 12/2022 | Adams, III et al. |
| 2023/0279136 A1 | 9/2023 | Muzammil et al. |

FOREIGN PATENT DOCUMENTS

| | | |
|---|---|---|
| WO | 1988001649 A1 | 3/1988 |
| WO | 1992001047 A1 | 1/1992 |
| WO | 1994013804 A1 | 6/1994 |
| WO | 1996027011 A1 | 9/1996 |
| WO | 1998044001 A1 | 10/1998 |
| WO | 2000041474 A2 | 7/2000 |
| WO | 2001024811 A1 | 4/2001 |
| WO | 2001024812 A1 | 4/2001 |
| WO | 2002066516 A2 | 8/2002 |
| WO | 2004078140 A2 | 9/2004 |
| WO | 2006028936 A2 | 3/2006 |
| WO | 2007059782 A1 | 5/2007 |
| WO | 2007117600 A2 | 10/2007 |
| WO | 2007147901 A1 | 12/2007 |
| WO | 2008119565 A2 | 10/2008 |
| WO | 2008119566 A2 | 10/2008 |
| WO | 2008119567 A2 | 10/2008 |
| WO | 2009085462 A1 | 7/2009 |
| WO | 2009132058 A2 | 10/2009 |
| WO | 2009134776 A2 | 11/2009 |
| WO | 2010037836 A2 | 4/2010 |
| WO | 2010037837 A2 | 4/2010 |
| WO | 2010037838 A2 | 4/2010 |
| WO | 2010051274 A2 | 5/2010 |
| WO | 2010093627 A2 | 8/2010 |
| WO | 2010104949 A2 | 9/2010 |
| WO | 2011131746 A2 | 10/2011 |
| WO | 2011143545 A1 | 11/2011 |
| WO | 2012022811 A1 | 2/2012 |
| WO | 2012066058 A1 | 5/2012 |
| WO | 2012143498 A1 | 10/2012 |
| WO | 2012158818 A2 | 11/2012 |
| WO | 2012163805 A1 | 12/2012 |
| WO | 2013020074 A2 | 2/2013 |
| WO | 2013072406 A1 | 5/2013 |
| WO | 2013072415 A1 | 5/2013 |
| WO | 2013096291 A2 | 6/2013 |
| WO | 2013157954 A1 | 10/2013 |
| WO | 2013158856 A2 | 10/2013 |
| WO | 2014056783 A1 | 4/2014 |
| WO | 2014089335 A2 | 6/2014 |
| WO | 2014093908 A2 | 6/2014 |
| WO | 2014122143 A1 | 8/2014 |
| WO | 2014122144 A1 | 8/2014 |
| WO | 2014124143 A1 | 8/2014 |
| WO | 2014140248 A1 | 9/2014 |
| WO | 2014145806 A2 | 9/2014 |
| WO | 2015052536 A1 | 4/2015 |
| WO | 2016166629 A1 | 10/2016 |
| WO | 2018083204 A1 | 5/2018 |
| WO | 2019220368 A1 | 11/2019 |
| WO | 2020089794 A1 | 5/2020 |
| WO | WO-2020261093 A1 * | 12/2020 ........... A61K 31/167 |
| WO | 2021092060 A1 | 5/2021 |
| WO | 2021113701 A1 | 6/2021 |

OTHER PUBLICATIONS

Shah et al. Daratumumab versus lenalidomide maintenance therapy for MM: a randomized pilot study comparing patient reported health related quality of life measures. Blood. 2021. 138 (Supplement 1): 4762 (Year: 2021).*

Chen et al., "A Modeling Framework to Characterize Cytokine Release upon T-Cell-Engaging Bispecific Antibody Treatment: Methodology and Opportunities," Clin. Transl. Sci. (Nov. 2019) vol. 12(6), pp. 600-608.

Saber et al., "An FDA Oncology Analysis of CD3 Bispecific Constructs and First-In-Human Dose Selection," Regulatory Toxicology and Pharmacology (Nov. 2017) vol. 90, pp. 144-152.

Lefranc et al., "IMGT Unique Numbering for Immunoglobulin and T Cell Receptor Variable Domains and Ig Superfamily V-Like Domains," Dev. Comp. Immunol. (2003) vol. 27, pp. 55-77.

Li, et al., "Effect of PS-341 on Multiple Myeloma Cells Migrationd Secretion BAFF and April," Aerosoace Medicine, 21(6):885-888, (Jun. 2010).

Liu et al., "Ligand-Receptor Binding Revealed by the TNF Family Member TALL-1," Nature, 423:49-56, (May 1, 2003).

Madry et al., "The Characterization of Murine BCMA Gene Defines it as a New Member of the Tumor Necrosis Factor Receptor Superfamily," Int Immunol (1998) vol. 10, No. 11, pp. 1693-1702.

(56) References Cited

OTHER PUBLICATIONS

Marks et al., "By-Passing Immunization," J. Mol. Biol. (1991) vol. 222, p. 581-597.
Marriuzza et al., "The Structural Basis of Antigen-Antibody Recognition," Ann. Rev. Biophys. Chem. (1987) vol. 16, pp. 139-159.
Martin et al., "Structural Families in Loops of Homologous Proteins: Automatic Classification, Modelling and Application to Antibodies," J. Mol. Biol., (1996) vol. 263, pp. 800-815.
Mori et al., "Engineering Chinese Hamster Ovary Cells to Maximize Effector Function of Produced Antibodies Using FUT8 siRNA," Biotechnology and Bioengineering (Dec. 30, 2004) vol. 88, No. 7, pp. 901-908.
Myers et al., "Optimal Alignments in Linear Space," Cabios (1988) vol. 4, No. 1, pp. 11-17.
Needleman et al., "A General Method Applicable to the Search for Similarities in the Amino Acid Sequence of Two Proteins," J. Mol. Biol. (1970) vol. 48, pp. 443-453.
Novak et al., "Expression of BCMA, TACI, and BAFF-R in Multiple Myeloma: A Mechanism for Growth and Survival," Blood (Jan. 15, 2004) vol. 103(2). pp. 689-694.
Nunez-Prado et al., "The Coming of Age of Engineered Multivalent Antibodies," Drug Discovery Today (2015) vol. 20, No. 5, pp. 588-594.
Okayama et al., "A cDNA Cloning Vector that Permits Expression of cDNA Inserts in Mammalian Cells," Molecular and Cellular Biology (Feb. 1983) vol. 3, No. 2, pp. 280-289.
Olivier et al., "EB66 Cell Line, a Duck Embryonic Stem Cell-Derived Substrate for the Industrial Production of Therapeutic Monoclonal Antibodies with Enhanced ADCC Activity," mAbs (2010) vol. 2, No. 4, pp. 405-415.
Osborn et al., "High-Affinity IgG Antibodies Develop Naturally in Ig-Knockout Rats Carrying Germline Human IgH/Igk/Ig? Loci Bearing the Rat CH Region," The Journal of Immunology (2013) vol. 190, pp. 1481-1490.
Otwinowski et al., "[20] Processing of X-Ray Diffraction Data Collected in Oscillation Mode," Methods in Enzymology (1997) vol. 276, pp. 307-326.
Padlan et al., Structure of an antibody-antigen complex: crystal structure of the HyHEL-1 O Fab-lysozyme complex, PNAS 86:5938-594, 1989.
Pascalis et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunology (2002) vol. 169, pp. 3076-3084.
Pillarisetti et al., "Teclistamab is an Active T Cell-Redirecting Bispecific Antibody Against B-Cell Maturation Antigen for Multiple Myeloma," Blood Advances (Sep. 22, 2020) vol. 4, No. 18, pp. 4538-4549.
Read, "Pushing the Boundaries of Molecular Replacement with Maximum Likelihood," Acta Cryst. (2001) D57, pp. 1373-1382.
Revets et al., "Nanobodies as Novel Agents for Cancer Therapy," Expert Opin. Biol. Ther. (2005) vol. 5, No. 1, pp. 111-124.
Rickert et al., "Signaling by the TNFR Superfamily in B-Cell Biology and Disease," Immunol. Rev., 244(1): 115-133, Nov. 2011.
Salmeron et al., "A Conformational Epitope Expressed upon Association of CD3-Epsilon with Either CD3-delta or CD3-gamma is the Main Target for Recognition by Anti-CD3 Monoclonal Antibodies," The Journal of Immunology (1991) vol. 147, No. 9, pp. 3047-3052.
Sanchez et al., "Serum B-Cell Maturation Antigen is Elevated in Multiple Myeloma and Correlates with Disease Status and Survival," British Journal of Hematology (Jul. 18, 2012) vol. 158, No. 158, pp. 727-738.
Sheets et al., "Efficient Construction of a Large Nonimmune Phage Antibody Library: The Production of High-Affinity Human Single-Chain Antibodies to Protein Antigens," Proc. Natl. Acad. Sci. USA (May 1998) vol. 95, pp. 6157-6162.
Shi et al., "De Novo Selection of High-Affinity Antibodies from Synthetic Fab Libraries Displayed on Phage as pIX Fusion Proteins," J. Mol. Biol. (2010) vol. 397, pp. 385-396.
Shields et al., "Lack of Fucose on Human IgG1 N-Linked Oligosaccharide Improves Binding to Human FcγRIII and Antibody-Dependent Cellular Toxicity," The Journal of Biological Chemistry (2002) vol. 227, No. 30, pp. 26733-26740.
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry (2002) vol. 278, No. 5, pp. 3466-3473.
Stickler et al., "The Human G1m1 Allotype Associates with CD4+ T-Cell Responsiveness to a Highly Conserved IgG1 Constant Region Peptide and Confers an Asparaginyl Endopeptidase Cleavage Site," Genes and Immunity (2011) vol. 12, pp. 213-221.
Tai et al., "Targeting B-Cell Maturation Antigen in Multiple Myeloma," Immunotherapy (Nov. 2015) vol. 7(11), pp. 1187-1199.
Terhorst et al., "Biochemical Studies of the Human Thymocyte Cell-Surface Antigens T6, T9 and T10," Cell (Mar. 1981) vol. 23, No. 3, pp. 771-780.
Topp et al., "8007: Evaluation of AMG 420, an Anti-BCMA Bispecific T-Cell Engager (BiTE) Immunotherapy, in R/R Multiple Myeloma (MM) Patients: Updates Results of a First-in-Human (FIH) Phase I Dose Escalation Study," Journal of Clinical Oncology (May 20, 2019) vol. 37, Suppl. 15, p. 8007.
Usmani et al., "Phase 1 Study of Teclistamab, a Humanized B-Cell Maturation Antigen (BCMA) x CD3 Bispecific Antibody, in Relapsed or Refractory Multiple Myeloma," Presented at the 56th ASCO Annual Meeting, 2020, Abstract 100.
Usmani et al., "Phase I Study of Teclistamab, A Humanized B-Cell Maturation Antigen (BCMA) x CD3 Bispecific Antibody, in Relapsed/Refractory Multiple Myeloma (R/R MM)," 2020 ASCO Annual Meeting I, Meeting Abstract, Journal of Clinical Oncology, vol. 38, No. 15, Suppl 100.
Usmani et al., "Teclistamab, a B-Cell Maturation AntigenxCD3 Bispecific Antibody, in Patients with Relapsed or Refractory Multiple Myeloma (MajesTEC-1): a Multicentre, Open-Label, Single-Arm, Phase 1 Study," The Lancet (Aug. 1, 2021) vol. 398, No. 10301, pp. 665-674.
Vaughan et al., "Human Antibodies with Sub-Nanomolar Affinities Isolated from a Large Non-Immunized Phage Display Library," Nature Biotechnology (Mar. 1996) vol. 14, pp. 309-314.
Ward et al., "Binding Activities of a Repertoire of Single Immunoglobulin Variable Domains Secreted from *Escherichia coli*," Nature (1989) vol. 341, pp. 544-546.
Wu et al., "An Analysis of the Sequences of the Variable Regions on Bence Jones Proteins and Myeloma Light Chains and Their Implications for Anti-Body Complementarity," J. Exp. Med. (1970) 132, pp. 211-250.
XP002762973, Anti-CD3 Epsilon Humanized Antibody VL Region Coding Gene, Seq ID 55, Database Geneseq (online), Jan. 17, 2013, Database Accession No. BAG88459.
XP002762974, Anti-Ha mAb (CL860UCA) Ligh Chain Variable Region Coding Gene, Seq 5, Database Geneseq (online) Apr. 11, 2013, Database Accession No. BAK30778.
XP002762975, Anti-CD3 Variant Humarized Antibody BH (XENP11810H1.15_L1.4), Seq 57, Database Geneseq (Online), Dec. 4, 2014, Database Accession No. BBP23340.
Yang et al., "A Common Pathway for T Lymphocyte Activation Involving Both the CD3-Ti Complex and CD2 Sheep Erythrocyte Receptor Determinants," The Journal of Immunology (1986) vol. 137, No. 4, pp. 1097-1100.
Zhou et al., "Development of A Simple and Rapid Method for Producing Non-Fucosylated Oligomannose Containing Antibodies With Increased Effector Function," Biotechnology and Bioengineering (2008) vol. 99, No. 3, pp. 652-665.
Krebs et al., "High-Throughput Generation and Engineering of Recombinant Human Antibodies," J. Immunol. Meth. (Aug. 1, 2001) vol. 254, pp. 67-84.
Kumar et al., "International Myeloma Working Group Consensus Criteria for Response and Minimal Residual Disease Assessment in Multiple Myeloma," Lancet. Oncol. (Aug. 2016) vol. 17(8), pp. e328-e346.

(56) References Cited

OTHER PUBLICATIONS

Laabi, et al., "A New Gene, BCM, on Chromosome 16 is Fused to the Interleukin 2 Gene by a t(4:16) (q26;p13) Translocation in a Malignant T Cell Lymphoma," The EMBO Journal, 11(11):3897-3904, (1992).

NCT03145181 "Dose Escalation Study of Teclistamab, a Humanized BCMA*CD3 Bispecific Antibody, in Participants With Relapsed or Refractory Multiple Myeloma (MajesTEC-1)," ClinicalTrials. gov identifier: NCT03145181 (Apr. 25, 2019) pp. 1-10.

Shah et al., "B-cell maturation antigen (BCMA) in multiple myeloma: rationale for targeting and current therapeutic approaches," Leukemia (2020) vol. 34, pp. 985-1005.

Girgis et al., "Exploratory Pharmacokinetic/Pharmacodynamic and Tolerability Study of BCMAxCD3 in Cynomolgus Monkeys," Blood (2016) vol. 128(22), p. 5668.

Zhao et al., "Bispecific antibodies targeting BCMA, GPRC5D, and FcRH5 for multiple myeloma therapy: latest updates from ASCO 2023 Annual Meeting," Journal of Hematology & Oncology (2023) vol. 16(92), pp. 1-4.

Abhinandan et al., "Analysis and Improvements to Kabat and Structurally Correct Numbering of Antibody Variable Domains", Molecular Immunology (2008) vol. 45, pp. 3832-3839.

Adams et al., "Recent Developments in the PHENIX Software for Automated Crystallographic Structure Determination," J. Synchrotron Rad. (2004) vol. 11, pp. 53-55.

Adriouch et al., "Extracellular NAD+: A Danger Signal Hindering Regulatory T Cells," Microbes and Infect. (Nov. 2012) vol. 14, Issue 14, pp. 1284-1292.

Anasetti et al., "Treatment of Acute Graft-Versus-Host Disease With a Nonmitogenic Anti-CD3 Monoclonal Antibody," Transplantation (Nov. 1992) vol. 54(5), pp. 844-851.

Avet-Loiseau et al. "Evaluation of Minimal Residual Disease (MRD) by Next Generation Sequencing (NGS) is Highly Predictive of Progression Free Survival in the IFM/DFCI 2009 Trial," Blood (Dec. 3, 2015) vol. 126, No. 23, p. 191.

Baert et al., "Influence of Immunogenicity on the Long-Term Efficacy of Infliximab in Crohn's Disease," N. Engl. J. Med. (2003) vol. 348, pp. 601-608.

Beiboer et al., "Guided Selection of a Pan Carcinoma Specific Antibody Reveals Similar Binding Characteristics yet Structural Divergence Between the Original Murine Antibody and its Human Equivalent," J. Mol. Biol. (2000) vol. 296, pp. 833-849.

Brudno et al., "T Cells Genetically Modified to Express an Anti-B-Cell Maturation Antigen Chimeric Antigen Receptor Cause Remissions of Poor-Prognosis Relapsed Multiple Myeloma," Journal of Clinical Oncology (Aug. 1, 2018) vol. 36, No. 22, pp. 2267-2280.

Caraccia et al. "Bispecific Antibodies for Multiple Myeloma: A Review of Targets, Drugs, Clinical Trials, and Future Directions," Frontiers in Immunology (Apr. 2020) vol. 11, pp. 1-25.

Casset et al., "A Peptide Mimetic of an Anti-CD4 Monoclonal Antibody by Rational Design," BBRC (2003) vol. 307, pp. 198-205.

Chames et al., "Bispecific Antibodies for Cancer Therapy," Current Opinion in Drug Discovery & Development (2009) vol. 12(2), pp. 276-283.

Chen, et al., "Thymoglobulin Efficiently Explands Cytokine-Induced Killler Cells in a Clinical-Grade Culture Protocol," Chin. J. Cell. Mol. Immunol., 30(7):681-690 (2014).

Chiarugi et al., "The NAD Metabolome—A Key Determinant of Cancer Cell Biology," Nature Reviews (Nov. 2012) vol. 12, pp. 741-752.

Chothia et al., "Canonical Structures for the Hypervariable Regions of Immunoglobulins," J. Mol. Biol., (1987) vol. 196, pp. 901-917.

Cline, "Perspectives for Gene Therapy: Inserting New Genetic Information into Mammalian Cells by Physical Techniques and Viral Vectors," Pharmac. Ther. (1985) vol. 29, pp. 69-92.

DeLano, "PyMOL: An Open-Source Molecular Graphics Tool," DeLano Scientific, (2002) pp. 1-9.

Drach et al., "Presence of a p53 Gene Deletion in Patients with Multiple Myeloma Predicts for Short Survival After Conventional-Dose Chemotherapy," Blood (1998) vol. 92(3), pp. 802-809.

Emsley et al., "Coot: Model-Building Tools for Molecular Graphics," Acta Cryst. (2004) D60, pp. 2126-2132.

European Search Report for European Patent Application No. 20177664.8 dated Nov. 23, 2020.

Facon et al., "Chromosome 13 Abnormalities Identified by FISH Analysis and Serum ?2-microglobulin Produce a Powerful Myeloma Staging System for Patients Receiving High-Dose Therapy," Blood (Mar. 15, 2001) vol. 91(6), pp. 1566-1571.

Ferrara et al., "Modulation of Therapeutic Antibody Effector Functions by Glycosylation Engineering: Influence of Golgi Enzyme Localization Domain and Co-Expression of Heterologous ?1, 4-N-acetylglucosaminyltransferase III and Golgi ?-mannosidase II," Biotechnology and Bioengineering (Apr. 5, 2006) vol. 93, No. 5, pp. 851-861.

Ferrara et al., "The Carbohydrate at FcyRIIIa Asn-162: An Element Required for High Affinity Binding to Non-Fuscosylated IgG Glycoforms," The Journal of Biological Chemistry (Feb. 24, 2006) vol. 281, No. 8, pp. 5032-5036.

Frerichs et al., "Preclinical Evaluation of the New BCMA x CD3 Bispecific Antibody JNJ-957 for the Treatment of Multiple Myeloma," HemaSphere (2018) 2(S1), p. 729, Abs. S1579.

Funaro et al., "Involvement of the Multilineage CD38 Molecule in a Unique Pathway of Cell Activation and Proliferation," J. Immunol. (Oct. 15, 1990) vol. 145, No. 8, pp. 2390-2396.

Gadi et al., "In Vivo Sensitization of Ovarian Tumors to Chemotherapy by Expression of *E. coli* Purine Nucleoside Phosphorylase in a Small Fraction of Cells," Gene Therapy (2000) vol. 7, pp. 1738-1743.

Garfall et al., "180 Updated Phase 1 Results of Teclistamab, a B-Cell Maturation Antigen (BCMA) x CD3 Bispecific Antibody, in Relapsed and/or Refractory Multiple Myeloma (RRMM)," 62nd ASH Annual Meeting and Exposition, Dec. 5-8, 2020, Abstract.

Garfall et al., "Updated Phase 1 Results of Teclistamab, a B-Cell Maturation Antigen (BCMA) x CD3 Bispecific Antibody, in Relapsed and/or Refractory Multiple Myeloma (RRMM)," Blood (Nov. 5, 2020) vol. 136, Suppl. 1, p. 27.

Garfall et al., "Updated Phase 1 Results of Teclistamab, a B-Cell Maturation Antigen (BCMA) x CD3 Bispecific Antibody, in Relapsed and/or Refractory Multiple Myeloma (RRMM)," Presented at the 62nd ASH Annual Meeting, 2020, Abstract 180.

Gertz et al., "Clinical Implications of t(11;14)(q13;q32), t(4;14)(p16.3;q32), and 17p13 in Myeloma Patients Treated with High-Dose Therapy," Blood (2005) vol. 106(8), pp. 2837-2840.

Girgis et al., "3194 Translational Approach of Using Ex Vivo Cytotoxicity and Early Clinical Data to Predict Teclistamab Efficacious Therapeutic Range in Multiple Myeloma Patients," 62nd ASH Annual Meeting and Exposition, Dec. 5-8, 2020, Abstract.

Girgis et al., "Effects of Teclistamab and Talquetamab on Soluble BCMA Levels in Patients with Relapsed/Refractory Multiple Myeloma," Blood Advances (Aug. 25, 2022) pp. 1-21.

Girgis et al., "Teclistamab and Talquetamab Modulate Levels of Soluble B-Cell Maturation Antigen in Patients with Relapsed and/or Refractory Multiple Myeloma," Journal of Clinical Oncology (May 20, 2021) vol. 39, No. 15 Suppl, p. 8047.

Girgis et al., "Translational Approach of Using Ex Vivo Cytotoxicity and Early Clinical Data to Predict Teclistamab Efficacious Therapeutic Range in Multiple Myeloma Patients," Blood (Nov. 5, 2020) vol. 136, Suppl. 1, p. 35.

Girgis et al., "Translational Approach of Using Ex Vivo Cytotoxicity and Early Clinical Data to Predict Teclistamab Efficacious Therapeutic Range in Multiple Myeloma Patients," Presented at the 62nd ASH Annual Meeting & Exposition, Dec. 5-8, 2020.

Gras et al., "BCMAp: An Integral Membrane Protein in the Golgi Aapparatus of Human Mature B Lymphocytes," International Immunology (1995) vol. 7, No. 7, pp. 1093-1106.

Gross et al., "TACI and BCMA are Receptors for a TNF Homologue Implicated in B-Cell Autoimmmune Disease," Nature, 404:995-999, (Apr. 27, 2000).

Guse et al., "Regulation of Calcium Signalling in T Lymphocytes by the Second Messenger Cyclic ADP-Ribose," Nature (Mar. 4, 1999) vol. 398, pp. 70-73.

(56) References Cited

OTHER PUBLICATIONS

Hagner et al., "Targeting B-Cell Maturation Antigen (BCMA with CC-93269, a 2+1 T Cell Engager, Elicits Significant Apoptosis in Diffuse Large B-Cell Lymphoma Preclinical Models," Blood (Nov. 13, 2019) vol. 134, p. 1580.

Holliger et al., "Diabodies: Small Bivalent and Bispecific Antibody Fragments," Proc. Natl. Acad. Sci. USA (Jul. 1993) vol. 90, pp. 6444-6448.

Holt et al., "Domain Antibodies: Proteins for Therapy," Trends in Biotechnology (Nov. 2003) vol. 21, No. 11, pp. 484-490.

Honegger et al., "Yet Another Numbering Scheme for Immunoglobulin Variable Domains: An Automatic Modeling and Analysis Tool," J. Mol. Biol. (2001) vol. 309, pp. 657-670.

Hoogenboom et al., "By-Passing Immunisation: Human Antibodies from Synthetic Repertoires of Germline VH Gene Segments Rearranged in Vitro," J. Mol. Biol. (1992) vol. 227, p. 381-388.

Hymowitz et al., "Structures of April-Receptor Complexes," The Journal of Biological Chemistry, 280(8): 7218-7227, (Feb. 25, 2005).

International Search Report and Written Opinion for International PCT Application No. PCT/US2022/079147 dated Jan. 27, 2023.

Keymeulen et al., "Insulin Needs after CDS-Antibody Therapy in New-Onset Type 1 Diabetes," The New England Journal of Medicine, 352(25):2598-2608, (Jun. 23, 2005).

Knappik et al., "Fully Synthetic Human Combinatorial Antibody Libraries (HuCAL) Based on Modular Consensus Frameworks and CDRs Randomized with Trinucleotides," J. Mol. Biol. (2000) vol. 296, pp. 57-86.

Konno et al., "Fucose Content of Monoclonal Antibodies can be Controlled by Culture Medium Osmolality for High Antibody-Dependent Cellular Cytotoxicity," Cytotechnology (2012) vol. 64, pp. 249-265.

\* cited by examiner

METHODS OF TREATING CANCERS AND ENHANCING EFFICACY OF BCMAxCD3 BISPECIFIC ANTIBODIES

CROSS REFERENCE TO RELATED APPLICATIONS

This application claims the benefit of U.S. Provisional Application Ser. No. 63/275,368 filed 3 Nov. 2021, and U.S. Provisional Application Ser. No. 63/288,279 filed 10 Dec. 2021, and U.S. Provisional Application Ser. No. 63/348,036 filed 2 Jun. 2022, each of which is hereby incorporated by reference in their entirety.

REFERENCE TO SEQUENCE LISTING SUBMITTED ELECTRONICALLY

The instant application contains a Sequence Listing which has been submitted electronically in XML format and is hereby incorporated by reference in its entirety. Said XML copy, created on Nov. 1, 2022 is named "258199.060901_PRD4190USNP1_SL.xml" and is 64.1 kilobytes in size.

FIELD OF THE INVENTION

Disclosed are methods of treating cancers and enhancing efficacy of BCMAxCD3 bispecific antibodies.

BACKGROUND OF THE INVENTION

From 1990-2016 Multiple Myeloma (MM) incident cases increased by 126%, and deaths increased by 94% worldwide. In the United States in 2020, it is estimated that there will be 32,270 newly diagnosed cases of MM with 140,779 people living with the disease. In Europe, multiple myeloma is the second most common hematologic malignancy, with 35,842 new cases estimated in the 27 European countries in 2020 (European Cancer Information System 2020). Despite multiple therapeutic options, the disease most often recurs and remains incurable. With each successive relapse, symptoms return, quality of life worsens, and the chance and duration of response typically decreases.

Relapsed and refractory multiple myeloma constitutes a specific unmet medical need. Patients who progress after receiving standard therapies (such as proteasome inhibitors [PI] or immunomodulatory drugs [IMiDs]) are challenging to treat since they have already been exposed to 2 major drug classes, and new effective and convenient treatment options are needed. Despite myeloma remaining an incurable disease, <40% of patients receive a third line of therapy. Lenalidomide-containing regimens have increasingly become standard-of-care first-line therapies in the US and in most of Europe both in transplant-eligible and transplant-ineligible patients. As a result of these practice patterns, most patients with relapsed multiple myeloma are lenalidomide-exposed when they first relapse.

T cell redirected killing is a desirable mode of action in many therapeutic areas. In general T cell redirecting molecules are engineered to have at least two antigen binding sites wherein one site binds a surface antigen on a target cell and the other site binds a T cell surface antigen. Amongst T cell surface antigens, the human CD3 epsilon subunit from the TCR protein complex has been the most targeted to redirect T cell killing. Various bispecific antibody formats have been shown to mediate T cell redirection in both in pre-clinical and clinical investigations.

Tumors evade immune recognition through creating an immunosuppressive tumor microenvironment (TME). In the TME, under conditions of persistent antigen and inflammation, T cells become exhausted, or dysfunctional, and progressively lose their effector function and proliferative capacity. Impaired function and number of available T cells to engage therapeutics mediating T cell redirected killing may impair anti-tumor efficacy of the therapeutic. There is a need to enhance T cell functionality for optimal efficacy of the therapeutics mediating T cell redirected killing.

Teclistamab (Tec) is a bispecific antibody that binds to B-cell maturation antigen (BCMA) and CD3. Daratumumab (Dara) is a monoclonal antibody approved for MM treatment that targets CD38 on MM cells, resulting in direct cytotoxicity of MM cells. Novel agents are needed for treating cancer, particularly multiple myeloma (MM), which remains incurable with most patients (pts) relapsing or becoming refractory to standard therapies.

SUMMARY OF THE INVENTION

It is now discovered that, using a dosage regimen described in this application, a combination of a BCMAxCD3 bispecific antibody and an anti-CD38 antibody DARZALEX® (daratumumab), each of which mediates killing of multiple myeloma cells upon target engagement on the same cell, can be safely administered to a subject to treat a cancer, particularly a relapsed/refractory MM.

In one general aspect, the application relates to a method of treating a cancer, such as multiple myeloma, in a subject in need thereof, comprising:
  (1) administering to the subject a BCMAxCD3 bispecific antibody at a dose of 200 µg/kg to 6 mg/kg or 60 mg to 600 mg every 1-4 weeks, and
  (2) subcutaneously administering to the subject an anti-CD38 antibody at a dose of 1200 mg to 2400 mg every 1-4 weeks.

In some embodiments, the BCMAxCD3 bispecific antibody is administered to the subject intravenously at a dose of 200 µg/kg to 350 µg/kg, such as 200, 210, 220, 230, 240, 250, 260, 270, 280, 290, 300, 310, 320, 330, 340, 350 µg/kg or any dose in-between, every 1-4 weeks.

In some embodiments, the method comprises:
  (1) subcutaneously administering to the subject the BCMAxCD3 bispecific antibody at a dose of 1 mg/kg to 6 mg/kg or 200 mg to 400 mg every 1-4 weeks, and
  (2) subcutaneously administering to the subject the anti-CD38 antibody at a dose of 1600 mg to 2000 mg every 1-4 weeks.

In some embodiments, the method further comprises subcutaneously administering to the subject the BCMAxCD3 bispecific antibody at a dose lower than 0.5 mg/kg prior to step (1).

According to embodiments of the application, the BCMAxCD3 bispecific antibody is subcutaneously administered to the subject at a dose of 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 5, 5.5, or 6 mg/kg, or in a fixed dose of 60, 100, 150, 200, 250, 260, 270, 280, 290, 300, 310, 320, 330, 340, 350, 400 mg, 450 mg, 500 mg, 550 mg, or 600 mg, or any dose in-between, once every week, once every two weeks or once every four weeks. For example, the BCMAxCD3 bispecific antibody can be subcutaneously administered to the subject at a dose of 1.5 mg/kg weekly, 3.0 mg/kg weekly or biweekly, or 300 mg biweekly.

In an embodiment of the application, the BCMAxCD3 bispecific antibody is subcutaneously administered to the subject at a dose of 1.5 mg/kg weekly, and the anti-CD38 antibody is subcutaneously administered to the subject in the dose of 1800 mg once every week during week 1 to week 8 of the treatment, once every two weeks during week 9 to week 24 of the treatment, and once every four weeks after week 24 of the treatment.

In another embodiment of the application, the BCMAxCD3 bispecific antibody is subcutaneously administered to the subject at a dose of 1.5 mg/kg once every week during week 1 to week 8 of the treatment, and at a dose of 3.0 mg/kg once every two weeks after week 8 of the treatment, such as during week 9 to week 24 of the treatment, and the anti-CD38 antibody is subcutaneously administered to the subject in the dose of 1800 mg once every week during week 1 to week 8 of the treatment, once every two weeks during week 9 to week 24 of the treatment, and once every four weeks after week 24 of the treatment.

In some embodiments, the BCMAxCD3 bispecific antibody is subcutaneously administered at 6.0 mg/kg once every month after week 8 of the treatment, such as after 4-12 weeks of the biweekly subcutaneous administration of 3.0 mg/kg.

In some embodiments, the anti-CD38 antibody is administered or provided for administration together with rHuPH20, such as about 30,000 U of rHuPH20.

Any suitable BCMAxCD3 bispecific antibody can be used in a method of the application. In some embodiments, a BCMAxCD3 bispecific antibody useful for the application comprises:
(i) a BCMA binding domain comprising a heavy chain variable region (VH) having heavy chain complementarity determining regions (HCDRs) HCDR1, HCDR2, and HCDR3 of the amino acid sequences of SEQ ID NO: 18, SEQ ID NO: 19, and SEQ ID NO: 20, respectively, and a light chain variable region (VL) having light chain complementarity determining regions (LCDRs) LCDR1, LCDR2, and LCDR3 of the amino acid sequences of SEQ ID NO: 21, SEQ ID NO: 22, and SEQ ID NO: 23, respectively, and
(ii) a CD3 binding domain comprising a VH having HCDR1, HCDR2, and HCDR3 of the amino acid sequences of SEQ ID NO: 28, SEQ ID NO: 29, and SEQ ID NO: 30, respectively, and a VL having LCDR1, LCDR2, and LCDR3 of the amino acid sequences of SEQ ID NO: 31, SEQ ID NO: 32, and SEQ ID NO: 33, respectively.

In some embodiments, the BCMA binding domain comprises the VH having the amino acid sequence of SEQ ID NO: 24 and the VL having the amino acid sequence of SEQ ID NO: 25. The CD3 binding domain comprises the VH having the amino acid sequence of SEQ ID NO: 34 and the VL having the amino acid sequence of SEQ ID NO: 35. Preferably, the BCMAxCD3 bispecific antibody comprises a first heavy chain (HC1) having the amino acid sequence of SEQ ID NO: 26, a first light chain (LC1) having the amino acid sequence of SEQ ID NO: 27, a second heavy chain (HC2) having the amino acid sequence of SEQ ID NO: 36, and a second light chain (LC2) having the amino acid sequence of SEQ ID NO: 37. More preferably, the BCMAxCD3 bispecific antibody is teclistamab.

In some embodiments, the anti-CD38 antibody comprises a VH having HCDR1, HCDR2, and HCDR3 of the amino acid sequences of SEQ ID NO: 8, SEQ ID NO: 9, and SEQ ID NO: 10, respectively, and a VL having LCDR1, LCDR2, and LCDR3 of the amino acid sequences of SEQ ID NO: 11, SEQ ID NO: 12, and SEQ ID NO: 13, respectively. Preferably, the anti-CD38 antibody comprises the VH having the amino acid sequence of SEQ ID NO: 6, and the VL having the amino acid sequence of SEQ ID NO: 7. More preferably, the anti-CD38 antibody is daratumumab.

In one embodiment, the application relates to a method of treating multiple myeloma in a subject in need thereof, comprising:
(1) subcutaneously administering to the subject 1.5 mg/kg of a BCMAxCD3 bispecific antibody once every week during week 1 to week 8 of the treatment, and 3.0 mg/kg of the BCMAxCD3 bispecific antibody once every two weeks and/or 6.0 mg/kg of a BCMAxCD3 bispecific antibody once every month after week 8 of the treatment, and
(2) subcutaneously administering to the subject 1800 mg of an anti-CD38 antibody once every week during week 1 to week 8 of the treatment, once every two weeks during week 9 to week 24 of the treatment, and once every four weeks after week 24 of the treatment, wherein the BCMAxCD3 bispecific antibody comprises a first heavy chain (HC1) of SEQ ID NO: 26, a first light chain (LC1) of SEQ ID NO: 27, a second heavy chain (HC2) of SEQ ID NO: 36, and a second light chain (LC2) of SEQ ID NO: 37, and the anti-CD38 antibody comprises the HC of SEQ ID NO: 14 and the LC of SEQ ID NO: 15.

In some embodiments of the application, the subject has received at least one prior treatment of multiple myeloma, preferably, the subject is relapsed or refractory to the at least one prior treatment, more preferably, the prior treatment comprises at least one of a proteasome inhibitor (PI) and an immunomodulatory agent (IMiD). The subject can be refractory or relapsed to a treatment, such as a treatment selected from the group consisting of an anti-CD38 antibody, lenalidomide, bortezomib, pomalidomide, carfilzomib, elotuzumab, ixazomib, melphalan and thalidomide, or any combination thereof. Preferably, if the subject has received only 1 prior line of therapy, the subject is lenalidomide refractory.

In some embodiments, a method of the application further comprises administering to the subject another treatment for the cancer, including but not limited to, pomalidomide, daratumumab, dexamethasone, bortezomib, and lenalidomide.

In some embodiments, a method according to embodiments of the application results in T-cell activation, such as an increase in at least one of CD25, PD-1, CD38 on CD4 and CD8 T cells. A method according to embodiments of the application can also result in an increase in frequency of at least of CD38+ CD8+ T cells, CD38+ CD4+T cells and Tregs T cells.

Another general aspect of the application relates to an anti-CD38 antibody as described herein for use in a method of treating a cancer, such as MM, more particularly a relapsed or refractory MM, wherein the method comprises:
(1) administering to the subject a BCMAxCD3 bispecific antibody at a dose of 200 µg/kg to 6 mg/kg or 60 mg to 600 mg every 1-4 weeks, and
(2) subcutaneously administering to the subject the anti-CD38 antibody at a dose of 1200 mg to 2400 mg every 1-4 weeks.

Another general aspect of the application relates to a BCMAxCD3 bispecific antibody as described herein for use in treating a cancer, such as MM, more particularly a relapsed or refractory MM, wherein the treatment comprises:

(1) administering to the subject the BCMAxCD3 bispecific antibody at a dose of 200 µg/kg to 6 mg/kg or 60 mg to 600 mg every 1-4 weeks, and
(2) subcutaneously administering to the subject an anti-CD38 antibody at a dose of 1200 mg to 2400 mg every 1-4 weeks.

Yet another general aspect of the application relates to a combination or a kit of an anti-CD38 antibody as described herein and a BCMAxCD3 bispecific antibody as described herein for use in treating a cancer, such as MM, more particularly a relapsed or refractory MM, wherein the treatment comprises:
(1) administering to the subject a BCMAxCD3 bispecific antibody at a dose of 200 µg/kg to 6 mg/kg or 60 mg to 600 mg every 1-4 weeks, and
(2) subcutaneously administering to the subject the anti-CD38 antibody at a dose of 1200 mg to 2400 mg every 1-4 weeks.

The application further relates to use of a combination of an anti-CD38 antibody as described herein and a BCMAxCD3 bispecific antibody as described herein in the manufacture of a medicament for treating a cancer, such as MM, more particularly a relapsed or refractory MM, wherein the treatment comprises:
(1) administering to the subject a BCMAxCD3 bispecific antibody at a dose of 200 µg/kg to 6 mg/kg or 60 mg to 600 mg every 1-4 weeks, and
(2) subcutaneously administering to the subject the anti-CD38 antibody at a dose of 1200 mg to 2400 mg every 1-4 weeks.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

DETAILED DESCRIPTION OF THE INVENTION

Figure 1:
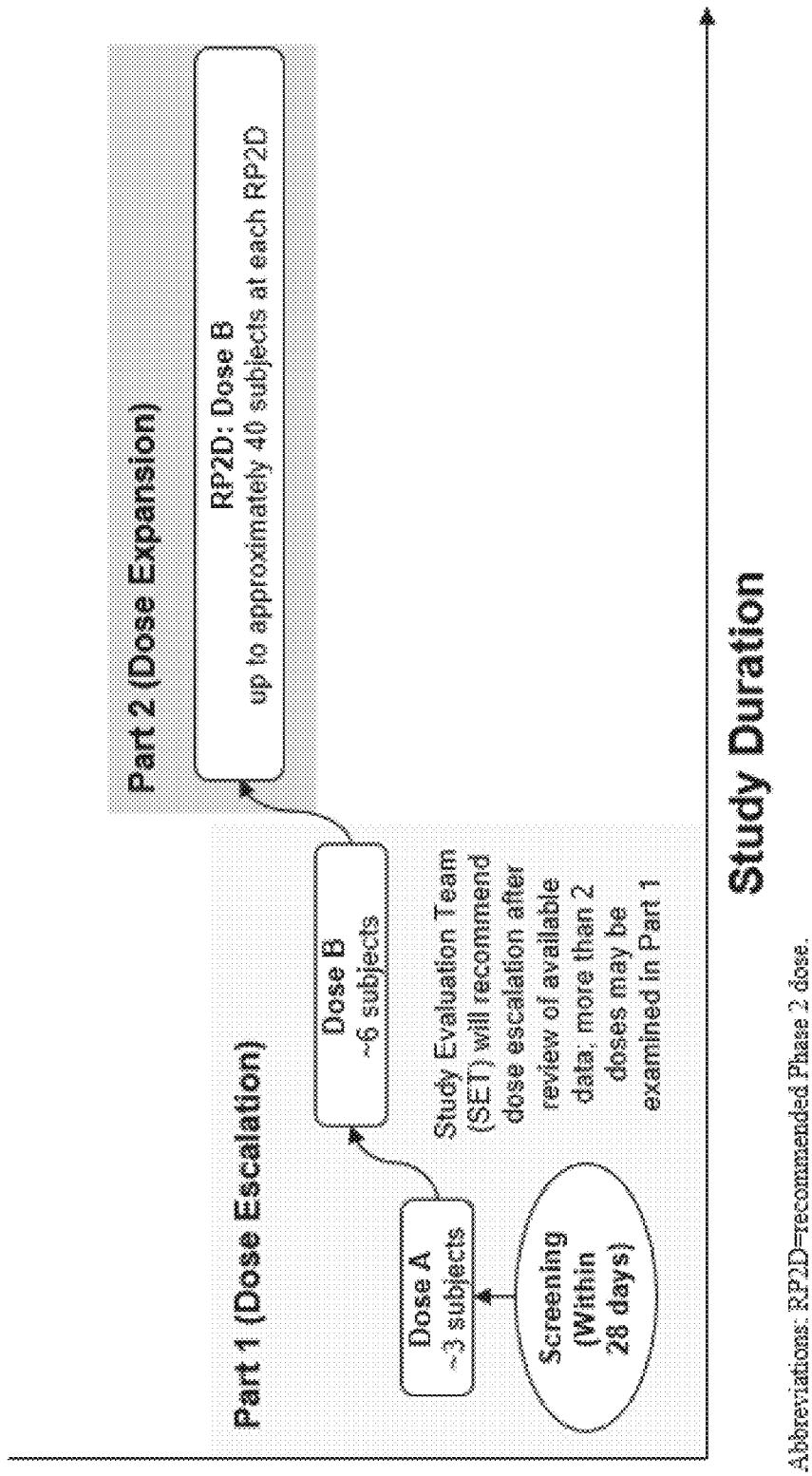
FIG. 1 is a schematic of overview of Part 1 and Part 2 of a phase 1 study of teclistamab administered in combination with subcutaneous daratumumab for relapsed or refractory multiple myeloma (RRMM).

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods. All patents, patent applications and publications cited herein are incorporated by reference as if set forth fully herein.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, the singular forms "a," "an," and "the" include the plural unless the context clearly dictates otherwise. Thus, for example, reference to "a cell" includes a combination of two or more cells, and the like.

Unless otherwise stated, any numerical value, such as a concentration or a concentration range described herein, are to be understood as being modified in all instances by the term "about." Thus, a numerical value typically includes +10% of the recited value. For example, a dosage of 10 mg includes 9 mg to 11 mg. As used herein, the use of a numerical range expressly includes all possible subranges, all individual numerical values within that range, including integers within such ranges and fractions of the values unless the context clearly indicates otherwise.

"About" when used in reference to numerical ranges, cutoffs, or specific values means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of an assay, result or embodiment, "about" means within one standard deviation per the practice in the art, or a range of up to 10%, whichever is larger.

"Antibodies" is meant in a broad sense and includes immunoglobulin molecules including monoclonal antibodies including murine, human, humanized and chimeric monoclonal antibodies, antigen binding fragments, multispecific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g., IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4. Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Antigen binding fragment" or "antigen binding domain" refers to a portion of an immunoglobulin molecule that binds an antigen. Antigen binding fragments may be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"BCMA" refers to human B-cell maturation antigen, also known as CD269 or TNFRSF17. A human BCMA (UniProt Q02223) contains the amino acid sequence of SEQ ID NO: 1. The extracellular domain of the human BCMA encompasses residues 1-54 of SEQ ID NO: 1.

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca cynomolgus* (cynomolgus, cyno) or *Pan troglodytes*, or may bind an epitope that is shared between two or more distinct antigens.

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor.

"CD3" refers to a human antigen which is expressed on T cells as part of the multimolecular T cell receptor (TCR) complex and which consists of a homodimer or heterodimer formed from the association of two or four receptor chains: CD3 epsilon, CD3 delta, CD3 zeta and CD3 gamma. Human CD3 epsilon comprises the amino acid sequence of SEQ ID NO: 2. SEQ ID NO: 3 shows the extracellular domain of CD3 epsilon.

"CD38" refers to the CD38 protein (synonyms: ADP-ribosyl cyclase 1, cADPr hydrolase 1, cyclic ADP-ribose hydrolase 1). A human CD38 (UniProt accession no. P28907) has the amino acid sequence as shown in SEQ ID NO: 4. CD38 is a single pass type II transmembrane protein with amino acid residues 1-21 representing the cytosolic domain, amino acid residues 22-42 representing the transmembrane domain, and residues 43-300 representing the extracellular domain.

"CH3 region" or "CH3 domain" refers to the CH3 region of an immunoglobulin. The CH3 region of human IgG1 antibody corresponds to amino acid residues 341-446. However, the CH3 region may also be any of the other antibody isotypes as described herein.

"Chimeric antigen receptor" or "CAR" refers to engineered T cell receptors which graft a ligand or antigen specificity onto T cells (for example naive T cells central memory T cells effector memory T cells or combinations thereof). CARs are also known as artificial T-cell receptors, chimeric T-cell receptors or chimeric immunoreceptors. CARs comprise an extracellular domain capable of binding to an antigen, a transmembrane domain and at least one intracellular domain. CAR intracellular domain comprises a polypeptide known to function as a domain that transmits a signal to cause activation or inhibition of a biological process in a cell. The transmembrane domain comprises any peptide or polypeptide known to span the cell membrane and that can function to link the extracellular and signaling domains. A chimeric antigen receptor may optionally comprise a hinge domain which serves as a linker between the extracellular and transmembrane domains.

"Combination" means that two or more therapeutics are administered to a subject together in a mixture, concurrently as single agents or sequentially as single agents in any order.

"Complementarity determining regions" (CDR) are antibody regions that bind an antigen. CDRs may be defined using various delineations such as Kabat (Wu et al. J Exp Med 132: 211-50, 1970) (Kabat et al., Sequences of Proteins of Immunological Interest, 5th Ed. Public Health Service, National Institutes of Health, Bethesda, Md., 1991), Chothia (Chothia et al. J Mol Biol 196: 901-17, 1987), IMGT (Lefranc et al. Dev Comp Immunol 27: 55-77, 2003) and AbM (Martin and Thornton J Bmol Biol 263: 800-15, 1996). The correspondence between the various delineations and variable region numbering are described (see e.g., Lefranc et al. Dev Comp Immunol 27: 55-77, 2003; Honegger and Pluckthun, J Mol Biol 309:657-70, 2001; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification. Correspondence between the numbering system, including, for example, the Kabat numbering and the IMGT unique numbering system, is well known to one skilled in the art (see, e.g., Kabat; Chothia; Martin; Lefranc et al.).

TABLE 1

Kabat, IMGT, AbM, and Chothia numbering systems.

| | IMGT | Kabat | AbM | Chothia |
|---|---|---|---|---|
| $V_H$ CDR1 | 27-38 | 31-35 | 26-35 | 26-32 |
| $V_H$ CDR2 | 56-65 | 50-65 | 50-58 | 53-55 |
| $V_H$ CDR3 | 105-117 | 95-102 | 95-102 | 96-101 |
| $V_L$ CDR1 | 27-38 | 24-34 | 24-34 | 26-32 |
| $V_L$ CDR2 | 56-65 | 50-56 | 50-56 | 50-52 |
| $V_L$ CDR3 | 105-117 | 89-97 | 89-97 | 91-96 |

"Comprising" is intended to include examples encompassed by the terms "consisting essentially of" and "consisting of;" similarly, the term "consisting essentially of" is intended to include examples encompassed by the term "consisting of." Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to."

"Enhance" or "enhanced" refers to enhancement in one or more functions of a test molecule when compared to a control molecule or a combination of test molecules when compared to one or more control molecules. Exemplary functions that can be measured are tumor cell killing, T cell activation, relative or absolute T cell number, Fc-mediated effector function (e.g., ADCC, CDC and/or ADCP) or binding to an Fcγ receptor (FcγR) or FcRn. "Enhanced" may be an enhancement of about 10%, 20%, 30%, 40%, 50%, 60%, 70%, 80%, 90%, 100% or more, or a statistically significant enhancement.

"Fc gamma receptor" (FcγR) refers to well-known FcγRI, FcγRIIa, FcγRIIb or FcγRIII. Activating FcγR includes FcγRI, FcγRIIa and FcγRIII.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Mutation" refers to an engineered or naturally occurring alteration in a polypeptide or polynucleotide sequence when compared to a reference sequence. The alteration may be a substitution, insertion or deletion of one or more amino acids or polynucleotides.

"Non-fixed combination" refers to separate pharmaceutical compositions of the BCMAxCD3 bispecific antibody and the anti-CD38 antibody administered as separate entities either simultaneously, concurrently or sequentially with no specific intervening time limits, wherein such administration provides effective levels of the two compounds in the body of the subject.

"Multispecific" refers to an antibody that specifically binds at least two distinct antigens or at least two distinct epitopes within the same antigen. Multispecific antibody may bind for example two, three, four or five distinct antigens or distinct epitopes within the same antigen.

"Pharmaceutical composition" refers to composition that comprises an active ingredient and a pharmaceutically acceptable carrier.

"Pharmaceutically acceptable carrier" or "excipient" refers to an ingredient in a pharmaceutical composition, other than the active ingredient, which is nontoxic to a subject.

"Philadelphia chromosome" or "Ph" refers to a well-known chromosomal translocation between chromosomes 9 and 22, resulting in the oncogenic BCR-ABL gene fusion with constitutively active tyrosine kinase activity. The translocation results in a portion of the BCR gene from chromosome 22q11 becoming fused with a portion of the ABL gene from chromosome 9q34, and is designated as t(9;22)(q34; q11) under the International System for Human Cytogenetic Nomenclature (ISCN). Depending on the precise location of the fusion, the molecular weight of the resulting fusion protein can range from 185 to 210 kDa. "Philadelphia chromosome" refers to all BCR-ABL fusion proteins formed due the (9;22)(q34;q11) translocation.

"Recombinant" refers to DNA, antibodies and other proteins that are prepared, expressed, created or isolated by recombinant means when segments from different sources are joined to produce recombinant DNA, antibodies or proteins.

"Reduce" or "reduced" refers to a reduction in one or more functions of a test molecule when compared to a control molecule or a combination of test molecules when compared to one or more control molecules. Exemplary functions that can be measured are tumor cell killing, T cell activation, relative or absolute T cell number, Fc-mediated effector function (e.g., ADCC, CDC and/or ADCP) or binding to an Fcγ receptor (FcγR) or FcRn. "Reduced" may be a reduction of about 10%, 20%, 30%, 40%, 50%, 60%, 70%, 80%, 90%, 100% or more, or a statistically significant enhancement.

"rHuPh20" refers to recombinant human hyalurodinase having the amino acid sequence of SEQ ID NO: 5, which is a recombinant hyaluronidase (HYLENEX® recombinant) described in Int'l Pat. Pub. No. WO2004/078140.

"Refractory to a therapy" refers to a cancer that is not amendable to surgical intervention and is initially unresponsive to the therapy.

"Relapsed" refers to a cancer that responded to a treatment but then returns.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

"BCMAxCD3 bispecific antibody" refers to a molecule containing two or more binding regions, wherein one of the binding regions specifically binds the cell surface antigen B-cell maturation antigen (BCMA) on a target cell or tissue and wherein a second binding region of the molecule specifically binds a T cell antigen CD3. This dual/multitarget binding ability recruits T cells to the target cell or tissue leading to the eradication of the target cell or tissue.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Treat" or "treatment" refers to both therapeutic treatment and prophylactic or preventative measures, wherein the object is to prevent or slow down (lessen) an undesired physiological change or disorder. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented.

"Tumor cell" or a "cancer cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, uptake of exogenous nucleic acid or it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo.

The numbering of amino acid residues in the antibody constant region throughout the specification is according to the EU index as described in Kabat et al., Sequences of Proteins of Immunological Interest, 5th Ed. Public Health Service, National Institutes of Health, Bethesda, MD. (1991), unless otherwise explicitly stated. Antibody constant chain numbering can be found for example at ImMunoGeneTics website, at IMGT Web resources at IMGT Scientific charts.

The substitutions in the CH3 region are expressed as modified position(s) in the first CH3 domain of the first heavy chain/modified position(s) in the second CH3 domain of the second heavy chain. For example, F405L/K409R refers to a F405L mutation in the first CH3 region and K09R mutation in the second CH3 region. L351Y_F405A_Y407V/T394W refers to L351Y, F40FA and Y407V mutations in the first CH3 region and T394W mutation in the second CH3 region. D399FHKRQ/K409AGRH refers to mutation in which D399 may be replaced by F, H, K R or Q, and K409 may be replaced by A, G, R or H.

Conventional one and three-letter amino acid codes are used herein as shown in Table 2.

TABLE 2

Amino acid abbreviations.

| Amino acid | Three-letter code | One-letter code |
|---|---|---|
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Pomalidomide" also termed "POMALYST@" refers to an analog of thalidomide, which is a third generation IMiD (immunomodulatory drug) with antineoplastic activity. IMiDs, such as lenalidomide and pomalidomide, form the backbone of several current multiple myeloma treatment regimens. Their exact mechanism of action is not fully understood, but IMiDs have an immunomodulatory effect on the multiple myeloma tumor microenvironment and can affect expression of tumor suppressor genes, promote apoptosis of myeloma cells, and enhance NK mediated myeloma cell lysis. The combination of daratumumab with IMiDs has been evaluated in multiple studies and demonstrated significant improvement in efficacy.

The dosing frequencies provided for herein are understood to be synonymous with standard terms in the art. For example, "weekly" dosing is understood to be synonymous with "QW". For example, "biweekly" dosing is understood to be synonymous with "Q2W". For example, "once every four weeks" is understood to be synonymous with "Q4W". Unless explicitly stated to the contrary, "once every four weeks" and "monthly" are used interchangeably in the context of dosing frequencies. Accordingly, "monthly" or "once a month" is also understood to be synonymous with "Q4W" unless explicitly stated otherwise.

In one general aspect, the application relates to a method of treating a cancer, such as MM, preferably a refractory or relapsed MM, comprising administering to the subject a BCMAxCD3 bispecific antibody at a dose of 100 μg/kg to 6 mg/kg or a fixed dose of 60 mg to 600 mg every 1-4 weeks, and subcutaneously administering to the subject an anti-CD38 antibody at a dose of 1200 mg to 2400 mg every 1-4 weeks.

The disclosure also provides a method of killing a tumor cell in a subject in need thereof, comprising administering to the subject a BCMAxCD3 bispecific antibody at a dose of 200 μg/kg to 6 mg/kg or a fixed dose of 60 mg to 600 mg every 1-4 weeks, and subcutaneously administering to the subject an anti-CD38 antibody at a dose of 1200 mg to 2400 mg every 1-4 weeks to thereby kill the tumor cell in the subject.

The disclosure further provides a method of enhancing the activity of at least one of a BCMAxCD3 bispecific antibody and an anti-CD38 antibody in a subject in need thereof, comprising administering to the subject the BCMAxCD3 bispecific antibody at a dose of 200 μg/kg to 6 mg/kg or a fixed dose of 60 mg to 600 mg every 1-4 weeks, and subcutaneously administering to the subject the anti-CD38 antibody at a dose of 1200 mg to 2400 mg every 1-4 weeks to thereby kill the tumor cell in the subject.

In some embodiments, the anti-CD38 antibody is administered prior to administering the BCMAxCD3 bispecific antibody. For example, the anti-CD38 antibody is administered about 1, 2, 3, 4, 5, 6, 7, 8, 9, 10 hours prior to administering the BCMAxCD3 bispecific antibody. In certain embodiments, the anti-CD38 antibody and the BCMAxCD3 bispecific antibody are administered on the same day, and the anti-CD38 antibody is administered about 3 hours before the subcutaneous administration of the BCMAxCD3 bispecific antibody.

In some embodiments, the BCMAxCD3 bispecific antibody is administered weekly, biweekly, or once every four weeks. In some embodiments, the BCMAxCD3 bispecific antibody is administered weekly. In some embodiments, the BCMAxCD3 bispecific antibody is administered biweekly. In some embodiments, the BCMAxCD3 bispecific antibody is administered once every four weeks.

In some embodiments, the BCMAxCD3 bispecific antibody and the anti-CD38 antibody are each administered to a subject having cancer, such as multiple myeloma, in an amount sufficient to alleviate or at least partially arrest the disease being treated ("therapeutically effective amount").

In some embodiments, the BCMAxCD3 bispecific antibody is administered at a dose of 100 μg/kg to 6 mg/kg or a fixed dose of 60 mg to 600 mg weekly, biweekly, monthly, or any frequency in-between. For example, the BCMAxCD3 bispecific antibody can be administered intravenously at a dose of 100 μg/kg, 150 μg/kg, 200 μg/kg, 250 μg/kg, 300 μg/kg, 350 μg/kg, 400 μg/kg, 500 μg/kg, 550 μg/kg, 600 μg/kg, 650 μg/kg, 700 μg/kg, 750 μg/kg, 800 μg/kg, 850 μg/kg, 900 μg/kg, or 950 μg/kg, or any value in-between, and the administration can be weekly, biweekly, monthly, or any frequency in-between. The BCMAxCD3 bispecific antibody can be also administered subcutaneously at a dose of 1000 μg/kg, 1100 μg/kg, 1200 μg/kg, 1300 μg/kg, 1400 μg/kg, 1500 μg/kg, 1600 μg/kg, 1700 μg/kg, 1800 μg/kg, 1900 μg/kg, 2000 μg/kg, 2100 μg/kg, 2200 μg/kg, 2300 μg/kg, 2400 μg/kg, 2500 μg/kg, 2600 μg/kg, 2700 μg/kg, 2800 μg/kg, 2900 μg/kg, 3000 μg/kg, 3100 μg/kg, 3200 μg/kg, 3300 μg/kg, 3400 μg/kg, 3500 μg/kg, 3600 μg/kg, 3700 μg/kg, 3800 μg/kg, 3900 μg/kg, 4000 μg/kg, 4100 μg/kg, 4200 μg/kg, 4300 μg/kg, 4400 μg/kg, 4500 μg/kg, 4600 μg/kg, 4700 μg/kg, 4800 μg/kg, 4900 μg/kg, 5000 μg/kg, 5100 μg/kg, 5200 μg/kg, 5300 μg/kg, 5400 μg/kg, 5500 μg/kg, 5600 μg/kg, 5700 μg/kg, 5800 μg/kg, 5900 μg/kg, 6000 μg/kg, or any value in-between, and the administration can be weekly, biweekly, once every four weeks, or any frequency in-between. The BCMAxCD3 bispecific antibody can further be administered subcutaneously at a fixed dose of 60 mg, 100 mg, 150 mg, 200 mg, 300 mg, 400 mg, 450 mg, 500 mg, 600 mg, or any value in-between, and the administration can be weekly, biweekly, monthly, or any frequency in-between.

In some embodiments, the BCMAxCD3 bispecific antibody is subcutaneously administered at a dose of 1500 μg/kg weekly.

In some embodiments, the BCMAxCD3 bispecific antibody is subcutaneously administered at a dose of 3000 μg/kg weekly or biweekly.

In some embodiments, the BCMAxCD3 bispecific antibody is subcutaneously administered at a dose of 6 mg/kg, such as once every 4 weeks.

In some embodiments, the BCMAxCD3 bispecific antibody is subcutaneously administered at a dose of 600 mg, such as once every 4 weeks.

In some embodiments, the BCMAxCD3 bispecific antibody is subcutaneously administered at a dose of 300 mg biweekly.

In some embodiments, the fixed dose of the BCMAxCD3 bispecific antibody is determined via the subject's weight, wherein a subject at or below a certain weight threshold is administered a particular fixed dose of the BCMAxCD3 bispecific antibody and wherein a subject above a certain weight threshold is administered a separate particular fixed dose of the BCMAxCD3 bispecific antibody. In some embodiments, the weight threshold is 50 kg, 55 kg, 60 kg, 65 kg, 70 kg, greater than 70 kg, or any value in-between.

In some embodiments, the subject has a weight at or below a weight threshold selected from 50 kg, 55 kg, 60 kg, 65 kg, or 70 kg and is administered subcutaneously at a fixed dose of the BCMAxCD3 bispecific antibody of 60 mg, 100 mg, 150 mg, 200 mg, 300 mg, 400 mg, 450 mg, 500 mg, 600 mg, or any value in-between, and the administration can be weekly, biweekly, monthly, or any frequency in-between. In some embodiments, the subject has a weight greater than a weight threshold selected from 50 kg, 55 kg, 60 kg, 65 kg, or 70 kg and is administered subcutaneously at a fixed dose of the BCMAxCD3 bispecific antibody of 60 mg, 100 mg, 150 mg, 200 mg, 300 mg, 400 mg, 450 mg, 500 mg, 600 mg, or any value in-between, and the administration can be weekly, biweekly, monthly, or any frequency in-between. In some embodiments, the subject having a weight at or below the weight threshold and the subject having a weight above the weight threshold are administered fixed doses of the BCMAxCD3 bispecific antibody that are the same. In some embodiments, the subject having a weight at or below the weight threshold and the subject having a weight above the weight threshold are administered fixed doses of the BCMAxCD3 bispecific antibody that are different.

In some embodiments, the anti-CD38 antibody is subcutaneously administered at a dose of 8 mg/kg to about 16 mg/kg every 1-4 weeks. For example, the anti-CD38 antibody can be subcutaneously administered at a dose of 8 mg/kg, 8.5 mg/kg, 9 mg/kg, 9.5 mg/kg, 10 mg/kg, 10.5 mg/kg, 11 mg/kg, 11.5 mg/kg, 12, mg/kg, 12.5 mg/kg, 13 mg/kg, 13.5 mg/kg, 14 mg/kg, 14.5 mg/kg, 15 mg/kg, 15.5 mg/kg, 16 mg/kg, or any value in-between, and the administration can be once every week, every 2 weeks, every 3 weeks, or every 4 weeks, or any frequency in-between.

In some embodiments, the anti-CD38 antibody is administered subcutaneously in a fixed dose of 1200 to 2400 mg every 1-4 weeks. For example, the anti-CD38 antibody can be administered subcutaneously at a dose of 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, or any value in-between, and the administration can be once every week, every 2 weeks, every 3 weeks, or every 4 weeks, or any frequency in-between. In some embodiments, the anti-CD38 antibody is administered subcutaneously in a dose range of 1600 to 2000 mg every 1-4 weeks. For example, the anti-CD38 antibody can be administered subcutaneously at a dose of 1600 mg, 1650 mg, 1700 mg, 1750 mg, 1800 mg, 1850 mg, 1900 mg, 1950 mg, 2000 mg, or any value in-between, and the administration can be once every week, every 2 weeks, every 3 weeks, or every 4 weeks, or any frequency in-between.

In some embodiments, the anti-CD38 antibody is administered subcutaneously at a dose of 1800 mg weekly, biweekly, once every 2 weeks, or once every 4 weeks.

Step-up doses of the BCMAxCD3 bispecific antibody can be administered in the initial cycle. One or more step-up doses of the BCMAxCD3 bispecific antibody at a lower dosage amount can be administered to the subject prior to the initial administration of the dosage level for the weekly or biweekly treatment according to an embodiment of the application. In certain embodiments, a method according to the application further comprises subcutaneously administering to the subject 0.01 to 0.10 mg/kg, such as 0.01, 0.02, 0.03, 0.04, 0.05, 0.06, 0.07, 0.08, 0.09 and 0.10 mg/kg of the BCMAxCD3 bispecific antibody on Day 1 or Day 2 of the treatment, preferably on Day 2 of the treatment after the initial administration of the anti-CD38 antibody on Day 1. In other embodiments, a method according to the application further comprises subcutaneously administering to the subject 0.10 to 0.50 mg/kg, such as 0.10, 0.15, 0.20, 0.25, 0.30, 0.35, 0.40, 0.45 or 0.50 mg/kg, or any value in-between, of the BCMAxCD3 bispecific antibody on Day 3, Day 4 or Day 5, preferably Day 4 of the treatment, prior to the initial subcutaneous administration of the BCMAxCD3 bispecific antibody at the dose for its weekly or biweekly administration.

In certain embodiments, a method according to the application further comprises subcutaneously administering to the subject a fixed dose of 1 to 10 mg, such as 1, 2, 3, 4, 5, 6, 7, 8, 9, or 10 mg of the BCMAxCD3 bispecific antibody on Day 1 or Day 2 of the treatment, preferably on Day 2 of the treatment after the initial administration of the anti-CD38 antibody on Day 1. In other embodiments, a method according to the application further comprises subcutaneously administering to the subject a fixed dose of 10 to 50 mg, such as 10, 15, 20, 25, 30, 35, 40, 45 or 50 mg, or any value in-between, of the BCMAxCD3 bispecific antibody on Day 3, Day 4 or Day 5, preferably Day 4 of the treatment, prior to the initial subcutaneous administration of the BCMAxCD3 bispecific antibody at the dose for its weekly or biweekly administration.

In some embodiments, the fixed dose of the BCMAxCD3 bispecific antibody is determined via the subject's weight, wherein a subject at or below a certain weight threshold is administered a particular fixed dose of the BCMAxCD3 bispecific antibody and wherein a subject above a certain weight threshold is administered a separate particular fixed dose of the BCMAxCD3 bispecific antibody. In some embodiments, the weight threshold is 50 kg, 55 kg, 60 kg, 65 kg, 70 kg, greater than 70 kg, or any value in-between.

In some embodiments, the subject has a weight at or below a weight threshold selected from 50 kg, 55 kg, 60 kg, 65 kg, or 70 kg and is administered subcutaneously at a fixed dose of the BCMAxCD3 bispecific antibody of 1, 2, 3, 4, 5, 6, 7, 8, 9, or 10 mg on Day 1 or Day 2 of the treatment, preferably on Day 2 of the treatment after the initial administration of the anti-CD38 antibody on Day 1. In some embodiments, the subject has a weight greater than a weight threshold selected from 50 kg, 55 kg, 60 kg, 65 kg, or 70 kg and is administered subcutaneously at a fixed dose of the BCMAxCD3 bispecific antibody of 1, 2, 3, 4, 5, 6, 7, 8, 9, or 10 mg on Day 1 or Day 2 of the treatment, preferably on Day 2 of the treatment after the initial administration of the anti-CD38 antibody on Day 1. In some embodiments, the subject having a weight at or below the weight threshold and the subject having a weight above the weight threshold are administered fixed doses of the BCMAxCD3 bispecific antibody that are the same. In some embodiments, the subject having a weight at or below the weight threshold and the subject having a weight above the weight threshold are administered fixed doses of the BCMAxCD3 bispecific antibody that are different.

In some embodiments, the subject has a weight at or below a weight threshold selected from 50 kg, 55 kg, 60 kg, 65 kg, or 70 kg and is administered subcutaneously at a fixed dose of the BCMAxCD3 bispecific antibody of 10, 15, 20, 25, 30, 35, 40, 45 or 50 mg, or any value in-between, of the BCMAxCD3 bispecific antibody on Day 3, Day 4 or Day 5, preferably Day 4 of the treatment, prior to the initial subcutaneous administration of the BCMAxCD3 bispecific antibody at the dose for its weekly or biweekly administration. In some embodiments, the subject has a weight greater than a weight threshold selected from 50 kg, 55 kg, 60 kg, 65 kg, or 70 kg and is administered subcutaneously at a fixed dose of the BCMAxCD3 bispecific antibody of 10, 15, 20, 25, 30, 35, 40, 45 or 50 mg, or any value in-between, of the BCMAxCD3 bispecific antibody on Day 3, Day 4 or Day 5, preferably Day 4 of the treatment, prior to the initial subcutaneous administration of the BCMAxCD3 bispecific antibody at the dose for its weekly or biweekly administration. In some embodiments, the subject having a weight at or below the weight threshold and the subject having a weight above the weight threshold are administered fixed doses of the BCMAxCD3 bispecific antibody that are the same. In some embodiments, the subject having a weight at or below the weight threshold and the subject having a weight above the weight threshold are administered fixed doses of the BCMAxCD3 bispecific antibody that are different.

In certain embodiments, a method of the application further comprises subcutaneously administering to the subject 0.06 mg/kg of the BCMAxCD3 bispecific antibody on Day 2 of the treatment and 0.3 mg/kg of the BCMAxCD3 bispecific antibody on Day 4 of the treatment, prior to the initial subcutaneous administration of the 1.5 mg/kg BCMAxCD3 bispecific antibody weekly or biweekly.

In certain embodiments, the method comprises subcutaneously administering to the subject 3 mg/kg of a BCMAxCD3 bispecific antibody biweekly.

In certain embodiments, a method of the application comprises subcutaneously administering to the subject 1.5 mg/kg of a BCMAxCD3 bispecific antibody weekly for 8 weeks (2 Cycles) followed by subcutaneously administering to the subject 3.0 mg/kg of a BCMAxCD3 bispecific antibody once every two weeks for 4 weeks (1 Cycle), and subcutaneously administering to the subject 1800 mg of an anti-CD38 antibody once every week during week 1 to week 8 of the treatment, once every two weeks during week 9 to week 24 of the treatment, and once every four weeks after week 24 of the treatment. In certain embodiments, the method comprises administering 3 mg/kg of a BCMAxCD3 bispecific antibody biweekly on Day 1 of the next planned 28 Day cycle following completion of the 3 Cycles.

The administration of the BCMAxCD3 bispecific antibody and/or the anti-CD38 antibody can be administered in 28-day cycles, and the treatment can comprise multiple cycles, such as 2, 3, 4, 5, 6, 7, 8, 9, 10 or more cycles. In certain embodiments, the BCMAxCD3 bispecific antibody and/or the anti-CD38 antibody is continuously administered in cycles unless a subject experiences progressive disease (PD). Repeated courses of treatment are also possible as chronic administration. The repeated administration can be at the same dose or at a different dose. For example, the BCMAxCD3 bispecific antibody can be subcutaneously administered at 1500 µg/kg or 3000 µg/kg at weekly intervals for 8 weeks, and at 1500 µg/kg or 3000 µg/kg biweekly for an additional period. In another example, the BCMAxCD3 bispecific antibody can be subcutaneously administered at 3000 µg/kg or 300 mg in biweekly intervals for 8 weeks, followed by an additional period of biweekly administration at the same or different dose. In another example, the BCMAxCD3 bispecific antibody can be subcutaneously administered at 3000 µg/kg or 6000 µg/kg biweekly or monthly for 8 weeks. In other embodiments, the BCMAxCD3 bispecific antibody is subcutaneously administered 60 mg, 150 mg or 200 mg weekly, preferably 150 mg weekly, for 8 weeks, followed by subcutaneous administration of 300 mg BCMAxCD3 bispecific antibody biweekly. In other embodiments, the BCMAxCD3 bispecific antibody is subcutaneously administered at 1500 µg/kg weekly for 8 weeks, followed by subcutaneous administration of 3000 µg/kg BCMAxCD3 bispecific antibody biweekly.

According to embodiments of the application, the frequency of the administration of the anti-CD38 antibody can be decreased with the time of the treatment. For example, the anti-CD38 antibody is subcutaneously administered to the subject in the dose of 1800 mg once every week during week 1 to week 8 of the treatment, once every two weeks during week 9 to week 24 of the treatment, and once every four weeks after week 24 of the treatment.

The BCMAxCD3 bispecific antibody and the anti-CD38 antibody can be administered by maintenance therapy, such as, e.g., once a week, 2 weeks, 3 weeks or 4 weeks, for a period of 6 months or more.

The BCMAxCD3 bispecific antibody and the anti-CD38 antibody can also be administered in premalignant settings in order to reduce the risk of developing the cancer, such as the multiple myeloma, delay the onset of the occurrence of an event in cancer progression, and/or reduce the risk of recurrence when the cancer is in remission.

In some embodiments, the BCMAxCD3 bispecific antibody is administered to the subject after the subject has been administered the anti-CD38 antibody. The BCMAxCD3 bispecific antibody and the anti-CD38 antibody can be administered on the same day. The BCMAxCD3 bispecific antibody can also be administered one day, one week, two weeks, three weeks, one month, five weeks, six weeks, seven weeks, two months, three months, four months, five months, six months, or longer after administering the anti-CD38 antibody.

In some embodiments, the method further comprises administering to the subject one or more anti-cancer therapies.

In some embodiments, the one or more anti-cancer therapies is selected from the group consisting of an autologous stem cell transplant (ASCT), radiation, surgery, a chemotherapeutic agent, an immunomodulatory agent and a targeted cancer therapy.

In some embodiments, the one or more anti-cancer therapies is the autologous stem cell transplant (ASCT). In some embodiments, the one or more anti-cancer therapies is radiation. In some embodiments, the one or more anti-cancer therapies is surgery. In some embodiments, the one or more anti-cancer therapies is the chemotherapeutic agent. In some embodiments, the one or more anti-cancer therapies is the immunomodulatory agent. In some embodiments, the one or more anti-cancer therapies is targeted cancer therapy. In some embodiments, the one or more anti-cancer therapies is selected from the group consisting of lenalidomide, thalidomide, pomalidomide, bortezomib, carfilzomib, elotuzumab, ixazomib, melphalan, isatuximab, CELMoDs, dexamethasone, vincristine, cyclophosphamide, hydroxydaunorubicin, prednisone, rituximab, imatinib, dasatinib, nilotinib, bosutinib, ponatinib, bafetinib, saracatinib, tozasertib or danusertib, cytarabine, daunorubicin, idarubicin, mitoxantrone, hydroxyurea, decitabine, cladribine, fludarabine, topotecan, etoposide 6-thioguanine, corticosteroid, methotrexate, 6-mercaptopurine, azacitidine, arsenic trioxide and all-trans retinoic acid, or any combination thereof.

In some embodiments, the one or more anti-cancer therapies is selected from the group consisting of lenalidomide, thalidomide, pomalidomide, bortezomib, carfilzomib, elotuzumab, ixazomib, melphalan, prednisone or dexamethasone, or any combination thereof.

In some embodiments, the one or more anti-cancer therapies is pomalidomide.

In some embodiments, pomalidomide is orally administered at a dose of 2 mg or 4 mg.

In some embodiments, the one or more anti-cancer therapies are pomalidomide and dexamethasone.

In some embodiments, pomalidomide is administered in a delayed dosing schedule. The delayed dosing schedule may occur in cycle 1 day 15 (C1D15) or in cycle 2 day 1 (C2D1).

In some embodiments, pomalidomide is administered concurrently with the BCMAxCD3 bispecific antibody and the anti-CD38 antibody.

In some embodiments, dexamethasone is administered during at least 3 full initial IMiD-containing cycles.

CD38 is a multifunctional protein having function in receptor-mediated adhesion and signaling as well as mediating calcium mobilization via its ecto-enzymatic activity, catalyzing formation of cyclic ADP-ribose (cADPR) and ADPR. CD38 mediates cytokine secretion and activation and proliferation of lymphocytes (Funaro et al., J Immunol 145:2390-6, 1990; Terhorst et al., Cell 771-80, 1981; Guse et al., Nature 398:70-3, 1999). CD38, via its NAD glycohydrolase activity, also regulates extracellular NAD+levels, which have been implicated in modulating the regulatory T-cell compartment (Adriouch et al., Microbes infect 14:1284-92, 2012; Chiarugi et al., Nature Reviews 12:741-52, 2012). In addition to signaling via Ca2+, CD38 signaling occurs via cross-talk with antigen-receptor complexes on T- and B-cells or other types of receptor complexes, e.g., major histocompatibility complex (MHC) molecules, involving CD38 in several cellular responses, but also in switching and secretion of IgG1.

Any suitable anti-CD38 antibody can be used in a method of the application.

In some embodiments, the anti-CD38 antibody comprises the HCDR1 of SEQ ID NO: 8, the HCDR2 of SEQ ID NO: 9, the HCDR3 of SEQ ID NO: 10, the LCDR1 of SEQ ID NO: 11, the LCDR2 of SEQ ID NO: 12 and the LCDR3 of SEQ ID NO: 13.

The CDRs recited above are of the Kabat numbering system. However, as provided for herein, the CDRs of the present disclosure may be provided by any appropriate numbering system, such as Kabat, Chothia, IMGT, or AbM numbering systems. Table 3 provides exemplary CDRs utilizing the Kabat, Chothia, IMGT, and AbM numbering systems:

TABLE 3

Exemplary CDRs of the anti-CD38 antibody

| Region | Kabat | Chothia | AbM | IMGT |
|---|---|---|---|---|
| HCDR1 | SFAMS (SEQ ID NO: 8) | GFTFNSF (SEQ ID NO: 46) | GFTFNSFAMS (SEQ ID NO: 48) | GFTFNSFA (SEQ ID NO: 50) |
| HCDR2 | AISGSGGGT YYADSVKG (SEQ ID NO: 9) | SGSGGG (SEQ ID NO: 47) | AISGSGGGTY (SEQ ID NO: 49) | ISGSGGGT (SEQ ID NO: 51) |
| HCDR3 | DKILWFGEP VFDY (SEQ ID NO: 10) | SEQ ID NO: 10 | SEQ ID NO: 10 | AKDKILWF GEPVFDY (SEQ ID NO: 52) |
| LCDR1 | RASQSVSSY LA (SEQ ID NO: 11) | SEQ ID NO: 11 | SEQ ID NO: 11 | QSVSSY (SEQ ID NO: 53) |
| LCDR2 | DASNRAT (SEQ ID NO: 12) | SEQ ID NO: 12 | SEQ ID NO: 12 | DAS |
| LCDR3 | QQRSNWPPT (SEQ ID NO: 13) | SEQ ID NO: 13 | SEQ ID NO: 13 | SEQ ID NO: 13 |

In some embodiments, the anti-CD38 antibody comprises the HCDR1 of SEQ ID NO: 8, the HCDR2 of SEQ ID NO: 9, the HCDR3 of SEQ ID NO: 10, the LCDR1 of SEQ ID NO: 11, the LCDR2 of SEQ ID NO: 12 and the LCDR3 of SEQ ID NO: 13.

In some embodiments, the anti-CD38 antibody comprises the HCDR1 of SEQ ID NO: 46, the HCDR2 of SEQ ID NO: 47, the HCDR3 of SEQ ID NO: 10, the LCDR1 of SEQ ID NO: 11, the LCDR2 of SEQ ID NO: 12 and the LCDR3 of SEQ ID NO: 13.

In some embodiments, the anti-CD38 antibody comprises the HCDR1 of SEQ ID NO: 48, the HCDR2 of SEQ ID NO: 49, the HCDR3 of SEQ ID NO: 10, the LCDR1 of SEQ ID NO: 11, the LCDR2 of SEQ ID NO: 12 and the LCDR3 of SEQ ID NO: 13.

In some embodiments, the anti-CD38 antibody comprises the HCDR1 of SEQ ID NO: 50, the HCDR2 of SEQ ID NO: 51, the HCDR3 of SEQ ID NO: 52, the LCDR1 of SEQ ID NO: 53, a LCDR2 having the amino acid sequence of DAS, and the LCDR3 of SEQ ID NO: 13.

In some embodiments, the anti-CD38 antibody comprises the VH of SEQ ID NO: 6 and the VL of SEQ ID NO: 7.

In some embodiments, the anti-CD38 antibody comprises the HC of SEQ ID NO: 14 and the LC of SEQ ID NO: 15.

Other anti-CD38 antibodies used in the methods of the invention may be known antibodies, such as mAb003 described in U.S. Pat. No. 7,829,673. The VH and the VL of mAb003 may be expressed as IgG1/κ; mAb024 described in U.S. Pat. No. 7,829,673. The VH and the VL of mAb024 may be expressed as IgG1/κ; MOR-202 (MOR-03087) comprising described in U.S. Pat. No. 8,088,896. The VH and the VL of MOR-202 may be expressed as IgG1/κ; or isatuximab; described in U.S. Pat. No. 8,153,765. The VH and the VL of isatuximab may be expressed as IgG1/κ. In some embodiments, the anti-CD38 antibody comprises a) the VH of SEQ ID NO: 38 and the VL of SEQ ID NO: 39; b) the VH of SEQ ID NO: 40 and the VL of SEQ ID NO: 41; c) the VH of SEQ ID NO: 42 and the VL of SEQ ID NO: 43; or d) the VH of SEQ ID NO: 44 and the VL of SEQ ID NO: 45.

In one embodiment, the anti-CD38 antibody is DARZALEX® (daratumumab).

In some embodiments, daratumumab comprises the VH of SEQ ID NO: 6 and the VL of SEQ ID NO: 7.

In some embodiments, daratumumab comprises the HC of SEQ ID NO: 14 and the LC of SEQ ID NO: 15.

In some embodiments, the anti-CD38 antibody is chimeric, humanized, or human.

In some embodiments, the anti-CD38 antibody is an IgG1, an IgG2, an IgG3, or an IgG4 isotype.

In some embodiments, the anti-CD38 antibody is an IgG1 isotype.

B-cell maturation antigen (BCMA) is a cell membrane bound tumor necrosis factor receptor family member involved in differentiation of B-cells to plasma cells. Expression of BCMA is restricted to the B-cell lineage where it is predominantly expressed in the interfollicular region of germinal centers and on differentiated plasma cells and plasmablasts. BCMA is virtually absent on naive and memory B cells (Tai and Anderson, Immunotherapy 7: 1187-99, 2015). A BCMAxCD3 bispecific antibody targets the CD3 receptor complex on T cells and BCMA on plasma cells. The dual binding sites allow the BCMA x CD3 bispecific antibody to draw CD3+ T cells in close proximity to myeloma cells, without regard to T cell receptor specificity or reliance on MHC Class 1 molecules on the surface of antigen presenting cells for activation, leading to cell death of the BCMA-positive cells.

Any suitable BCMAxCD3 bispecific antibody can be used in a method of the application. Exemplary multispecific and/or bispecific formats include dual targeting molecules include Dual Targeting (DT)-Ig (GSK/Domantis), Two-in-one Antibody (Genentech) and mAb2 (F-Star), Dual Variable Domain (DVD)-Ig (Abbott), Ts2Ab (MedImmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS) and Dual Affinity Retargeting Technology (Fc-DART) (MacroGenics), F(ab)2 (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech), Bispecific T Cell Engager (BITE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies. Various formats of bispecific antibodies have been described, for example in Chames and Baty (2009) Curr Opin Drug Disc Dev 12: 276 and in Nunez-Prado et al., (2015) Drug Discovery Today 20(5):588-594.

In some embodiments, the BCMAxCD3 bispecific antibody and the anti-CD38 antibody are antigen binding fragments. Exemplary antigen binding fragments are Fab, F(ab')2, Fd and Fv fragments.

In some embodiments, the BCMAxCD3 bispecific antibody is chimeric, humanized or human.

In some embodiments, the BCMAxCD3 bispecific antibody comprises a BCMA binding domain comprising a VH having the HCDR1 of SEQ ID NO: 18, the HCDR2 of SEQ ID NO: 19, the HCDR3 of SEQ ID NO: 20, and a VL having the LCDR1 of SEQ ID NO: 21, the LCDR2 of SEQ ID NO: 22 and the LCDR3 of SEQ ID NO: 23, and a CD3 binding domain comprising a VH having the HCDR1 of SEQ ID NO: 28, the HCDR2 of SEQ ID NO: 29, the HCDR3 of SEQ ID NO: 30, and a VL having the LCDR1 of SEQ ID NO: 31, the LCDR2 of SEQ ID NO: 32 and the LCDR3 of SEQ ID NO: 33. The HCDRs and LCDRs of the BCMA x CD3 bispecific antibody are recited in Table 4 below:

TABLE 4

Exemplary CDRs of BCMA x CD3 bispecific antibody

| Binding Arm | Region | Sequence | SEQ ID NO: |
|---|---|---|---|
| BCMA | HCDR1 | SGSYFWG | 18 |
| | HCDR2 | SIYYSGITYYNPSLKS | 19 |
| | HCDR3 | HDGAVAGLFDY | 20 |
| | LCDR1 | GGNNIGSKSVH | 21 |
| | LCDR2 | DDSDRPS | 22 |
| | LCDR3 | QVWDSSSDHVV | 23 |
| CD3 | HCDR1 | TYAMN | 28 |
| | HCDR2 | RIRSKYNNYATYYAASVKG | 29 |
| | HCDR3 | HGNFGNSYVSWFAY | 30 |

TABLE 4-continued

Exemplary CDRs of BCMA x CD3 bispecific antibody

| Binding Arm | Region | Sequence | SEQ ID NO: |
|---|---|---|---|
| | LCDR1 | RSSTGAVTTSNYAN | 31 |
| | LCDR2 | GTNKRAP | 32 |
| | LCDR3 | ALWYSNLWV | 33 |

The CDRs recited in the table above are of the Kabat numbering system. However, as provided for herein, the CDRs of the present disclosure may be provided by any appropriate numbering system, such as any of the Kabat, Chothia, IMGT, or AbM numbering systems. Tables 5-7 below provide exemplary CDRs utilizing the Chothia, AbM, and IMGT numbering systems:

TABLE 5

Exemplary CDRs of BCMA x CD3 bispecific antibody - Chothia numbering system:

| Binding Arm | Region | Sequence | SEQ ID NO: |
|---|---|---|---|
| BCMA | HCDR1 | GGSISSGSY | 54 |
| | HCDR2 | YYSGI | 55 |
| | HCDR3 | HDGAVAGLFDY | 20 |
| | LCDR1 | GGNNIGSKSVH | 21 |
| | LCDR2 | DDSDRPS | 22 |
| | LCDR3 | QVWDSSSDHVV | 23 |
| CD3 | HCDR1 | GFTFNTY | 56 |
| | HCDR2 | RSKYNNYA | 57 |
| | HCDR3 | HGNFGNSYVSWFAY | 30 |
| | LCDR1 | RSSTGAVTTSNYAN | 31 |
| | LCDR2 | GTNKRAP | 32 |
| | LCDR3 | ALWYSNLWV | 33 |

TABLE 6

Exemplary CDRs of BCMA x CD3 bispecific antibody - AbM numbering system:

| Binding Arm | Region | Sequence | SEQ ID NO: |
|---|---|---|---|
| BCMA | HCDR1 | GGSISSGSYFWG | 58 |
| | HCDR2 | SIYYSGITY | 59 |
| | HCDR3 | HDGAVAGLFDY | 20 |
| | LCDR1 | GGNNIGSKSVH | 21 |
| | LCDR2 | DDSDRPS | 22 |
| | LCDR3 | QVWDSSSDHVV | 23 |

TABLE 6-continued

Exemplary CDRs of BCMA x CD3 bispecific antibody - AbM numbering system:

| Binding Arm | Region | Sequence | SEQ ID NO: |
|---|---|---|---|
| CD3 | HCDR1 | GFTFNTYAMN | 60 |
| | HCDR2 | RIRSKYNNYATY | 61 |
| | HCDR3 | HGNFGNSYVSWFAY | 30 |
| | LCDR1 | RSSTGAVTTSNYAN | 31 |
| | LCDR2 | GTNKRAP | 32 |
| | LCDR3 | ALWYSNLWV | 33 |

TABLE 7

Exemplary CDRs of BCMA x CD3 bispecific antibody - IMGT numbering system:

| Binding Arm | Region | Sequence | SEQ ID NO: |
|---|---|---|---|
| CBMA | HCDR1 | GGSISSGSYF | 62 |
| | HCDR2 | IYYSGIT | 63 |
| | HCDR3 | ARHDGAVAGLFDY | 64 |
| | LCDR1 | NIGSKS | 65 |
| | LCDR2 | DDS | NA |
| | LCDR3 | QVWDSSSDHVV | 23 |
| CD3 | HCDR1 | GFTFNTYA | 66 |
| | HCDR2 | IRSKYNNYAT | 67 |
| | HCDR3 | ARHGNFGNSYVSWFAY | 68 |
| | LCDR1 | TGAVTTSNY | 69 |
| | LCDR2 | GTN | NA |
| | LCDR3 | ALWYSNLWV | 33 |

In some embodiments, the BCMAxCD3 bispecific antibody comprises a BCMA binding domain comprising a VH having the HCDR1 of SEQ ID NO: 18, the HCDR2 of SEQ ID NO: 19, the HCDR3 of SEQ ID NO: 20, and a VL having the LCDR1 of SEQ ID NO: 21, the LCDR2 of SEQ ID NO: 22 and the LCDR3 of SEQ ID NO: 23, and a CD3 binding domain comprising a VH having the HCDR1 of SEQ ID NO: 28, the HCDR2 of SEQ ID NO: 29, the HCDR3 of SEQ ID NO: 30, and a VL having the LCDR1 of SEQ ID NO: 31, the LCDR2 of SEQ ID NO: 32 and the LCDR3 of SEQ ID NO: 33.

In some embodiments, the BCMAxCD3 bispecific antibody comprises a BCMA binding domain comprising a VH having the HCDR1 of SEQ ID NO: 54, the HCDR2 of SEQ ID NO: 55, the HCDR3 of SEQ ID NO: 20, and a VL having the LCDR1 of SEQ ID NO: 21, the LCDR2 of SEQ ID NO: 22 and the LCDR3 of SEQ ID NO: 23, and a CD3 binding domain comprising a VH having the HCDR1 of SEQ ID NO: 56, the HCDR2 of SEQ ID NO: 57, the HCDR3 of SEQ ID NO: 30, and a VL having the LCDR1 of SEQ ID NO: 31, the LCDR2 of SEQ ID NO: 32 and the LCDR3 of SEQ ID NO: 33.

In some embodiments, the BCMAxCD3 bispecific antibody comprises a BCMA binding domain comprising a VH having the HCDR1 of SEQ ID NO: 58, the HCDR2 of SEQ ID NO: 59, the HCDR3 of SEQ ID NO: 20, and a VL having the LCDR1 of SEQ ID NO: 21, the LCDR2 of SEQ ID NO: 22 and the LCDR3 of SEQ ID NO: 23, and a CD3 binding domain comprising a VH having the HCDR1 of SEQ ID NO: 60, the HCDR2 of SEQ ID NO: 61, the HCDR3 of SEQ ID NO: 30, and a VL having the LCDR1 of SEQ ID NO: 31, the LCDR2 of SEQ ID NO: 32 and the LCDR3 of SEQ ID NO: 33.

In some embodiments, the BCMAxCD3 bispecific antibody comprises a BCMA binding domain comprising a VH having the HCDR1 of SEQ ID NO: 62, the HCDR2 of SEQ ID NO: 63, the HCDR3 of SEQ ID NO: 64, and a VL having the LCDR1 of SEQ ID NO: 65, a LCDR2 having the amino acid sequence of DDS, and the LCDR3 of SEQ ID NO: 23, and a CD3 binding domain comprising a VH having the HCDR1 of SEQ ID NO: 66, the HCDR2 of SEQ ID NO: 67, the HCDR3 of SEQ ID NO: 68, and a VL having the LCDR1 of SEQ ID NO: 69, a LCDR2 having the amino acid sequence of GTN, and the LCDR3 of SEQ ID NO: 33.

In some embodiments, the BCMAxCD3 bispecific antibody comprises a BCMA binding domain comprising the VH of SEQ ID NO: 24 and the VL of SEQ ID NO: 25, and a CD3 binding domain comprising the VH of SEQ ID NO: 34 and the VL of SEQ ID NO: 35.

In some embodiments, the BCMAxCD3 bispecific antibody that binds BCMA comprises a first heavy chain (HC1I) of SEQ ID NO: 26, a first light chain (LC1I) of SEQ ID NO: 27, a second heavy chain (HC2) of SEQ ID NO: 36, and a second light chain (LC2) of SEQ ID NO: 37.

In some embodiments, the BCMA binding arm of the BCMA x CD3 bispecific antibody and the CD3 binding arm of the BCMA x CD3 bispecific antibody comprise the amino acid sequences as provided for in Tables 8a and 8b TABLE 8a Sequences of the BCMA binding arm of a BCMA x CD3 bispecific antibody.

| | Region | Sequence | SEQ ID NO: |
|---|---|---|---|
| BCMB69 | HCDR1 | SGSYFWG | 18 |
| | HCDR2 | SIYYSGITYYNPSLKS | 19 |
| | HCDR3 | HDGAVAGLFDY | 20 |
| | LCDR1 | GGNNIGSKSVH | 21 |
| | LCDR2 | DDSDRPS | 22 |
| | LCDR3 | QVWDSSSDHVV | 23 |
| | VH | QLQLQESGPGLVKPSETLSLTCTVSGGSISSGS YFWGWIRQPPGKGLEWIGSIYYSGITYYNPSLK SRVTISVDTSKNQFSLKLSSVTAADTAVYYCAR HDGAVAGLFDYWGQGTLVTSS | 24 |
| | VL | SYVLTQPPSVSVAPGQTARITCGGNNIGSKSVH WYQQPPGQAPVVVVYDDSDRPSGIPERFSGSN SGNTATLTISRVEAGDEAVYYCQVWDSSSDHV VFGGGTKLTVLGQP | 25 |

TABLE 8a-continued

Sequences of the BCMA binding arm of a BCMA x CD3 bispecific antibody.

| Region | Sequence | SEQ ID NO: |
|---|---|---|
| HC | QLQLQESGPGLVKPSETLSLTCTVSGGSISSGS YFWGWIRQPPGKGLEWIGSIYYSGITYYNPSLK SRVTISVDTSKNQFSLKLSSVTAADTAVYYCAR HDGAVAGLFDYWGQGTLVTVSSASTKGPSVFP LAPCSRSTSESTAALGCLVKDYFPEPVTVSWNS GALTSGVHTFPAVLQSSGLYSLSSVVTVPSSSL GTKTYTCNVDHKPSNTKVDKRVESKYGPPCPP CPAPEAAGGPSVFLFPPKPKDTLMISRTPEVTC VVVDVSQEDPEVQFNWYVDGVEVHNAKTKPRE EQFNSTYRVVSVLTVLHQDWLNGKEYKCKVS NKGLPSSIEKTISKAKGQPREPQVYTLPPSQEE MTKNQVSLTCLVKGFYPSDIAVEWESNGQPENN YKTTPPVLDSDGSFFLYSRLTVDKSRWQEGNV FSCSVMHEALHNHYTQKSLSLSLGK | 26 |
| LC | SYVLTQPPSVSVAPGQTARITCGGNNIGSKSVH WYQQPPGQAPVVVVYDDSDRPSGIPERFSGSN SGNTATLTISRVEAGDEAVYYCQVWDSSSDHV VFGGGTKLTVLGQPKAAPSVTLFPPSSPVKLQA NKATLVCLISDFYPGAVTVAWKGDSSPVKAGVE TTTPSKQSNNKYAASSYLSLTPEQWKSHRSYSC QVTHEGSTVEKTVAPTECS | 27 |

TABLE 8b

Sequences of the CD3 binding arm of a BCMA x CD3 bispecific antibody.

| Region | Sequence | SEQ ID NO: |
|---|---|---|
| CD3B219 | HCDR1 TYAMN | 28 |
| | HCDR2 RIRSKYNNYATYYAASVKG | 29 |
| | HCDR3 HGNFGNSYVSWFAY | 30 |
| | LCDR1 RSSTGAVTTSNYAN | 31 |
| | LCDR2 GTNKRAP | 32 |
| | LCDR3 ALWYSNLWV | 33 |
| | VH EVQLVESGGGLVQPGGSLRLSCAASGFTFNT YAMNWVRQAPGKGLEWVARIRSKYNNYAT YYAASVKGRFTISRDDSKNSLYLQMNSLKTE DTAVYYCARHGNFGNSYVSWFAYWGQGTL VTVSS | 34 |
| | VL QTVVTQEPSLTVSPGGTVTLTCRSSTGAVTT SNYANWVQQKPGQAPRGLIGGTNKRAPGTP ARFSGSLLGGKAALTLSGVQPEDEAEYYCAL WYSNLWVFGGGTKLTVLGQP | 35 |
| | HC EVQLVESGGGLVQPGGSLRLSCAASGFTFNT YAMNWVRQAPGKGLEWVARIRSKYNNYAT YYAASVKGRFTISRDDSKNSLYLQMNSLKTE DTAVYYCARHGNFGNSYVSWFAYWGQGTL VTVSSASTKGPSVFPLAPCSRSTSESTAALGC LVKDYFPEPVTVSWNSGALTSGVHTFPAVL QSSGLYSLSSVVTVPSSSLGTKTYTCNVDHK PSNTKVDKRVESKYGPPCPPCPAPEAAGGPS VFLFPPKPKDTLMISRTPEVTCVVVDVSQED PEVQFNWYVDGVEVHNAKTKPREEQFNSTY RVVSVLTVLHQDWLNGKEYKCKVSNKGLPS SIEKTISKAKGQPREPQVYTLPPSQEEMTKNQ VSLTCLVKGFYPSDIAVEWESNGQPENNYKT TPPVLDSDGSFLLYSKLTVDKSRWQEGNVFS CSVMHEALHNHYTQKSLSLSLGK | 36 |
| | LC QTVVTQEPSLTVSPGGTVTLTCRSSTGAVTT SNYANWVQQKPGQAPRGLIGGTNKRAPGTP ARFSGSLLGGKAALTLSGVQPEDEAEYYCAL WYSNLWVFGGGTKLTVLGQPKAAPSVTLFP PSSEELQANKATLVCLISDFYPGAVTVAWKA DSSPVKAGVETTTPSKQSNNKYAASSYLSLT PEQWKSHRSYSCQVTHEGSTVEKTVAPTECS | 37 |

In some embodiments, the BCMAxCD3 bispecific antibody comprises a BCMA binding domain that binds BCMA selected from the group consisting of the BCMA binding domain of ACTR cancer therapy by Seattle Genetics, AFM-26, ALLO-715, anti-BCMA allogenic CAR-T cell therapy by CRISPR Therapeutics, anti-BCMA CAR-T therapy by Sorrento Therapeutics, anti-CD19/BCMA CAR-T cell therapy by Hrain Biotechnology, BCMA CAR-T therapy by Chineo Med (Beijing), BCMA TAC-T cell therapy by Triumvira Immunologics, BCMA-CAR T cell therapy by Shanghai Unicar-Therapy Biomed, BCMA/CD3 antibody by Regeneron, CAR-NK cell therapies by NantKwest, CC-93629, CMD-505, CTX-4419, CYAD-211, HDP-101, HPN-217, P-BCMA-ALLO1, TNB-383B, bb-2121, AUTO-2, BCMA chimeric antigen receptor therapy by Pregene, BCMA-CAR T cells by Shanghai Bioray Laboratory, BCMA-CAR-T cells by CARsgen Therapeutics, CAR-T/TCR-T cell immunotherapy by Shenzhen BinDeBio, ET-140, P-BCMA-101, REGN-5458, AMG-701, anti BCMA CAR-T cell therapy by Cellular Biomedicine Group, bb-21217, BI-836909, CC-93269, Descartes-08, IM-21, JNJ-64007957, MEDI-2228 or PF-06863135.

In some embodiments, the BCMAxCD3 bispecific antibody can be, but is not limited to, elranatamab (also named PF-06863135), teneobio (also named TNB-383B), REGN5458, REGN5459, pavurutamab (also named AMG-701), BI 836909, CC-93269, WVT078 or teclistamab (also named JNJ-957 or JNJ-64007957).

In some embodiments, teclistamab comprises a first heavy chain (HC1), a first light chain (LC1), a second heavy chain (HC2), and a second light chain (LC2), wherein the HC1 is associated with LC1 and the HC2 is associated with LC2, wherein HC1 and LC1 form a first antigen-binding site that immunospecifically binds to BCMA and wherein HC2 and LC2 form a second antigen-binding site that immunospecifically binds to CD3. In some embodiments, teclistamab comprises a HC1 of SEQ ID NO: 26, a LC1 of SEQ ID NO: 27, a HC2 of SEQ ID NO: 36, and a LC2 of SEQ ID NO: 37. In some embodiments, the BCMA arm and the CD3 arm of teclistamab form a functional bispecific antibody through an interaction between their respective Fc domains.

In some embodiments, the BCMAxCD3 bispecific antibody comprises any one of the BCMA binding domains described in Int. Pat. Publ. No. WO2017/031104.

In some embodiments, the BCMAxCD3 bispecific antibody is an IgG1, an IgG2, an IgG3, or an IgG4 isotype.

In some embodiments, the BCMAxCD3 bispecific antibody is an IgG1 isotype.

In some embodiments, the BCMAxCD3 bispecific antibody is an IgG2 isotype.

In some embodiments, the BCMAxCD3 bispecific antibody is an IgG3 isotype.

In some embodiments, the BCMAxCD3 bispecific antibody is an IgG4 isotype.

The BCMAxCD3 bispecific antibody can be of any allotype. It is expected that allotype has no influence on properties of the BCMAxCD3 bispecific antibodies, such as binding or Fc-mediated effector functions. Immunogenicity of therapeutic antibodies is associated with increased risk of infusion reactions and decreased duration of therapeutic response (Baert et al., (2003) N Engl J Med 348:602-08). The extent to which therapeutic antibodies induce an immune response in the host may be determined in part by the allotype of the antibody (Stickler et al., (2011) Genes and Immunity 12:213-21). Antibody allotype is related to amino acid sequence variations at specific locations in the constant region sequences of the antibody. Table 9 shows select IgG1, IgG2, and IgG4 allotypes.

TABLE 9

IgG1, IgG2 and IgG4 allotypes.

Amino acid residue at position of diversity (residue numbering: EU Index)

| | IgG2 | | IgG4 | | IgG1 | | | |
|---|---|---|---|---|---|---|---|---|
| Allotype | 189 | 282 | 309 | 422 | 214 | 356 | 358 | 431 |
| G2m(n) | T | M | | | | | | |
| G2m(n−) | P | V | | | | | | |
| G2m(n)/(n− nG4m(a) | T | V | L | R | | | | |
| G1m(17) | | | | | K | E | M | A |
| G1m(17, 1) | | | | | K | D | L | A |

In some embodiments, the multispecific antibody comprises one or more Fc substitutions that reduces binding of the multispecific antibody to a Fcγ receptor (FcγR). Substitutions that reduce binding of the multispecific antibody to the FcγR reduces the Fc effector functions such as ADCC, ADCP and/or CDC of the multispecific antibody. The specific substitutions can be made in comparison to the wild-type IgG1 of SEQ ID NO: 16 or the wild-type IgG4 of SEQ ID NO: 17.

In some embodiments, the one or more Fc substitutions is selected from the group consisting of F234A/L235A on IgG4, L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4 and S228P/F234A/L235A/G236-deleted/G237A/P238S on IgG4, wherein residue numbering is according to the EU index.

In some embodiments, the one or more Fc substitutions is F234A/L235A on IgG4.

In some embodiments, the one or more Fc substitutions is L234A/L235A on IgG1.

In some embodiments, the one or more Fc substitutions is V234A/G237A/P238S/H268A/V309L/A330S/P331S on IgG2.

In some embodiments, the one or more Fc substitutions is F234A/L235A on IgG4.

In some embodiments, the one or more Fc substitutions is S228P/F234A/L235A on IgG4.

In some embodiments, the one or more Fc substitutions is N297A on all Ig isotypes.

In some embodiments, the one or more Fc substitutions is V234A/G237A on IgG2.

In some embodiments, the one or more Fc substitutions is K214T/E233P/L234V/L235A/G236-deleted/A327G/P331A/D365E/L358M on IgG1.

In some embodiments, the one or more Fc substitutions is H268Q/V309L/A330S/P331S on IgG2.

In some embodiments, the one or more Fc substitutions is S267E/L328F on IgG1. In some embodiments, the one or more Fc substitutions is L234F/L235E/D265A on IgG1.

In some embodiments, the one or more Fc substitutions is L234A/L235A/G237A/P238S/H268A/A330S/P331S on IgG1.

In some embodiments, the one or more Fc substitutions is S228P/F234A/L235A/G237A/P238S on IgG4 and S228P/F234A/L235A/G236-deleted/G237A/P238S on IgG4.

In some embodiments, the multispecific antibody further comprises a S228P substitution.

In some embodiments, the multispecific antibody comprises one or more asymmetric substitutions in a first CH3 domain or in a second CH3 domain, or in both the first CH3 domain and the second CH3 domain.

In some embodiments, the one or more asymmetric substitutions is selected from the group consisting of F450L/K409R, wild-type/F409L_R409K, T366Y/F405A, T366W/F405W, F405W/Y407A, T394W/Y407T, T394S/Y407A, T366W/T394S, F405W/T394S and T366W/T366S_L368A_Y407V, L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F and T350V_L351Y_F405A_Y407V/T350V_T366L_K392L_T394W.

In some embodiments, the one or more asymmetric substitutions is F450L/K409R. In some embodiments, the one or more asymmetric substitutions is wild-type/F409L_R409K. In some embodiments, the one or more asymmetric substitutions is T366Y/F405A. In some embodiments, the one or more asymmetric substitutions is T366W/F405W. In some embodiments, the one or more asymmetric substitutions is F405W/Y407A. In some embodiments, the one or more asymmetric substitutions is T394W/Y407T. In some embodiments, the one or more asymmetric substitutions is T394S/Y407A. In some embodiments, the one or more asymmetric substitutions is T366W/T394S. In some embodiments, the one or more asymmetric substitutions is F405W/T394S. In some embodiments, the one or more asymmetric substitutions is T366W/T366S_L368A_Y407V. In some embodiments, the one or more asymmetric substitutions is L351Y_F405A_Y407V/T394W. In some embodiments, the one or more asymmetric substitutions is T366I_K392M_T394W/F405A_Y407V. In some embodiments, the one or more asymmetric substitutions is T366L_K392M_T394W/F405A_Y407V. In some embodiments, the one or more asymmetric substitutions is L351Y_Y407A/T366A_K409F. In some embodiments, the one or more asymmetric substitutions is L351Y_Y407A/T366V_K409F. In some embodiments, the one or more asymmetric substitutions is Y407A/T366A_K409F. In some embodiments, the one or more asymmetric substitutions is T350V_L351Y_F405A_Y407V/T350V_T366L_K392L_T394W.

In some embodiments, the BCMAxCD3 bispecific antibody is an IgG4 isotype and comprises phenylalanine at position 405 and arginine at position 409 in a first heavy chain (HC1) and leucine at position 405 and lysine at position 409 in a second heavy chain (HC2), wherein residue numbering is according to the EU Index.

In some embodiments, the BCMAxCD3 bispecific antibody further comprises proline at position 228, alanine at position 234 and alanine at position 235 in both the HC1 and the HC2.

In some embodiments, the cancer is a hematological malignancy or a solid tumor.

In some embodiments, the hematological malignancy is a multiple myeloma, a smoldering multiple myeloma, a monoclonal gammopathy of undetermined significance (MGUS), an acute lymphoblastic leukemia (ALL), a diffuse large B-cell lymphoma (DLBCL), a Burkitt's lymphoma (BL), a follicular lymphoma (FL), a mantle-cell lymphoma (MCL), Waldenstrom's macroglobulinema, a plasma cell leukemia, a light chain amyloidosis (AL), a precursor B-cell lymphoblastic leukemia, a precursor B-cell lymphoblastic leukemia, an acute myeloid leukemia (AML), a myelodysplastic syndrome (MDS), a chronic lymphocytic leukemia (CLL), a B cell malignancy, a chronic myeloid leukemia (CML), a hairy cell leukemia (HCL), a blastic plasmacytoid dendritic cell neoplasm, Hodgkin's lymphoma, non-Hodgkin's lymphoma, a marginal zone B-cell lymphoma (MZL), a mucosa-associated lymphatic tissue lymphoma (MALT), plasma cell leukemia, anaplastic large-cell lymphoma (ALCL), leukemia or lymphoma.

In some embodiments, the hematological malignancy is multiple myeloma. In some embodiments, the multiple myeloma is a newly diagnosed multiple myeloma. In some embodiments, the multiple myeloma is a relapsed or a refractory multiple myeloma (RRMM).

In some embodiments, the multiple myeloma is a high-risk multiple myeloma. Subjects with high-risk multiple myeloma are known to relapse early and have poor prognosis and outcome. Subjects can be classified as having high-risk multiple myeloma is they have one or more of the following cytogenetic abnormalities: t(4;14)(p16;q32), t(14;16)(q32;q23), del17p, 1qAmp, t(4;14)(p16;q32) and t(14;16)(q32;q23), t(4;14)(p16;q32) and del17p, t(14;16)(q32;q23) and del17p, ort(4;14)(p16;q32), t(14;16)(q32;q23) and del17p.

In some embodiments, the subject having the high-risk multiple myeloma has one or more chromosomal abnormalities comprising: t(4;14)(p16;q32), t(14;16)(q32;q23), del17p, 1qAmp, t(4;14)(p16;q32) and t(14;16)(q32;q23), t(4;14)(p16;q32) and del17p, t(14;16)(q32;q23) and del17p; or t(4;14)(p16;q32), t(14;16)(q32;q23) and del17p, or any combination thereof.

Various qualitative and/or quantitative methods can be used to determine relapse or refractory nature of the disease. Symptoms that can be associated are for example a decline or plateau of the well-being of the patient or re-establishment or worsening of various symptoms associated with solid tumors, and/or the spread of cancerous cells in the body from one location to other organs, tissues or cells.

The cytogenetic abnormalities can be detected for example by fluorescent in situ hybridization (FISH). In chromosomal translocations, an oncogene is translocated to the IgH region on chromosome 14q32, resulting in dysregulation of these genes. t(4;14)(p16;q32) involves translocation of fibroblast growth factor receptor 3 (FGFR3) and multiple myeloma SET domain containing protein (MM-SET) (also called WHSC1/NSD2), and t(14;16)(q32;q23) involves translocation of the MAF transcription factor C-MAF. Deletion of 17p (del17p) involves loss of the p53 gene locus.

In some embodiments, the multiple myeloma is relapsed or refractory to treatment with the anti-CD38 antibody, lenalidomide, bortezomib, pomalidomide, carfilzomib, elotuzumab, ixazomib, melphalan or thalidomide, or any combination thereof.

In some embodiments, the multiple myeloma is relapsed or refractory to treatment with the anti-CD38 antibody. In some embodiments, the multiple myeloma is relapsed or refractory to treatment with lenalidomide. In some embodiments, the multiple myeloma is relapsed or refractory to treatment with bortezomib. In some embodiments, the multiple myeloma is relapsed or refractory to treatment with pomalidomide. In some embodiments, the multiple myeloma is relapsed or refractory to treatment with carfilzomib. In some embodiments, the multiple myeloma is relapsed or refractory to treatment with elotuzumab. In some embodiments, the multiple myeloma is relapsed or refractory to treatment with ixazomib. In some embodiments, the multiple myeloma is relapsed or refractory to treatment with melphalan. In some embodiments, the multiple myeloma is relapsed or refractory to treatment with or thalidomide.

In some embodiments, the hematological malignancy is the AML.

In some embodiments, the AML is AML with at least one genetic abnormality. In some embodiments, the AML is AML with multilineage dysplasia. In some embodiments, the AML is therapy-related AML. In some embodiments, the AML is undifferentiated AML. In some embodiments, the AML is AML with minimal maturation. In some embodiments, the AML is AML with maturation. In some embodiments, the AML is acute myelomonocytic leukemia. In some embodiments, the AML is acute monocytic leukemia. In some embodiments, the AML is acute erythroid leukemia. In some embodiments, the AML is acute megakaryoblastic leukemia. In some embodiments, the AML is acute basophilic leukemia. In some embodiments, the AML is acute panmyelosis with fibrosis. In some embodiments, the AML is myeloid sarcoma.

In some embodiments, the at least one genetic abnormality is a translocation between chromosomes 8 and 21, a translocation or an inversion in chromosome 16, a translocation between chromosomes 15 and 17, changes in chromosome 11, or mutation in fms-related tyrosine kinase 3 (FLT3), nucleophosmin (NPM1), isocitrate dehydrogenase 1(IDH1), isocitrate dehydrogenase 2 (IDH2), DNA (cytosine-5)-methyltransferase 3 (DNMT3A), CCAAT/enhancer binding protein alpha (CEBPA), U2 small nuclear RNA auxiliary factor 1(U2AF1), enhancer of zeste 2 polycomb repressive complex 2 subunit (EZH2), structural maintenance of chromosomes TA (SMC1A) or structural maintenance of chromosomes 3 (SMC3).

In some embodiments, the at least one genetic abnormality is the translocation between chromosomes 8 and 21. In some embodiments, the at least one genetic abnormality is the translocation or an inversion in chromosome 16. In some embodiments, the at least one genetic abnormality is the translocation between chromosomes 15 and 17. In some embodiments, the at least one genetic abnormality is changes in chromosome 11. In some embodiments, the at least one genetic abnormality is the mutation in fms-related tyrosine kinase 3 (FLT3). In some embodiments, the at least one genetic abnormality is the mutation in nucleophosmin (NPM1). In some embodiments, the at least one genetic abnormality is the mutation in isocitrate dehydrogenase 1(IDH1). In some embodiments, the at least one genetic abnormality is the mutation in isocitrate dehydrogenase 2 (IDH2). In some embodiments, the at least one genetic abnormality is the mutation in DNA (cytosine-5)-methyl-transferase 3 (DNMT3A). In some embodiments, the at least one genetic abnormality is the mutation in CCAAT/enhancer binding protein alpha (CEBPA). In some embodiments, the at least one genetic abnormality is the mutation in U2 small nuclear RNA auxiliary factor 1(U2AF1). In some embodiments, the at least one genetic abnormality is the mutation in enhancer of zeste 2 polycomb repressive complex 2 subunit (EZH2). In some embodiments, the at least one genetic abnormality is the mutation in structural maintenance of chromosomes TA (SMC1A). In some embodiments, the at least one genetic abnormality is the mutation in structural maintenance of chromosomes 3 (SMC3).

In some embodiments, the at least one genetic abnormality is a translocation t(8; 21)(q22; q22), an inversion inv (16)(p13; q22), a translocation t(16; 16)(p13; q22), a translocation t(15; 17)(q22; q12), a mutation FLT3-ITD, mutations R132H or R100Q/R104V/F108L/R119Q/1130V in IDH1 or mutations R140Q or R172 in IDH2.

In some embodiments, the at least one genetic abnormality is the translocation t(8; 21)(q22; q22). In some embodiments, the at least one genetic abnormality is the inversion inv(16)(p13; q22). In some embodiments, the at least one genetic abnormality is the translocation t(16; 16)(p13; q22). In some embodiments, the at least one genetic abnormality is the translocation t(15; 17)(q22; q12). In some embodiments, the at least one genetic abnormality is the mutation FLT3-ITD. In some embodiments, the at least one genetic abnormality is the mutation R132H in IDH1. In some embodiments, the at least one genetic abnormality is the mutation R100Q/R104V/F108L/R119Q/I130V in IDH1. In some embodiments, the at least one genetic abnormality is the mutation R140Q in IDH2. In some embodiments, the at least one genetic abnormality is the mutation R172 in IDH2.

In some embodiments, the hematological malignancy is the ALL.

In some embodiments, the ALL is B-cell lineage ALL, T-cell lineage ALL, adult ALL or pediatric ALL.

In some embodiments, the ALL is B-cell lineage ALL. In some embodiments, the ALL is T-cell lineage ALL. In some embodiments, the ALL is adult ALL. In some embodiments, the ALL is pediatric ALL.

In some embodiments, the subject with ALL has a Philadelphia chromosome or is resistant or has acquired resistance to treatment with a BCR-ABL kinase inhibitor.

In some embodiments, the subject with ALL has the Philadelphia chromosome. In some embodiments, the subject with ALL is resistant or has acquired resistance to treatment with a BCR-ABL kinase inhibitor.

The Ph chromosome is present in about 20% of adults with ALL and a small percentage of children with ALL and is associated with poor prognosis. At a time of relapse, patients with Ph+ positive ALL may be on tyrosine kinase inhibitor (TKI) regimen and may have therefore become resistant to the TKI. The anti-CD38 antibodies may thus be administered to a subject who has become resistant to selective or partially selective BCR-ABL inhibitors. Exemplary BCR-ABL inhibitors are for example imatinib, dasatinib, nilotinib, bosutinib, ponatinib, bafetinib, saracatinib, tozasertib or danusertib.

Other chromosamal rearrangements identified in B-lineage ALL patients are t(v;11q23) (MLL rearranged), t(1;19) (q23;p13.3); TCF3-PBX1 (E2A-PBX1), t(12;21)(p13;q22); ETV6-RUNX1 (TEL-AML1) and t(5;14)(q31;q32); IL3-IGH.

In some embodiments, the subject has ALL with t(v; 11q23) (MLL rearranged), t(1;19)(q23;p13.3); TCF3-PBX1 (E2A-PBX1), t(12;21)(p13;q22); ETV6-RUNX1 (TEL-AML1) or t(5;14)(q31;q32); IL3-IGH chromosomal rearrangement.

Chromosomal rearrangements can be identified using well known methods, for example fluorescent in situ hybridization, karyotyping, pulsed field gel electrophoresis, or sequencing.

In some embodiments, the hematological malignancy is the smoldering multiple myeloma. In some embodiments, the hematological malignancy is the MGUS. In some embodiments, the hematological malignancy is the ALL. In some embodiments, the hematological malignancy is the DLBLC. In some embodiments, the hematological malignancy is the BL. In some embodiments, the hematological malignancy is the FL. In some embodiments, the hematological malignancy is the MCL. In some embodiments, the hematological malignancy is Waldenstrom's macroglobulinema. In some embodiments, the hematological malignancy is the plasma cell leukemia. In some embodiments, the hematological malignancy is the AL. In some embodiments, the hematological malignancy is the precursor B-cell lymphoblastic leukemia. In some embodiments, the hematological malignancy is the precursor B-cell lymphoblastic leukemia. In some embodiments, the hematological malignancy is the myelodysplastic syndrome (MDS). In some embodiments, the hematological malignancy is the CLL. In some embodiments, the hematological malignancy is the B cell malignancy. In some embodiments, the hematological malignancy is the CML. In some embodiments, the hematological malignancy is the HCL. In some embodiments, the hematological malignancy is the blastic plasmacytoid dendritic cell neoplasm. In some embodiments, the hematological malignancy is Hodgkin's lymphoma. In some embodiments, the hematological malignancy is non-Hodgkin's lymphoma. In some embodiments, the hematological malignancy is the MZL. In some embodiments, the hematological malignancy is the MALT. In some embodiments, the hematological malignancy is the plasma cell leukemia. In some embodiments, the hematological malignancy is the ALCL. In some embodiments, the hematological malignancy is leukemia. In some embodiments, the hematological malignancy is lymphoma.

In one embodiment, the disclosure provides a method of treating a cancer in a subject, comprising administering a therapeutically effective amount of a BCMAxCD3 bispecific antibody to the subject to treat the cancer, wherein the subject has been treated with an anti-CD38 antibody prior to administering the BCMAxCD3 bispecific antibody.

The disclosure also provides a method of treating a cancer in a subject, comprising administering a therapeutically effective amount of a BCMAxCD3 bispecific antibody to the subject to treat the cancer, wherein the subject is relapsed or refractory to treatment with a prior anti-cancer therapeutic.

In some embodiments, the subject administered the BCMAxCD3 antibody is resistant and/or refractory to treatment with the anti-CD38 antibody.

In some embodiments, the cancer is a BCMA expressing cancer.

In some embodiments, the cancer is a hematologic malignancy.

In some embodiments, the cancer is a multiple myeloma, a smoldering myeloma, a monoclonal gammopathy of undetermined significance (MGUS), a B-cell acute lymphoblastic leukemia, a diffuse large B-cell lymphoma, a Burkitt's lymphoma, a follicular lymphoma, a mantle-cell lymphoma, Waldenstrom's macroglobulinema, plasma cell leukemia, light chain amyloidosis or non-Hodgkin's lymphoma. An experienced physician makes the cancer diagnosis.

In some embodiments, the subject is relapsed or refractory to treatment with the anti-CD38 antibody or lenalidomide, or a combination thereof.

In some embodiments, the subject is relapsed or refractory to treatment with the anti-CD38 antibody. In some embodiments, the subject is relapsed or refractory to treatment with lenalidomide.

In some embodiments, the subject is relapsed or refractory to treatment with a prior anti-cancer therapeutic, such as a therapeutic used to treat multiple myeloma or other hematological malignancies.

In some embodiments, the subject is refractory or relapsed to treatment with THALOMID® (thalidomide), REVLIMID® (lenalidomide), POMALYST® (pomalidomide), VELCADE® (bortezomib), NINLARO (ixazomib), KYPROLIS® (carfilzomib), FARADYK® (panobinostat), AREDIA® (pamidronate), ZOMETA® (zoledronic acid), DARZALEX® (daratumumab), elotuzumab (Empliciti®) SARCLISA® (isatuximab), or melphalan (Alkeran®).

In some embodiments, the subject is relapsed to treatment with DARZALEX® (daratumumab).

In some embodiments, the anti-CD38 antibody is administered or provided for administration in a pharmaceutical composition comprising between about 20 mg/mL to about 120 mg/mL of the anti-CD38 antibody in about 25 mM acetic acid, about 60 mM sodium chloride, about 140 mannitol and about 0.04% w/v polysorbate-20 (PS-20); at pH about 5.5.

In some embodiments, the anti-CD38 antibody is administered or provided for administration in a pharmaceutical composition comprising about 1,800 mg of the anti-CD38 antibody and about 30,000 U of rHuPH20.

In some embodiments, the anti-CD38 antibody is administered or provided for administration in a pharmaceutical composition comprising about 120 mg/mL of the anti-CD38 antibody and about 2,000 U/mL of rHuPH20.

In some embodiments, the anti-CD38 antibody is administered or provided for administration in a pharmaceutical composition comprising
about 5 mM and about 15 mM histidine;
about 100 mM and about 300 mM sorbitol;
about 0.01% w/v and about 0.04% w/v PS-20; and
about 1 mg/mL and about 2 mg/mL methionine, at a pH of about 5.5-5.6.

In some embodiments, the anti-CD38 antibody is administered or provided for administration in a pharmaceutical composition comprising about 1,800 mg of the anti-CD38 antibody;
about 30,000 U of rHuPH20;
about 10 mM histidine;
about 300 mM sorbitol;
about 0.04% (w/v) PS-20; and
about 1 mg/mL methionine, at a pH of about 5.6.

In some embodiments, the anti-CD38 antibody is administered or provided for administration in a pharmaceutical composition comprising about 120 mg/mL of the anti-CD38 antibody;
about 2,000 U/mL of rHuPH20;
about 10 mM histidine;
about 300 mM sorbitol;
about 0.04% (w/v) PS-20; and
about 1 mg/mL methionine, at a pH of about 5.6.

The invention also provides a pharmaceutical composition comprising a BCMAxCD3 bispecific antibody and an anti-CD38 antibody as described herein. For example, the composition can comprise a BCMA binding domain comprising a VH of SEQ ID NO: 24 and a VL of SEQ ID NO: 25 and a CD3 binding domain comprising the VH of SEQ ID NO: 34 and the VL of SEQ ID NO: 35, and an anti-CD38 antibody comprising a VH of SEQ ID NO: 6 and the VL of SEQ ID NO: 7.

In some embodiments, the pharmaceutical composition comprises the BCMAxCD3 bispecific antibody comprising the HC1 of SEQ ID NO: 26, the LC1 of SEQ ID NO: 27, the HC2 of SEQ ID NO: 36 the LC2 of SEQ ID NO: 37, and the anti-CD38 antibody comprising the HC of SEQ ID NO: 14 and the LC of SEQ ID NO: 15. In some embodiments, the BCMAxCD3 bispecific antibody is an IgG4 isotype and comprises phenylalanine at position 405 and arginine at position 409 in a first heavy chain (HC1) and leucine at position 405 and lysine at position 409 in a second heavy chain (HC2), wherein residue numbering is according to the EU Index. In some embodiments, the BCMAxCD3 bispecific antibody further comprises proline at position 228, alanine at position 234 and alanine at position 235 in both the HC1 and the HC2.

The disclosure also provides a kit or a combination comprising the BCMAxCD3 bispecific antibody and the anti-CD38 antibody for use in a method of the application.

Methods of Generating Antibodies Used in the Methods of the Invention

The antibodies used in the methods of the invention binding specific antigens may be selected de novo from, for example, a phage display library, where the phage is engineered to express human immunoglobulins or portions thereof such as Fabs, single chain antibodies (scFv), or unpaired or paired antibody variable regions (Knappik et al., J Mol Biol 296:57-86, 2000; Krebs et al., J Immunol Meth 254:67-84, 2001; Vaughan et al., Nature Biotechnology 14:309-14, 1996; Sheets et al., PITAS (USA) 95:6157-62, 1998; Hoogenboom and Winter, J Mol Biol 227:381, 1991; Marks et al., J Mol Biol 222:581, 1991). Phage display libraries expressing antibody heavy and light chain variable regions as fusion proteins with bacteriophage pIX coat protein as described in Shi et al (2010) J. Mol. Biol. 397:385-96 and Int'l Pat. Pub. No. WO2009/085462. The antibody libraries may be screened for binding to the desired antigen, such as BCMA and the obtained positive clones may be further characterized and the Fabs isolated from the clone lysates, and subsequently cloned as full-length antibodies. Such phage display methods for isolating human antibodies are established in the art. See for example: U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915; and 6,593,081.

T cell redirecting bispecific antibodies may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl.Pat. Publ. No. WO2011/131746. In the methods, two monospecific bivalent antibodies are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 mn at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Exemplary CH3 mutations that may be used in a first heavy chain and in a second heavy chain of the bispecific antibody are K409R and/or F405L.

Additional CH3 mutations that may be used include technologies such as Duobody® mutations (Genmab), Knob-in-Hole mutations (Genentech), electrostatically-matched mutations (Chugai, Amgen, NovoNordisk, Oncomed), the Strand Exchange Engineered Domain body (SEEDbody) (EMD Serono), and other asymmetric mutations (e.g., Zymeworks).

Duobody® mutations (Genmab) are disclosed for example in U.S. Pat. No. 9,150,663 and US2014/0303356 and include mutations F405L/K409R, wild-type/ F405L_R409K, T350I_K370T F405L/K409R, K370W/ K409R, D399AFGHILMNRSTVWY/K409R, T366ADEFGHILMQVY/K409R, L368ADEGHNRSTVQ/ K409AGRH, D399FHKRQ/K409AGRH, F405IKLSTVW/ K409AGRH and Y407LWQ/K409AGRH.

Knob-in-hole mutations are disclosed for example in WO1996/027011 and include mutations on the interface of CH3 region in which an amino acid with a small side chain (hole) is introduced into the first CH3 region and an amino acid with a large side chain (knob) is introduced into the second CH3 region, resulting in preferential interaction between the first CH3 region and the second CH3 region. Exemplary CH3 region mutations forming a knob and a hole are T366Y/F405A, T366W/F405W, F405W/Y407A, T394W/Y407T, T394S/Y407A, T366W/T394S, F405W/ T394S and T366W/T366S_L368A_Y407V.

Heavy chain heterodimer formation may be promoted by using electrostatic interactions by substituting positively charged residues on the first CH3 region and negatively charged residues on the second CH3 region as described in US2010/0015133, US2009/0182127, US2010/028637 or US2011/0123532.

Other asymmetric mutations that can be used to promote heavy chain heterodimerization are L351Y_F405A_Y407V/ T394W, T366IK392M_T394W/F405A_Y407V, T366L_K392M_T394W/F405A_Y407V, L351Y_Y407A/ T366A_K409F, L351Y_Y407A/T366V_K409F, Y407A/ T366A_K409F, or T350V_L351Y_F405A_Y407V/ T350V_T366L_K392L_T394W as described in US2012/ 0149876 or US2013/0195849.

SEEDbody mutations involve substituting select IgG residues with IgA residues to promote heavy chai heterodimerization as described in US20070287170.

Other exemplary mutations that may be used are R409D K370E/D399K_E357K, S354C_T366W/ Y349C_T366S_L368A_Y407V, Y349C_T366W/ S354C_T366S_L368A_Y407V, T366K/L351D, L351K/ Y349E, L351K/Y349D, L351K/L368E, L351Y_Y407A/ T366A_K409F, L351Y_Y407A/T366V_K409F, K392D/ D399K, K392D/E356K, K253E_D282K_K322D/ D239K_E240K_K292D, K392D K409D/D356K_D399K as described in WO2007/147901, WO 2011/143545, WO2013157954, WO2013096291 and US2018/0118849.

Additional bispecific or multispecific structures that can be used as BCMAxCD3 bispecific antibodies include Dual Variable Domain Immunoglobulins (DVD) (Int. Pat. Publ. No. WO2009/134776; DVDs are full length antibodies comprising the heavy chain having a structure VH1-linker-VH2-CH and the light chain having the structure VL1-linker-VL2-CL; linker being optional), structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441), two or more domain antibodies (dAbs) conjugated together, diabodies, heavy chain only antibodies such as camelid antibodies and engineered camelid antibodies, Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer), IgG-like Bispecific (InnClone/Eli Lilly), Ts2Ab (MedImmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)2-Fab (National Research Center for Antibody Medicine—China), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Fc Engineering of Antibodies

The Fc region of the BCMAxCD3 bispecific antibodies such as bispecific or multispecific antibodies or the anti-CD38 antibodies may comprise at least one substitution in the Fc region that reduces binding of the BCMAxCD3 bispecific antibodies to an activating Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP).

Fc positions that may be substituted to reduce binding of the Fc to the activating FcγR and subsequently to reduce effector function are substitutions L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/ P331A/D365E/L358M on IgG1, H268Q/V309L/A330S/ P331S on IgG2, S267E/L328F on IgG1, L234F/L235E/ D265A on IgG1, L234A/L235A/G237A/P238S/H268A/ A330S/P331S on IgG1, S228P/F234A/L235A/G237A/ P238S on IgG4, and S228P/F234A/L235A/G236-deleted/ G237A/P238S on IgG4.

Fc substitutions that may be used to reduce CDC is a K322A substitution.

Well-known S228P substitution may further be made in IgG4 antibodies to enhance IgG4 stability.

An exemplary wild-type IgG1 comprises an amino acid sequence of SEQ ID NO: 16. An exemplary wild-type IgG4 comprises an amino acid sequence of SEQ ID NO: 17.

"Antibody-dependent cellular cytotoxicity," "antibody-dependent cell-mediated cytotoxicity" or "ADCC" is a mechanism for inducing cell death that depends upon the interaction of antibody-coated target cells with effector cells possessing lytic activity, such as natural killer cells (NK), monocytes, macrophages and neutrophils via Fc gamma receptors (FcγR) expressed on effector cells. For example, NK cells express FcγRIIIa, whereas monocytes express FcγRI, FcγRII and FcγRIIIa. ADCC activity of the antibodies may be assessed using an in vitro assay using cells expressing the protein the antibody binds to as target cells and NK cells as effector cells. Cytolysis may be detected by the release of label (e.g., radioactive substrates, fluorescent dyes or natural intracellular proteins) from the lysed cells. In an exemplary assay, target cells are used with a ratio of 1 target cell to 4 effector cells. Target cells are pre-labeled with BATDA and combined with effector cells and the test antibody. The samples are incubated for 2 hours and cell lysis measured by measuring released BATDA into the supernatant. Data is normalized to maximal cytotoxicity with 0.67% Triton X-100 (Sigma Aldrich) and minimal control determined by spontaneous release of BATDA from target cells in the absence of any antibody.

"Antibody-dependent cellular phagocytosis" ("ADCP") refers to a mechanism of elimination of antibody-coated target cells by internalization by phagocytic cells, such as macrophages or dendritic cells. ADCP may be evaluated by using monocyte-derived macrophages as effector cells and cells that express the protein the antibody binds to as target cells also engineered to express GFP or another labeled molecule. In an exemplary assay, effector:target cell ratio may be for example 4:1. Effector cells may be incubated with target cells for 4 hours with or without the antibody of the invention. After incubation, cells may be detached using accutase. Macrophages may be identified with anti-CDT 1b and anti-CD14 antibodies coupled to a fluorescent label, and percent phagocytosis may be determined based on % GFP fluorescence in the CDT 1CD14+macrophages using standard methods.

"Complement-dependent cytotoxicity," or "CDC," refers to a mechanism for inducing cell death in which the Fc effector domain of a target-bound antibody binds and activates complement component C1q which in turn activates the complement cascade leading to target cell death. Activation of complement may also result in deposition of complement components on the target cell surface that facilitate CDC by binding complement receptors (e.g., CR3) on leukocytes. CDC of cells may be measured for example by plating Daudi cells at $1 \times 10^5$ cells/well (50 μL/well) in RPMI-B (RPMI supplemented with 1% BSA), adding 50 μL of test antibodies to the wells at final concentration between 0-100 μg/mL, incubating the reaction for 15 min at room temperature, adding 11 μL of pooled human serum to the wells, and incubation the reaction for 45 min at 37° C. Percentage (%) lysed cells may be detected as % propidium iodide stained cells in FACS assay using standard methods.

Binding of the antibody to FcγR or FcRn may be assessed on cells engineered to express each receptor using flow cytometry. In an exemplary binding assay, $2 \times 10^5$ cells per well are seeded in 96-well plate and blocked in BSA Stain Buffer (BD Biosciences, San Jose, USA) for 30 min at 4° C. Cells are incubated with a test antibody on ice for 1.5 hour at 4° C. After being washed twice with BSA stain buffer, the cells are incubated with R-PE labeled anti-human IgG secondary antibody (Jackson Immunoresearch Laboratories) for 45 min at 4° C. The cells are washed twice in stain buffer and then resuspended in 150 μL of Stain Buffer containing 1:200 diluted DRAQ7 live/dead stain (Cell Signaling Technology, Danvers, USA). PE and DRAQ7 signals of the stained cells are detected by Miltenyi MACSQuant flow cytometer (Miltenyi Biotec, Auburn, USA) using B2 and B4 channel, respectively. Live cells are gated on DRAQ7 exclusion and the geometric mean fluorescence signals are determined for at least 10,000 live events collected. FlowJo software (Tree Star) is used for analysis. Data is plotted as the logarithm of antibody concentration versus mean fluorescence signals. Nonlinear regression analysis is performed.

Chimeric Antigen Receptors (CAR)

Chimeric antigen receptors (CARs) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

CAR typically comprises an extracellular domain that binds the antigen (e.g., prostate neoantigen or B cell maturation antigen (BCMA)), an optional linker, a transmembrane domain, and a cytosolic domain comprising a costimulatory domain and/or a signaling domain.

The extracellular domain of CAR may contain any polypeptide that binds the desired antigen (e.g., prostate neoantigen). The extracellular domain may comprise a scFv, a portion of an antibody or an alternative scaffold. CARs may also be engineered to bind two or more desired antigens that may be arranged in tandem and separated by linker sequences. For example, one or more domain antibodies, scFvs, llama VHH antibodies or other VH only antibody fragments may be organized in tandem via a linker to provide bispecificity or multispecificity to the CAR.

The transmembrane domain of CAR may be derived from the transmembrane domain of CD8, an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDI 1a, CD18), ICOS (CD278), 4-1 BB (CD137), 4-1 BBL, GITR, CD40, BAFFR, HVEM (LIGHTR), SLAMF7, NKp80 (KLRFI), CD160, CD19, IL7R beta, IL2R gamma, IL7R a, ITGA1, VLA1, CD49a, ITGA4, IA4, CD49D, ITGA6, VLA-6, CD49f, ITGAD, CDI Id, ITGAE, CD103, ITGAL, CDI 1a, LFA-1, ITGAM, CDI 1b, ITGAX, CDI 1c, ITGB1, CD29, ITGB2, CD18, LFA-1, ITGB7, TNFR2, DNAM1 (CD226), SLAMF4 (CD244, 2B4), CD84, CD96 (Tactile), CEACAMI, CRT AM, Ly9 (CD229), CD160 (BY55), PSGL1, CD100 (SEMA4D), SLAMF6 (NTB-A, Lyl08), SLAM (SLAMFI, CD150, IPO-3), BLAME (SLAMF8), SELPLG (CD162), LTBR, PAG/Cbp, NKp44, NKp30, NKp46, NKG2D, and/or NKG2C.

The intracellular costimulatory domain of CAR may be derived from the intracellular domains of one or more co-stimulatory molecules. Co-stimulatory molecules are well-known cell surface molecules other than antigen receptors or Fc receptors that provide a second signal required for efficient activation and function of T lymphocytes upon binding to antigen. Exemplary co-stimulatory domains that can be used in CARs are intracellular domains of 4-1BB, CD2, CD7, CD27, CD28, CD30, CD40, CD54 (ICAM), CD83, CD134 (OX40), CD150 (SLAMFI), CD152

(CTLA4), CD223 (LAG3), CD270 (HVEM), CD278 (ICOS), DAP10, LAT, NKD2C SLP76, TRIM, and ZAP70.

The intracellular signaling domain of CAR may be derived from the signaling domains of for example O'O3ζ, CD3ε, CD22, CD79a, CD66d or CD39. "Intracellular signaling domain," refers to the part of a CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

The optional linker of CAR positioned between the extracellular domain and the transmembrane domain may be a polypeptide of about 2 to 100 amino acids in length. The linker can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. The linker may also be derived from a hinge region or portion of the hinge region of any immunoglobulin.

Exemplary CARs that may be used are for example CAR that contains an extracellular domain that binds the prostate neoantigen of the invention, CD8 transmembrane domain and CD3ζ signaling domain. Other exemplary CARs contain an extracellular domain that binds the prostate neoantigen of the invention, CD8 or CD28 transmembrane domain, CD28, 41BB or OX40 costimulatory domain and CD3ζ signaling domain.

CARs are generated by standard molecular biology techniques. The extracellular domain that binds the desired antigen may be derived from antibodies or their antigen binding fragments generated using the technologies described herein.

Outcomes

In some embodiments, the subject treated by the methods provided for herein has a partial response (PR) or better. In some embodiments, the subject treated by the methods provided for herein has a very good partial response (VGPR) or better. In some embodiments, the subject treated by the methods provided for herein has a complete response (CR) or better. In some embodiments, the subject treated by the methods provided for herein has a stringent complete response (sCR) or better. In some embodiments, PR, VGPR, CR, and sCR are as defined by the IMWG 2016 criteria. In some embodiments, PR is defined as having a greater than 50% reduction of serum M-protein and reduction in 24 hours urinary M-protein by >90% or to <200 mg/24 hours. In some embodiments, VGPR is defined as having a serum and urine M-protein level detectable by immunofixation but not on electrophoresis or >90% reduction in serum M-protein plus urine M-protein level <100 mg/24 h. In some embodiments, CR is defined as having a negative immunofixation on serum and urine and disappearance of any soft tissue plasmacytomas and <5% plasma cells in bone marrow. In some embodiments, sCR is defined as the CR definition as above plus normal FLC ratio and absence of clonal cells in bone marrow by immunohistochemistry or immunofluorescence.

In some embodiments, treatment via the methods provided for herein will result in T-cell activation. In some embodiments, the T-cell activation results in an increase in at least one of CD25, PD-1, CD38 on CD4+ T cells, CD38 on CD8+ T cells, or any combination thereof. In some embodiments, the T-cell activation results in an increase in CD25. In some embodiments, the T-cell activation results in an increase in PD-1. In some embodiments, the T-cell activation results in an increase in CD38 on CD4+ T cells. In some embodiments, the T-cell activation results in an increase in or CD38 on CD8+ T cells. In some embodiments, treatment via the methods provided for herein will result in an increase in the frequency of at least one of CD38+ CD8+ T cells, CD38+ CD4+ T cells, Tregs T cells, or any combination thereof. In some embodiments, treatment via the methods provided for herein will result in an increase in the frequency of CD38+ CD8+ T cells. In some embodiments, treatment via the methods provided for herein will result in an increase in the frequency of CD38+ CD4+ T cells. In some embodiments, treatment via the methods provided for herein will result in an increase in the frequency of Tregs T cells.

In some embodiments, the methods provided for herein result in an enhanced activity of, or results in an increased efficacy of the components of the method when administered as monotherapies. In some embodiments, treatment via the methods provided for herein results in enhanced activity of the BCMA x CD3 bispecific antibody as compared to a treatment without the anti-CD38 antibody. In some embodiments, treatment via the methods provided for herein results in enhanced activity of the anti-CD38 antibody as compared to a treatment without the BCMA x CD3 bispecific antibody.

Numbered Embodiments

The present disclosure also provides the following numbered embodiments:

1. A method of treating a cancer in a subject in need thereof, comprising:
   (1) administering to the subject a BCMAxCD3 bispecific antibody at a dose of 200 µg/kg to 6 mg/kg or 60 mg to 600 mg every 1-4 weeks, and
   (2) subcutaneously administering to the subject an anti-CD38 antibody at a dose of 1200 mg to 2400 mg every 1-4 weeks.

1a. A method of treating a cancer in a subject in need thereof, comprising:
   (1) intravenously administering to the subject a BCMAxCD3 bispecific antibody at a dose of 200 µg/kg to 1 mg/kg every 1-2 weeks, and
   (2) subcutaneously administering to the subject an anti-CD38 antibody at a dose of 1200 mg to 2400 mg every 1-4 weeks.

1a1. The method of embodiment 1a, wherein the BCMAxCD3 bispecific antibody is intravenously administered to the subject at a dose of 270 µg/kg weekly.

1a2. The method of embodiment 1a or 1a1, wherein the anti-CD38 antibody is subcutaneously administered at a dose of 1800 mg weekly, biweekly, every three weeks or every four weeks.

1a3. The method of embodiment 1a1, wherein the anti-CD38 antibody is subcutaneously administered at a dose of 1800 mg once every week during week 1 to week 8 of the treatment, once every two weeks during week 9 to week 24 of the treatment, and once every four weeks after week 24 of the treatment.

2. The method of embodiment 1, comprising:
   (1) subcutaneously administering to the subject the BCMAxCD3 bispecific antibody at a dose of 1 mg/kg to 6 mg/kg or 60 mg to 600 mg every 1-4 weeks, and
   (2) subcutaneously administering to the subject the anti-CD38 antibody at a dose of 1600 mg to 2000 mg every 1-4 weeks.

3. The method of Embodiment 2, further comprising subcutaneously administering to the subject the BCMAxCD3 bispecific antibody at a dose lower than 0.5 mg/kg prior to step (1).

3a. The method of embodiment 3, wherein the BCMAxCD3 bispecific antibody at the dose lower than 0.5 mg/kg is subcutaneously administered to the subject after the initial administration of the anti-CD38 antibody, preferably the BCMAxCD3 bispecific antibody at the dose lower than 0.5 mg/kg is initially administered at least 20 hours after the initial administration of the anti-CD38 antibody.

3b. The method of embodiment 3 or 3a, wherein the BCMAxCD3 bispecific antibody is subcutaneously administered to the subject at a dose of 0.01 to 0.10 mg/kg, such as 0.01, 0.02, 0.03, 0.04, 0.05, 0.06, 0.07, 0.08, 0.09 and 0.10 mg/kg, on Day 1 of the treatment.

3c. The method of embodiments 3 or 3a, wherein the BCMAxCD3 bispecific antibody is subcutaneously administered to the subject at a dose of 0.01 to 0.10 mg/kg, such as 0.01, 0.02, 0.03, 0.04, 0.05, 0.06, 0.07, 0.08, 0.09 and 0.10 mg/kg, on Day 2 of the treatment.

3d. The method of any one of embodiments 3 to 3c, wherein 0.10 to 0.50 mg/kg, such as 0.10, 0.15, 0.20, 0.25, 0.30, 0.35, 0.40, 0.45 or 0.50 mg/kg, or any value in-between, of the BCMAxCD3 bispecific antibody is administered on Day 3 of the treatment.

3e. The method of any one of embodiments 3 to 3c, wherein 0.10 to 0.50 mg/kg, such as 0.10, 0.15, 0.20, 0.25, 0.30, 0.35, 0.40, 0.45 or 0.50 mg/kg, or any value in-between, of the BCMAxCD3 bispecific antibody is administered on Day 4 of the treatment.

3f. The method of any one of embodiments 3 to 3c, wherein 0.10 to 0.50 mg/kg, such as 0.10, 0.15, 0.20, 0.25, 0.30, 0.35, 0.40, 0.45 or 0.50 mg/kg, or any value in-between, of the BCMAxCD3 bispecific antibody is administered on Day 5 of the treatment.

3g. The method of any one of embodiments 3 to 3f, wherein the initial dose of 1 mg/kg to 6 mg/kg or 200 mg to 600 mg of the BCMAxCD3 bispecific antibody is subcutaneously administered to the subject on Day 6, 7 or 8 of the treatment.

4. The method of any one of embodiments 2 to 3g, wherein the BCMAxCD3 bispecific antibody is subcutaneously administered to the subject at a dose of 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3.0 mg/kg, or 100, 150, 200, 250, 260, 270, 280, 290, 300, 310, 320, 330, 340, 350 mg, 400 mg, 450 mg, 500 mg, 550 mg, 600 mg, or any dose in-between, once every week or once every two weeks.

4a. The method of embodiment 4, wherein the BCMAxCD3 bispecific antibody is subcutaneously administered to the subject at a dose of 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0 mg/kg, 3.1 mg/kg, 3.2 mg/kg, 3.3. mg/kg, 3.4, mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, or 6.0 mg/kg weekly.

4b. The method of embodiment 4, wherein the BCMAxCD3 bispecific antibody is subcutaneously administered to the subject at a dose of 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0 mg/kg, 3.1 mg/kg, 3.2 mg/kg, 3.3. mg/kg, 3.4, mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, or 6.0 mg/kg biweekly.

4c. The method of embodiment 4, wherein the BCMAxCD3 bispecific antibody is subcutaneously administered to the subject at a dose of 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0 mg/kg, 3.1 mg/kg, 3.2 mg/kg, 3.3. mg/kg, 3.4, mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, or 6.0 mg/kg triweekly.

4d. The method of embodiment 4, wherein the BCMAxCD3 bispecific antibody is subcutaneously administered to the subject at a dose of 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0 mg/kg, 3.1 mg/kg, 3.2 mg/kg, 3.3. mg/kg, 3.4, mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, or 6.0 mg/kg monthly.

4e. The method of embodiment 4, wherein the BCMAxCD3 bispecific antibody is subcutaneously administered to the subject at a dose of 100, 150, 200, 250, 260, 270, 280, 290, 300, 310, 320, 330, 340 or 350 mg, or any dose in-between, once every week.

4f. The method of any one of embodiments 4 to 4c, wherein the BCMAxCD3 bispecific antibody is subcutaneously administered to the subject at a dose of 100, 150, 200, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 mg, or any dose in-between, once every two weeks.

5. The method of embodiment 4, wherein the BCMAxCD3 bispecific antibody is subcutaneously administered to the subject at a dose of 1.5 mg/kg weekly, 150 mg weekly, 3.0 mg/kg weekly or biweekly, 6.0 mg/kg biweekly or monthly, 300 mg biweekly, or 600 mg biweekly or monthly.

6. The method of embodiment 5, wherein the BCMAxCD3 bispecific antibody is subcutaneously administered to the subject at a dose of 1.5 mg/kg weekly.

6a. The method of embodiment 5, wherein the BCMAxCD3 bispecific antibody is subcutaneously administered to the subject at a dose of 60-150 mg weekly.

6b. The method of embodiment 5, wherein the BCMAxCD3 bispecific antibody is subcutaneously administered to the subject at a dose of 3 mg/kg weekly.

6c. The method of embodiment 5, wherein the BCMAxCD3 bispecific antibody is subcutaneously administered to the subject in a dose 3.0 mg/kg biweekly or triweekly.

6d. The method of embodiment 5, wherein the BCMAxCD3 bispecific antibody is subcutaneously administered to the subject in a dose 150-300 mg weekly.

6e. The method of embodiment 5, wherein the BCMAxCD3 bispecific antibody is subcutaneously administered to the subject in a dose 150-300 mg biweekly or triweekly.

6f. The method of embodiment 5, wherein the BCMAxCD3 bispecific antibody is subcutaneously administered to the subject in a dose 6.0 mg/kg biweekly.

6g. The method of embodiment 5, wherein the BCMAxCD3 bispecific antibody is subcutaneously administered to the subject in a dose 6.0 mg/kg triweekly or monthly.

6h. The method of embodiment 5, wherein the BCMAxCD3 bispecific antibody is subcutaneously administered to the subject in a dose 300-600 mg biweekly.

6i. The method of embodiment 5, wherein the BCMAxCD3 bispecific antibody is subcutaneously administered to the subject in a dose 300-600 mg triweekly or monthly.

6j. The method of embodiment 5, wherein the BCMAxCD3 bispecific antibody is subcutaneously administered to the subject at a dose of 60-150 mg weekly for the first 8 weeks, followed by biweekly administration of the BCMAxCD3 bispecific antibody at a dose of 150-300 mg.

6k. The method of embodiment 5, wherein the BCMAxCD3 bispecific antibody is subcutaneously administered to the subject at a dose of 1.5 mg/kg weekly for 8 weeks (2 Cycles), followed by biweekly subcutaneous administration of the BCMAxCD3 bispecific antibody at a dose of 3.0 mg/kg, e.g., for 4-12 weeks (1-3 cycles).

6l. The method of embodiment 6k, wherein the BCMAxCD3 bispecific antibody is subcutaneously administered to the subject at a dose of 1.5 mg/kg weekly for 8 weeks (2 Cycles), followed by biweekly subcutaneous administration of the BCMAxCD3 bispecific antibody at a dose of 3.0 mg/kg, e.g., for 4-12 weeks, followed by monthly subcutaneous administration of the BCMAxCD3 bispecific antibody at a dose of 6.0 mg/kg.

6m. The method of embodiment 5, wherein the BCMAxCD3 bispecific antibody is subcutaneously administered to the subject at a dose of 60-150 mg weekly for 8 weeks (2 Cycles), followed by biweekly subcutaneous administration of the BCMAxCD3 bispecific antibody at a dose of 150-300 mg, e.g., for 4-12 weeks (1-3 cycles).

6n. The method of embodiment 5, wherein the BCMAxCD3 bispecific antibody is subcutaneously administered to the subject at a dose of 60-150 mg weekly for 8 weeks (2 Cycles), followed by biweekly subcutaneous administration of the BCMAxCD3 bispecific antibody at a dose of 150-300 mg, e.g., for 4-12 weeks (1-3 cycles), further followed by monthly subcutaneous administration of the BCMAxCD3 bispecific antibody at a dose of 300-600 mg.

7. The method of any one of embodiments 1 to 6n, wherein the anti-CD38 antibody is subcutaneously administered to the subject at the dose of 1800 mg once every week during week 1 to week 8 of the treatment, once every two weeks during week 9 to week 24 of the treatment, and once every four weeks after week 24 of the treatment.

7a. The method of any one of embodiments 1 to 6n, wherein the anti-CD38 antibody is subcutaneously administered to the subject at the dose of 1800 mg once every week.

7b. The method of any one of embodiments 1 to 6n, wherein the anti-CD38 antibody is subcutaneously administered to the subject at the dose of 1800 mg once every two weeks.

7c. The method of any one of embodiments 1 to 6n, wherein the anti-CD38 antibody is subcutaneously administered to the subject at the dose of 1800 mg once every three weeks.

7d. The method of any one of embodiments 1 to 6n, wherein the anti-CD38 antibody is subcutaneously administered to the subject at the dose of 1800 mg once every four weeks.

8. The method of any one of embodiments 1 to 7d, wherein the anti-CD38 antibody is administered or provided for administration together with rHuPH20, such as about 30,000 U of rHuPH20. 8a. The method of any one of embodiments 1 to 7d, further comprising administering to the subject rHuPH20 to decrease the injection volume required, facilitating the subcutaneous administration of the anti-CD38 antibody.

8b. The method of embodiment 8a, wherein the rHuPH20 is subcutaneously administered together with the anti-CD38 antibody.

8c. The method of embodiment 8a, wherein the rHuPH20 is subcutaneously administered separately from the anti-CD38 antibody.

8d. The method of any one of embodiments 8a to 8d, wherein the rHuPH20 is subcutaneously administered at a dose of 10,000-50,000 U, such as 10,000, 20,000, 30,000, 40,000 or 50,000 U, or any value in-between.

8e. The method of any one of embodiments 8a to 8d, wherein the rHuPH20 is subcutaneously administered at a dose of 30,000U.

8d. The method of any one of embodiments 8 to 8e, wherein the rHuPH20 and the anti-CD38 antibody are administered together in the same pharmaceutical composition.

9. The method of any one of embodiments 1 to 8d, wherein the BCMAxCD3 bispecific antibody comprises:
   (i) a BCMA binding domain comprising a heavy chain variable region (VH) having heavy chain complementarity determining regions (HCDRs) HCDR1, HCDR2 and HCDR3 of the amino acid sequences of SEQ ID NO: 18, SEQ ID NO: 19, and SEQ ID NO: 20, respectively, and a light chain variable region (VL) having light chain complementarity determining regions (LCDRs) LCDR1, LCDR2 and LCDR3 of the amino acid sequences of SEQ ID NO: 21, SEQ ID NO: 22, and SEQ ID NO: 23, respectively, and
   (ii) a CD3 binding domain comprising a VH having HCDR1, HCDR2 and HCDR3 of the amino acid sequences of SEQ ID NO: 28, SEQ ID NO: 29, and SEQ ID NO: 30, respectively, and a VL having LCDR1, LCDR2 and LCDR3 of the amino acid sequences of SEQ ID NO: 31, SEQ ID NO: 32, and SEQ ID NO: 33, respectively.

9a. The method of any one of embodiments 1 to 8d, wherein the BCMAxCD3 bispecific antibody comprises a BCMA binding domain that binds BCMA selected from the group consisting of the BCMA binding domain of ACTR cancer therapy by Seattle Genetics, AFM-26, ALLO-715, anti-BCMA allogenic CAR-T cell therapy by CRISPR Therapeutics, anti-BCMA CAR-T therapy by Sorrento Therapeutics, anti-CD19/BCMA CAR-T cell therapy by Hrain Biotechnology, BCMA CAR-T therapy by Chineo Med (Beijing), BCMA TAC-T cell therapy by Triumvira Immunologics, BCMA-CAR T cell therapy by Shanghai Unicar-Therapy Biomed, BCMA/CD3 antibody by Regeneron, CAR-NK cell therapies by NantKwest, CC-93629, CMD-505, CTX-4419, CYAD-211, HDP-101, HPN-217, P-BCMA-ALLO1, TNB-383B, bb-2121, AUTO-2, BCMA chimeric antigen receptor therapy by Pregene, BCMA-CAR T cells by Shanghai Bioray Laboratory, BCMA-CAR-T cells by CARsgen Therapeutics, CAR-T/TCR-T cell immunotherapy by Shenzhen BinDeBio, ET-140, P-BCMA-101, REGN-5458, AMG-701, anti BCMA CAR-T cell therapy by Cellular Biomedicine Group, bb-21217, BI-836909, CC-93269, Descartes-08, IM-21, JNJ-64007957, MEDI-2228 or PF-06863135.

9b. The method of any one of embodiments 1 to 8d, wherein the BCMAxCD3 bispecific antibody comprises a BCMA binding domain described in Int. Pat. Publ. No. WO2017/031104.

10. The method of embodiment 9, wherein the BCMAxCD3 bispecific antibody comprises a BCMA binding domain comprising the VH having the amino acid sequence of SEQ ID NO: 24 and the VL having the amino acid sequence of SEQ ID NO: 25; and a CD3 binding domain comprising the VH having the amino acid sequence of SEQ ID NO: 34 and the VL having the amino acid sequence of SEQ ID NO: 35.

11. The method of embodiment 10, wherein the BCMAxCD3 bispecific antibody comprises a BCMA binding domain comprising a first heavy chain (HC1) having the amino acid sequence of SEQ ID NO: 26, a first light chain (LC1) having the amino acid sequence of SEQ ID NO: 27, and a CD3 binding domain comprising a second heavy chain (HC2) having the amino acid sequence of SEQ ID NO: 36, and a second light chain (LC2) having the amino acid sequence of SEQ ID NO: 37.

11a. The method of any one of embodiments 1 to 8d, wherein the BCMAxCD3 bispecific antibody comprises elranatamab (also named PF-06863135), teneobio (also named TNB-383B), REGN5458, REGN5459, pavurutamab (also named AMG-701), BI 836909, CC-93269, WVT078 or teclistamab (also named JNJ-957 or JNJ-64007957).

11b. The method of any one of embodiments 1 to 8d, wherein the BCMAxCD3 bispecific antibody comprises an antigen binding fragment, such as Fab, F(ab')2, Fd or Fv fragment.

11c. The method of any one of embodiments 1 to 8d, wherein the BCMAxCD3 bispecific antibody is chimeric, humanized or human.

11d. The method of any one of embodiments 1 to 8d, wherein the BCMAxCD3 bispecific antibody is an IgG1, an IgG2, an IgG3 or an IgG4 isotype.

11e. The method of any one of embodiments 1 to 8d, wherein the BCMAxCD3 bispecific antibody is an IgG4 isotype.

12. The method of any one of embodiments 1 to 11e, wherein the anti-CD38 antibody comprises a VH having HCDR1, HCDR2 and HCDR3 of the amino acid sequences of SEQ ID NO: 8, SEQ ID NO: 9, and SEQ ID NO: 10, respectively, and a VL having LCDR1, LCDR2 and LCDR3 of the amino acid sequences of SEQ ID NO: 11, SEQ ID NO: 12, and SEQ ID NO: 13, respectively.

12a. The method of any one of embodiments 1 to 11a, wherein the anti-CD38 antibody comprises a) the VH of SEQ ID NO: 38 and the VL of SEQ ID NO: 39; b) the VH of SEQ ID NO: 40 and the VL of SEQ ID NO: 41; c) the VH of SEQ ID NO: 42 and the VL of SEQ ID NO: 43; or d) the VH of SEQ ID NO: 44 and the VL of SEQ ID NO: 45.

13. The method of embodiment 12, wherein the CD38 antibody comprises the VH having the amino acid sequence of SEQ ID NO: 6, and the VL having the amino acid sequence of SEQ ID NO: 7.

13a. The method of any one of embodiments 1 to 11a, wherein the anti-CD38 antibody is selected from the group consisting of mAb003 described in U.S. Pat. No. 7,829,673; mAb024 described in U.S. Pat. No. 7,829,673; MOR-202 (MOR-03087) described in U.S. Pat. No. 8,088,896; or isatuximab described in U.S. Pat. No. 8,153,765, and daratumumab.

13b. The method of any one of embodiments 1 to 11a, wherein the anti-CD38 antibody comprises the HC of SEQ ID NO: 14 and the LC of SEQ ID NO: 15.

13c. The method of any one of embodiments 1 to 11a, wherein the anti-CD38 antibody is chimeric, humanized or human.

13d. The method of any one of embodiments 1 to 11a, wherein the anti-CD38 antibody is an IgG1, an IgG2, an IgG3 or an IgG4 isotype.

13e. The method of any one of embodiments 1 to 11a, wherein the anti-CD38 antibody is an IgG1 isotype.

13f. The method of any one of embodiments 1 to 13e, wherein the BCMAxCD3 bispecific antibody and/or the anti-CD38 antibody comprises one or more Fc substitutions described herein.

13g. The method of embodiment 13f, wherein the Fc substitution is selected from the group consisting of F234A/L235A on IgG4, L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4 and S228P/F234A/L235A/G236-deleted/G237A/P238S on IgG4, wherein residue numbering is according to the EU index.

13h. The method of embodiment 13f, wherein the Fc substitution is selected from the group consisting of:
 (1) F234A/L235A on IgG4;
 (2) L234A/L235A on IgG1;
 (3) V234A/G237A/P238S/H268A/V309L/A330S/P331S on IgG2;
 (4) F234A/L235A on IgG4;
 (5) S228P/F234A/L235A on IgG4;
 (6) N297A on all Ig isotypes;
 (7) V234A/G237A on IgG2;
 (8) K214T/E233P/L234V/L235A/G236-deleted/A327G/P331A/D365E/L358M on IgG1;
 (9) H268Q/V309L/A330S/P33IS on IgG2;
 (10) S267E/L328F on IgG1;
 (11) L234F/L235E/D265A on IgG1;
 (12) L234A/L235A/G237A/P238S/H268A/A330S/P331S on IgG1;
 (13) S228P/F234A/L235A/G237A/P238S on IgG4 and S228P/F234A/L235A/G236-deleted/G237A/P238S on IgG4;
 (14) S228P substitution.

13i. The method of any one of embodiments 1 to 13e, wherein the BCMAxCD3 bispecific antibody comprises one or more asymmetric substitutions in a first CH3 domain or in a second CH3 domain, or in both the first CH3 domain and the second CH3 domain.

13j. The method of embodiment 13i, wherein the one or more asymmetric substitutions is selected from the group consisting of F450L/K409R, wild-type/F409L_R409K, T366Y/F405A, T366W/F405W, F405W/Y407A, T394W/Y407T, T394S/Y407A, T366W/T394S, F405W/T394S and T366W/T366S_L368A_Y407V, L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F and T350V_L351Y_F405A_Y407V/T350V_T366L_K392L_T394W.

13k. The method of any one of embodiments 1 to 13e, wherein the BCMAxCD3 bispecific antibody is an IgG4 isotype and comprises phenylalanine at position 405 and arginine at position 409 in a first heavy chain (HC1) and leucine at position 405 and lysine at position 409 in a second heavy chain (HC2), wherein residue numbering is according to the EU Index.

13l. The method of embodiment 13k, wherein the BCMAxCD3 bispecific antibody further comprises proline at position 228, alanine at position 234 and alanine at position 235 in both the HC1 and the HC2.

14. The method of any one of embodiments 1 to 13l, wherein the cancer comprises a hematological malignancy or a solid tumor.

14a. The method of embodiment 14, wherein the hematological malignancy is a multiple myeloma, a smoldering multiple myeloma, a monoclonal gammopathy of undetermined significance (MGUS), an acute lymphoblastic leukemia (ALL), a diffuse large B-cell lymphoma (DLBCL), a Burkitt's lymphoma (BL), a follicular lymphoma (FL), a mantle-cell lymphoma (MCL), Waldenstrom's macroglobulinema, a plasma cell leukemia, a light chain amyloidosis (AL), a precursor B-cell lymphoblastic leukemia, a precursor B-cell lymphoblastic leukemia, an acute myeloid leukemia (AML), a myelodysplastic syndrome (MDS), a chronic lymphocytic leukemia (CLL), a B cell malignancy, a chronic myeloid leukemia (CML), a hairy cell leukemia (HCL), a blastic plasmacytoid dendritic cell neoplasm, Hodgkin's lymphoma, non-Hodgkin's lymphoma, a marginal zone B-cell lymphoma (MZL), a mucosa-associated lymphatic tissue lymphoma (MALT), plasma cell leukemia, anaplastic large-cell lymphoma (ALCL), leukemia or lymphoma 14b. The method of embodiment 14a, wherein the hematological malignancy comprises multiple myeloma.

14c. The method of embodiment 14b, wherein the multiple myeloma is a newly diagnosed multiple myeloma.

14d. The method of embodiment 14b, wherein the multiple myeloma is a relapsed or a refractory multiple myeloma (RRMM).

14e. The method of embodiment 14b, wherein the multiple myeloma is a high-risk multiple myeloma.

14f. The method of embodiment 14b, wherein the subject having the high-risk multiple myeloma has one or more chromosomal abnormalities comprising: t(4;14)(p16;q32), t(14;16)(q32;q23), del17p, 1qAmp, t(4;14)(p16;q32) and t(14;16)(q32;q23), t(4;14)(p16;q32) and del17p, t(14;16)(q32;q23) and del17p; or t(4;14)(p16;q32), t(14;16)(q32;q23) and del17p, or any combination thereof.

14g. The method of any one of embodiments 1 to 14f, wherein the cancer comprises multiple myeloma that is relapsed or refractory to a treatment.

14h. The method of embodiment 14g, wherein the cancer comprises multiple myeloma that is relapsed or refractory to a treatment with the anti-CD38 antibody, lenalidomide, bortezomib, pomalidomide, carfilzomib, elotuzumab, ixazomib, melphalan or thalidomide, or any combination thereof.

14i. The method of any one of embodiments 1 to 14, wherein the cancer comprises AML.

14j. The method of embodiment 14i, wherein the AML is AML with at least one genetic abnormality, AML with multilineage dysplasia, therapy-related AML, undifferentiated AML, AML with minimal maturation, AML with maturation, acute myelomonocytic leukemia, acute monocytic leukemia, acute erythroid leukemia, acute megakaryoblastic leukemia, acute basophilic leukemia, acute panmyelosis with fibrosis or myeloid sarcoma.

14k. The method of any one of embodiments 1 to 14, wherein the cancer comprises any BCMA expressing cancer, such as multiple myeloma, a smoldering myeloma, a monoclonal gammopathy of undetermined significance (MGUS), a B-cell acute lymphoblastic leukemia, a diffuse large B-cell lymphoma, a Burkitt's lymphoma, a follicular lymphoma, a mantle-cell lymphoma, Waldenstrom's macroglobulinema, plasma cell leukemia, light chain amyloidosis or non-Hodgkin's lymphoma.

14l. The method of any one of embodiments 1 to 14, wherein the subject is relapsed or refractory to treatment with the anti-CD38 antibody or lenalidomide, or a combination thereof.

14m. The method of any one of embodiments 1 to 14, wherein the subject is refractory or relapsed to treatment with THALOMID® (thalidomide), REVLIMID® (lenalidomide), POMALYST® (pomalidomide), VELCADE® (bortezomib), NINLARO (ixazomib), KYPROLIS® (carfilzomib), FARADYK® (panobinostat), AREDIA® (pamidronate), ZOMETA® (zoledronic acid), DARZALEX® (daratumumab), elotuzumab (Empliciti®), SARCLISA® (isatuximab), or melphalan (Alkeran®).

14n. The method of any one of embodiments 1 to 14, wherein the subject is relapsed to treatment with DARZALEX® (daratumumab).

15. A method of treating multiple myeloma in a subject in need thereof, comprising:
(1) subcutaneously administering to the subject 1.5 mg/kg of a BCMAxCD3 bispecific antibody once every week during week 1 to week 8 of the treatment, and 3.0 mg/kg of the BCMAxCD3 bispecific antibody once every two weeks and/or 6.0 mg/kg of a BCMAxCD3 bispecific antibody once every month after week 8 of the treatment, and
(2) subcutaneously administering to the subject 1800 mg of an anti-CD38 antibody once every week during week 1 to week 8 of the treatment, once every two weeks during week 9 to week 24 of the treatment, and once every four weeks after week 24 of the treatment,
wherein the BCMAxCD3 bispecific antibody comprises a first heavy chain (HC1) of SEQ ID NO: 26, a first light chain (LC1) of SEQ ID NO: 27, a second heavy chain (HC2) of SEQ ID NO: 36, and a second light chain (LC2) of SEQ ID NO: 37, and the anti-CD38 antibody comprises the HC of SEQ ID NO: 14 and the LC of SEQ ID NO: 15.

15a. The method of embodiment 15, wherein the BCMAxCD3 bispecific antibody is subcutaneously administered to the subject at a dose of 1.5 mg/kg once every week during week 1 to week 8 of the treatment, 3.0 mg/kg once every two weeks during week 9 to week 20 of the treatment, and 6.0 mg/kg thereafter.

16. The method of embodiment 15 or 15a, further comprising subcutaneously administering to the subject 0.06 mg/kg of the BCMAxCD3 bispecific antibody on Day 2 of the treatment and 0.3 mg/kg of the BCMAxCD3 bispecific antibody on Day 4 of the treatment, prior to the initial subcutaneous administration of the 1.5 mg/kg BCMAxCD3 bispecific antibody.

17. The method of embodiment 15 or 15a, further comprising administering 3 mg/kg of the bispecific antibody biweekly on Day 1 of the next planned 28 Day cycle.

18. The method of any one of embodiments 1 to 17, wherein the subject has received at least one prior treatment of multiple myeloma, preferably, the subject is relapsed or refractory to the at least one prior treatment, more preferably, the prior treatment comprises at least one of a proteasome inhibitor (PI) and an immunomodulatory agent (IMiD).

19. The method of embodiment 18, wherein the subject is refractory or relapsed to a treatment selected from the group consisting of an anti-CD38 antibody, lenalidomide, bortezomib, pomalidomide, carfilzomib, elotuzumab, ixazomib, isatuximab, melphalan and thalidomide, or any combination thereof, preferably, the subject is lenalidomide refractory.

20. The method of any one of embodiments 1 to 19, further comprising administering to the subject another treatment, such as pomalidomide and/or dexamethasone.

21. The method of any one of embodiments 1 to 20, wherein the treatment results in T-cell activation, such as an increase in at least one of CD25, PD-1, CD38 on CD4+ and CD8+ T cells.

22. The method of any one of embodiments 1 to 21, wherein the treatment results in an increase in frequency of at least of CD38+ CD8+ T cells, CD38+ CD4+ T cells and Tregs T cells.

23. The method of any one of embodiments 1 to 20, wherein the treatment results in enhanced activity of the BCMAxCD3 bispecific antibody compared to a treatment without the anti-CD38 antibody.

24. The method of any one of embodiments 1 to 20, wherein the treatment results in enhanced activity of the anti-CD38 antibody compared to a treatment without the BCMAxCD3 bispecific antibody.

25. A BCMAxCD3 bispecific antibody for use in treating a cancer in a subject in need thereof using a method of any one of embodiments 1 to 24.

26. An anti-CD38 antibody for use in treating a cancer in a subject in need thereof using a method of any one of embodiments 1 to 24.

27. A combination of a BCMAxCD3 bispecific antibody and an anti-CD38 antibody for use in treating a cancer in a subject in need thereof using a method of any one of embodiments 1 to 24.

28. Use of a BCMAxCD3 bispecific antibody in the manufacture of a medicament for treating a cancer in a subject in need thereof using a method of any one of embodiments 1 to 24.

29. Use of an anti-CD38 antibody in the manufacture of a medicament for treating a cancer in a subject in need thereof using a method of any one of embodiments 1 to 24.

30. Use of a combination of a BCMAxCD3 bispecific antibody and an anti-CD38 antibody in the manufacture of a medicament for treating a cancer in a subject in need thereof using a method of any one of embodiments 1 to 243.

31. A kit comprising a BCMAxCD3 bispecific antibody, an anti-CD38 antibody and instructions on using the antibodies in treating a cancer in a subject in need thereof using a method of any one of embodiments 1 to 24.

While having described the invention in general terms, the embodiments of the invention will be further disclosed in the following examples that should not be construed as limiting the scope of the claims.

EXAMPLES

The following examples are provided to further describe some of the embodiments disclosed herein. The examples are intended to illustrate, not to limit, the disclosed embodiments.

General Materials and Methods

Antibodies and Reagents

Anti-BCMA/anti-CD3 antibody JNJ-64007957 (referred to as JNJ-957) (described in WO2017031104A1) and daratumumab were made by Janssen Pharmaceuticals. CNT07008 (CD3xnull), BC3B4 (BCMAxnull) and 3930 (IgG isotype control), all made by Janssen Pharmaceuticals, were used as control antibodies.

JNJ-957 (teclistamab) comprises a BCMA binding arm BCMB69 and a CD3 binding arm CD3B219, the amino acid sequences of which are shown in Table 8a and Table 8b, respectively.

Bone marrow and peripheral blood mononuclear cells

Peripheral blood mononuclear cells (PBMCs) from healthy donors and MM patients, and bone marrow mononuclear cells (BM-MNCs) from MM patient BM aspirates were isolated by Ficoll-Hypaque density-gradient centrifugation.

Flow cytometric analysis of bone marrow and blood samples from MM patients

BM-localized MM cells were identified and analysed for cell surface marker expression levels by staining $1.0 \times 10^6$ cells/mL with HuMax-003 (CD38) FITC (this antibody binds to an epitope distinct from the epitope bound by daratumumab, Janssen Pharmaceuticals), CD138 PE, CD56 PC7, CD45 Krome Orange (all Beckman Coulter), CD269 (BCMA) APC (Biolegend), CD274 (PD-L1) BV421 and CD19 APC-H7 (both Becton Dickinson). BM or PB immune cell subsets were identified and analysed for cell surface marker expression levels by staining $1.0 \times 10^6$ cells/mL with CD45 Krome Orange, CD56 PC7 (both Beckman Coulter), CD14 APC-H7, CD19 APC-H7, CD3 V450, CD4 APC-H7 or PE, CD8 FITC, CD45-RA APC, CD127 PE.Cy7, CD62L PE, CD274 (PD-1) BV421, CD16 APC, HLA-DR APC-H7 (all Becton Dickinson) and CD25 PE (Dako) or with CD4 BUV395 (BD Biosciences), CD8 BUV737 (BD Biosciences), PD-1 BV421 (BD Biosciences), TIM-3 BV650 (BD Biosciences), CD3 BV711 (BD Biosciences), CD45RO BV786 (BD Biosciences), CD38 Humab-003-FITC (Janssen), CD45RA PerCP-Cy5.5 (BD Biosciences), HLA-DR PE (BD Biosciences), LAG-3 PE-eF610 (ThermoFisher), CD25 PE-Cy7 (BD Biosciences), CCR7 AF647 (BD Biosciences), CD127 APC-eF780 (ThermoFisher). All BM samples were analysed within 24 hours from the time the sample was collected.

Flow cytometry was performed using a 7-laser LSR-FORTESSA (Becton Dickinson). Fluorescent labeled beads (CS&T beads, Becton Dickinson) were used daily to monitor the performance of the flow cytometer and verify optical path and stream flow. This procedure enables controlled standardized results and allows the determination of long-term drifts and incidental changes within the flow cytometer. No changes were observed which could affect the results. Compensation beads were used to determine spectral overlap, compensation was automatically calculated using Diva software. Flow cytometry data were analyzed using FACS Diva software.

Bioluminescence imaging (BLI)-based lysis assay using LUC-transduced MM cell lines LUC-transduced MM cell lines were cultured in the presence or absence of pooled BM stromal cells (BMSCs) obtained from newly diagnosed MM patient (n=12) for 16 hours prior to incubation with effector cells (freshly isolated PBMCs from healthy donors) at an effector to target ratio of 9:1, and serial dilutions of JNJ-957 (0.00256-4.0 μg/mL) or control antibodies in 96-well flat bottom plates (Greiner-Bio-One) for 48 hours. The survival of LUC$^+$-MM cells was then determined by BLI, 10 minutes after addition of the substrate luciferin (150 μg/mL; Promega). Lysis of MM cells was determined using the following formula: % lysis=1-(mean BLI signal in the presence of effector cells and JNJ-957/mean BLI signal in the presence of effector cells in untreated wells)×100%.

To evaluate the effect of in vivo pretreatment of PB MNCs with daratumumab monotherapy on efficacy of JNJ-957, the LUC-transduced MM cell line 4 was also co-cultured with PB MNCs, obtained from MM patients before initiation of daratumumab monotherapy and at the time of best response to daratumumab monotherapy (effector to target ratio of 9:1). The BLI assay was performed as described before.

Cytogenetic Analysis

Cytogenetic abnormalities were assessed in purified MM cells by fluorescence in situ hybridization (FISH) and single nucleotide polymorphism (SNP) array. High-risk disease was defined by the presence of del(17p), del(1p), ampl(1q), t(4;14) or t(14;16)[2].

Soluble BCMA Assay

Soluble BCMA (sBCMA) was measured in cell culture supernatants using MSD GOLD™ 96-well Small Spot Streptavidin SECTOR plates (Meso Scale Diagnostics), according to the manufacturer's recommended protocol.

Multiplex Cytokine Assay

Cytokines [interferon-gamma (IFN-γ), interleukin (IL)-2, IL-6, IL-8, IL-10, and tumor necrosis factor-alpha (TNF-α)] in the cell culture supernatants were analyzed using V-Plex proinflammatory Panel 1 Human Kit (Meso Scale Diagnostics), according to the manufacturer's protocol.

Statistics

Comparisons between variables were performed using two-tailed (paired) Student's t-test, or Mann-Whitney Utest or Wilcoxon matched-pairs signed-rank test in case the data do not follow a normal distribution. Correlations between variables were made using the Spearman's rank correlation coefficient. P-values below 0.05 were considered significant. In case of combinatorial treatment of JNJ-957 and daratumumab, the expected lysis values were calculated to test the null hypothesis that there is only an additive effect between JNJ-957 and daratumumab, using the following formula: % expected lysis=(% lysis with JNJ-957+% lysis with daratumumab)−(% lysis with JNJ-957 x % lysis with daratumumab), as described before. The null hypothesis of "additive effects" was rejected, if the observed values were significantly higher (P<0.05) than the expected values.

Example 1 Phase 1 study of teclistamab (JNJ-957) administered in combination with subcutaneous daratumumab for relapsed or refractory multiple myeloma (RRMM)

A phase 1b, open-label, multicenter, multi-cohort study of teclistamab in combination with subcutaneous (SC) dosing regimens of daratumumab administered to adult subjects with multiple myeloma was carried out. Two treatment combinations also included pomalidomide (and concomitant dexamethasone for at least the initial cycles). In the pomalidomide-containing treatment combinations, dexamethasone administration was required through the first 3 full immunomodulatory agent (IMiD) containing cycles to enhance IMiD-driven antimyeloma effects and serve as pretreatment medication for daratumumab and teclistamab. An overall aim of the study was to evaluate the safety of daratumumab in combination with teclistamab with or without pomalidomide (and concomitant dexamethasone at least in the initial cycles), and to evaluate preliminary antitumor activity. Safety was monitored by a Study Evaluation Team (SET).

Objectives and Endpoints

TABLE 10

Objectives and endpoints of the phase 1 study of teclistamab (JNJ-957) administered in combination with subcutaneous daratumumab for RRMM.

| Objectives | Endpoints |
|---|---|
| Primary | |
| Part 1: To identify RP2Ds for each treatment combination | Frequency and severity of dose-limiting toxicities |
| Part 2: To characterize the safety of each RP2D for selected treatment combination(s) | Frequency and severity of adverse events and serious adverse events |
| Secondary | |
| To characterize the pharmacokinetics and pharmacodynamics of each study treatment | Serum concentrations and pharmacodynamic markers |
| To assess the immunogenicity of each study treatment | Presence of anti-drug antibodies |
| To evaluate the antitumor activity of each treatment combination | ORR<br>Clinical benefit rate (MR or better)<br>Duration of and time to response |
| Exploratory | |
| To explore relationships between pharmacokinetics, pharmacodynamics, adverse event profile, and clinical activity<br>To investigate predictive biomarkers of response or resistance<br>To investigate the immunoregulatory activity of each treatment combination<br>To evaluate MRD negativity rates<br>To evaluate PFS<br>To evaluate the exposure-response relationship | |

Abbreviations:
MR = minimal response;
MRD = minimal residual disease;
ORR = overall response rate;
PFS = progression-free survival;
RP2D = recommended Phase 2 dose Study Design The study was conducted in 2 parts:

Part 1: dose escalation to establish the RP2D(s) of each treatment combination

Part 2: dose expansion at the RP2D(s) for selected treatment combination(s).

A schematic overview of Part 1 and Part 2 is provided in FIG. 1. The following treatment combinations were studied:
- SC daratumumab and IV teclistamab
- SC daratumumab and SC teclistamab
- SC daratumumab, SC teclistamab, and pomalidomide.

Part 1 (Dose Escalation Part)

In Part 1 (dose escalation), all subjects would receive daratumumab at the approved dose in multiple myeloma. Subjects who receive pomalidomide would receive it at its approved dose or at a lower modified dose, as applicable. For the initial cohort of subjects treated in the study (in which a treatment dose of 270 µg/mg IV teclistamab was evaluated), step-up dosing for the bispecific antibody followed Dosing Schedule A in which step-up dosing began on Cycle 1 Day 9. This cohort utilized the step-up dosing regimen (i.e., dose, number of step-up dose[s], and number of days between step-up dose[s]) and treatment dose associated with the treatment dose level below that last cleared for the appropriate route of administration in the ongoing monotherapy studies (e.g., treatment doses of 270 µg/kg IV teclistamab). Based on emerging data, the SET approved implementing Dosing Schedule B, in which step-up dosing begins on Cycle 1 Day 2. For subsequent cohorts, the SET would determine the step-up dosing regimen and treatment dose based on a statistical model using all available safety, pharmacokinetic, and pharmacodynamic data to identify safe and tolerable RP2D(s). Step-up and treatment doses examined in this study would not exceed those previously cleared by the SET in the monotherapy studies of teclistamab. The relevant treatment dose was planned to be administered on a weekly basis in 28-day cycles following the step-up dose(s); however, other schedules, including biweekly administration, were studied in cohorts as well. At least 30 subjects would be evaluated in Part 1. The total number of subjects enrolled would depend on the number of dose levels explored to identify the RP2D(s) and the number of subjects enrolled at each dose level.

Part 2 (Dose Expansion Part)

The RP2D(s) for each treatment combination selected for further study in Part 2 (NCT04108195CTX) would be based on the dose recommended by BLRM (Bayesian Logistic Regression Model) based on the findings from Part 1. Additionally, the SET would review all available safety, pharmacokinetic, pharmacodynamic, and efficacy data for each treatment combination in Part 1 before determining the RP2D(s) for that treatment combination in Part 2, if applicable. The SET may select 1 or more RP2D(s) for each treatment combination. Up to approximately 40 subjects would be evaluated in each of the RP2Ds for each treatment combination selected for study in Part 2.

Subject Population

The study was conducted on subjects ≥18 years of age with multiple myeloma who had received at least 3 prior lines of therapy, including a proteasome inhibitor (PI) and an IMiD, or who have disease that is double refractory to a PI and an IMiD. Subjects who had received anti-CD38 therapy <90 days were excluded. For subjects who were to be enrolled in a treatment combination that includes pomalidomide, prior IMiD therapy should include lenalidomide.

The inclusion and exclusion criteria for enrolling subjects in this study are described below. All study enrollment criteria have been met at screening and prior to first dose of study drug.

Inclusion Criteria

Each subject was required to satisfy all of the following criteria for enrollment in the study:
1. ≥18 years of age.
2. Documented initial diagnosis of multiple myeloma according to IMWG diagnostic criteria.
3. Must have either of the following:
   Received at least 3 prior lines of therapy (see definition below) including a PI (≥2 cycles or 2 months of treatment) and an IMiD (≥2 cycles or 2 months of treatment) in any order during the treatment (except for subjects who discontinued either of these treatments due to a severe allergic reaction within the first 2 cycles/months).
   Undergone at least 1 complete cycle of treatment for each line of therapy, unless progressive disease was the best response to the line of therapy,
   For prior lines of therapy that did not include a PI and/or IMiD, to meet the criteria for at least prior lines of therapy the subject must have undergone at least 1 complete cycle or month of treatment, unless progressive disease was the best response to the line of therapy, or unless the subject discontinued due to an adverse reaction; or
   Disease that is double refractory to a PI and an IMiD. For subjects who have received more than 1 type of PI, the disease must be refractory to the most recent one. Similarly, for those who have received more than 1 type of IMiD, the disease must be refractory to the most recent one.
   NOTE: Subject must have documented evidence of progressive disease based on investigator's determination of response by the IMWG 2016 criteria as described by Kumar et al. 2016 (Lancet Oncol. 2016;17(8):e328-346.) on or within 12 months of their last line of therapy. Confirmation may be from either central or local testing. Also, subjects with documented evidence of progressive disease (as above) within the previous 6 months and who are refractory or non-responsive to their most recent line of therapy afterwards are eligible.
   NOTE: For subjects who are to be enrolled in a treatment combination that includes pomalidomide, prior IMiD therapy should include lenalidomide.
4. Measurable disease at screening as defined by any of the following:
   Serum monoclonal protein (M-protein) level ≥1.0 g/dL (in non-IgG myeloma, an M-protein level ≥0.5 g/dL); or
   Urine M-protein level 200 mg/24 hours; or
   Light chain multiple myeloma: Serum Ig free light chain (FLC) 10 mg/dL and abnormal serum Ig kappa lambda FLC ratio.
5. Eastern Cooperative Oncology Group (ECOG) performance status grade of 0 or 1 at screening and at Cycle 1, Day 1 predose.
6. Clinical laboratory values meeting the following criteria prior to administration of daratumumab on Cycle 1 Day 1:

TABLE 11

Criteria for clinical laboratory values.

Hematology

| | |
|---|---|
| Hemoglobin | ≥8.0 g/dL (≥5 mmol/L) (without RBC transfusion in the prior 7 days; recombinant human erythropoietin use is permitted) |

TABLE 11-continued

Criteria for clinical laboratory values.

| | |
|---|---|
| Platelets | ≥50 × 10⁹/L (without transfusion support in the prior 7 days) |
| Absolute Neutrophil Count (ANC) | ≥1.0 × 10⁹/L (prior growth factor support is permitted but must be without support for 7 days for G-CSF or GM-CSF or 14 days for pegylated-G-CSF) |

Chemistry

| | |
|---|---|
| Aspartate aminotransferase (AST) and alanine aminotransferase (ALT) | ≤2.5 × ULN |
| Creatinine clearance | ≥30 mL/min/1.73 m² based upon Modified Diet in Renal Disease formula calculation |
| Total bilirubin | ≤1.5 × ULN; except in subjects with congenital bilirubinemia, such as Gilbert syndrome (in which case direct bilirubin ≤1.5 × ULN is required) |
| Serum calcium corrected for albumin | ≤14 mg/dL (≤3.5 mmol/L) or free ionized calcium <6.5 mg/dL (<1.6 mmol/L) |

Abbreviations:
G-CSF = granulocyte colony-stimulating factor;
GM-CSF = granulocyte-macrophage colony-stimulating factor;
ULN = upper level of normal;
RBC = red blood cell 7. Women of childbearing potential must have a negative highly-sensitive serum β human chorionic gonadotropin (β-hCG) pregnancy test (<5 IU/mL) at screening and a negative urine or serum pregnancy test within 24 hours before the first dose of study drug and must agree to further serum or urine pregnancy tests during the study.

8. Women must be either of the following:
   a. Not of childbearing potential
   b. Of childbearing potential and
      practicing true abstinence;
      or have a sole partner who is vasectomized;
      or practicing at least 1 highly effective user independent method of contraception (e.g., intrauterine device (IUD), intrauterine hormone-releasing system (IUS), bilateral tubal ligation/occlusion, or implantable progestogen-only hormone contraception associated with inhibition of ovulation). If hormonal contraception is used (e.g., oral estrogen/progestin), a male or female condom with or without spermicide (e.g., spermicidal foam/gel/film/cream/suppository) must also be used.
      For subjects receiving pomalidomide, women of childbearing potential must be on 2 methods of reliable birth control simultaneously while receiving study treatment and until 100 days after last dose of study treatment: one highlight effective form of contraception (tubal ligation, intrauterine device, hormonal [oral, injectable, transdermal patches, vaginal rings, or implants], or partner's vasectomy), and 1 additional effective contraceptive method (male latex or synthetic condom, diaphragm, or cervical cap).
      For subjects not receiving pomalidomide, a women of childbearing potential using oral contraceptives must use an additional contraceptive method.
   Subject must agree to continue the above while receiving study drug and until 100 days after last dose. Women of childbearing potential must agree to pregnancy testing (serum or urine) within 100 days after the last study drug administration.
Note: If a woman becomes of childbearing potential after start of the study the woman must comply with point (b.) as described above. A woman using oral contraceptives must use an additional contraceptive method in addition to the requirements listed above.

9. Men must wear a condom (with or without spermicidal foam/gel/film/cream/suppository) when engaging in any activity that allows for passage of ejaculate to another person, during the study and for 100 days after the last dose of study drug. His female partner, if of childbearing potential, must also be practicing a highly effective method of contraception (e.g., intrauterine device (IUD), intrauterine hormone-releasing system (IUS), combined (estrogen- and progestogen-containing) hormonal contraception associated with inhibition of ovulation, etc.).
If the male subject is vasectomized, he still must wear a condom (with or without spermicidal foam/gel/film/cream/suppository), but his female partner is not required to use contraception.

10. Women must agree not to donate eggs (ova, oocytes) or freeze for future use, for the purposes of assisted reproduction during the study and for at least 100 days after the last dose of study drug.

11. Men must agree not to donate sperm for the purpose of reproduction during the study and for at least 100 days after receiving the last dose of study drug.

12. Sign an informed consent form (ICF) indicating that he or she understands the purpose of and procedures required for the study and is willing to and able to participate in the study. Consent is to be obtained prior to the initiation of any study related tests or procedures that are not part of standard of care for the subject's disease.

13. Willing and able to adhere to the prohibitions and restrictions specified in this protocol.

Note: A single line of therapy may consist of 1 or more agents, and may include induction, hematopoietic stem cell transplantation, and maintenance therapy. Radiotherapy, bisphosphonate, or a single short course of steroids (i.e., less than or equal to the equivalent of dexamethasone 40 mg/day for 4 days) would not be considered prior lines of therapy.

Exclusion Criteria

Any potential subject who meets any of the following criteria will be excluded from participating in the study:

1. Treatment in the prior 90 days with an anti-CD38 therapy (e.g., daratumumab), or discontinuation of a prior anti-CD38 therapy at any time due to an adverse event related to the anti-CD38 therapy.
2. Prior antitumor therapy as follows, before the first dose of study drug:
Targeted therapy, epigenetic therapy, or treatment with an investigational drug or an invasive medical device within 21 days or at least 5 half-lives, whichever is less.
Monoclonal antibody treatment within 21 days (anti-CD38 treatment cannot be used within the prior 90 days).
Cytotoxic therapy within 21 days.
PI therapy within 14 days.
IMiD therapy within 7 days.
Radiotherapy within 21 days. However, if the radiation portal covered <5% of the bone marrow reserve, the subject is eligible irrespective of the end date of radiotherapy.
Gene modified adoptive cell therapy (e.g., chimeric antigen receptor modified T cells, NK cells) within 90 days.
3. A cumulative dose of corticosteroids equivalent to ≥140 mg of prednisone within the 14-day period before the first dose of study drugs.
4. Live, attenuated vaccine within 4 weeks prior to the first dose of study drug unless approved by sponsor.
5. Toxicity from previous anticancer therapy that has not resolved to baseline levels or to Grade ≤1 (except alopecia [any grade] or peripheral neuropathy Grade ≤3).
6. Stem cell transplantation:
Subjects who received an allogeneic transplant must be off all immunosuppressive medications for ≥42 days without signs of graft-versus-host disease
Autologous stem cell transplantation <12 weeks before the first dose of study drug
7. Active central nervous system involvement or exhibits clinical signs of meningeal involvement of multiple myeloma. If either is suspected, brain magnetic resonance imaging (MRI) and lumbar cytology are required.
8. Active plasma cell leukemia, Waldenstrom's macroglobulinemia, POEMS syndrome (polyneuropathy, organomegaly, endocrinopathy, M-protein, and skin changes), or primary amyloid light chain amyloidosis.
9. Known to be seropositive for human immunodeficiency virus.
10. Seropositive for hepatitis B (defined by a positive test for hepatitis B surface antigen [HBsAg]). Subjects with resolved infection (i.e., subjects who are HBsAg negative with antibodies to total hepatitis B core antigen [Anti-HBc] with or without the presence of hepatitis B surface antibodies [Anti-HBs]) must be screened using real-time polymerase chain reaction (PCR) measurement of HBV DNA levels. Those who are PCR positive will be excluded. EXCEPTION: Subjects with serologic findings suggestive of HBV vaccination (Anti-HBs positivity as the only serologic marker) AND a known history of prior HBV vaccination, do not need to be tested for HBV DNA by PCR.
11. Active hepatitis C infection as measured by positive hepatitis C virus (HCV)-RNA testing. Subjects with a history of Hepatitis C virus antibody positivity must undergo HCV-RNA testing
12. Either of the following:
Chronic obstructive pulmonary disease (COPD) with forced expiratory volume in 1 second (FEV1)<50% of predicted normal. NOTE: FEV1 testing is required for subjects suspected of having COPD and subjects must be excluded if FEV1 is <50% of predicted normal.
Moderate or severe persistent asthma within the past 2 years, or uncontrolled asthma of any classification.

NOTE: subjects who currently have controlled intermittent asthma or controlled mild persistent asthma are allowed to participate in the study.
13. Allergies, hypersensitivity, or intolerance to any study intervention or its excipients (refer to Investigator's Brochures and package inserts).
14. Any serious underlying medical condition, such as:
Evidence of serious active viral, bacterial, or uncontrolled systemic fungal infection
Active autoimmune disease requiring systemic immunosuppressive therapy within 6 months before start of study treatment. EXCEPTION: Participants with vitiligo, type I diabetes, and prior autoimmune thyroiditis that is currently euthyroid based on clinical symptoms and laboratory testing are eligible regardless of when these conditions were diagnosed.
Disabling psychiatric conditions (e.g., alcohol or drug abuse), severe dementia, or altered mental status.
Any other issue that would impair the ability of the subject to receive, absorb, or tolerate the planned treatment at the investigational site, to understand informed consent or any condition for which, in the opinion of the investigator, participation would not be in the best interest of the subject (e.g., compromise the well-being) or that could prevent, limit, or confound the protocol-specified assessments.
15. The following cardiac conditions:
New York Heart Association stage III or IV congestive heart failure
Myocardial infarction or unstable angina <6 months prior to enrollment
History of clinically significant ventricular arrhythmia or unexplained syncope, not believed to be vasovagal in nature or due to dehydration
History of severe non-ischemic cardiomyopathy
Screening 12-lead electrocardiogram (ECG) showing an average baseline QT interval as corrected by Fridericia's formula (QTc) of >470 msec
16. Pregnant or breastfeeding or planning to become pregnant while enrolled in this study or within 100 days after the last dose of study drug.
17. Plans to father a child while enrolled in this study or within 100 days after the last dose of study drug.
18. Major surgery within 2 weeks of the first dose, will not have fully recovered from surgery, or has surgery planned during the time the subject is expected to be treated in the study.
Note: Subjects with planned surgical procedures to be conducted under local anesthesia may participate.
Any potential subject who meets any of the following criteria will be excluded from participating in a treatment combination containing pomalidomide:
19. Subject previously experienced an adverse event related to pomalidomide that required discontinuation of treatment.
NOTE: Investigators should ensure that all study enrollment criteria have been met at screening and prior to first dose of study drug. If a subject's clinical status changes (including any available laboratory results or receipt of additional medical records) after screening but before the first dose of study intervention is given such that the subject no longer meets all eligibility criteria, supportive treatment may be administered according to local standards of care, if necessary, so that eligibility criteria may be met and laboratory test(s) may be repeated once, to determine if the subject qualifies for the study. If inclusion/exclusion criteria are not met after further evaluation, then the subject should be excluded from participation in the study.

Study Interventions

The treatments were administered in 28-day cycles. Daratumumab was administered to all subjects by SC injection at a dose of 1800 mg as follows: weekly in Cycles 1-2, every 2 weeks (Q2W) in Cycles 3, 6, and every 4 weeks thereafter. Note that a recombinant human hyaluronidase PH20 (rHuPH20) was used to decrease the injection volume required, facilitating the SC administration of daratumumab.

Daratumumab SC (Dara) was administered in combination with different dosage levels of teclistamab (Tec), including Dara 1800 mg+Tec 270 µg/kg IV weekly; Dara 1800 mg+Tec 1500 µg/kg SC weekly; Dara 1800 mg+Tec 3000 µg/kg SC weekly; Dara 1800 mg+Tec 300 mg SC biweekly starting Cycle 3 Day 1 (Tec 150 mg SC weekly in Cycles 1-2); Dara 1800 mg+Tec 3000 µg/kg SC biweekly; Dara 1800 mg +Tec 6000 µg/kg (Tec weekly in Cycles 1 and 2, biweekly in Cycles 3-6, and once every four weeks in Cycle 7 and subsequent cycles); Dara 1800 mg+Tec 100 mg weekly in Cycles 1-2, Tec 200 mg biweekly in Cycles 3-7, and Tec 200 mg once every four weeks for Cycle 7 and subsequent cycles (subject must be <60 kg); and Dara 1800 mg+Tec 150 mg weekly in Cycles 1-2, Tec 300 mg biweekly in Cycles 3-7, and Tec 300 mg once every four weeks for Cycle 7 and subsequent cycles (subject must be >60 kg). Some subjects in the Dara 1800 mg+Tec 1500 µg/kg SC weekly cohort switched to Tec 3000 µg/kg biweekly SC dosing after Cycle 3 Day 1. Except for the 270 µg/kg teclistamab IV weekly cohort in which step-up dosing began on Cycle 1 Day 9, step-up doses for teclistamab began on Cycle 1 Day 2. When daratumumab and teclistamab were administered on the same day, daratumumab was administered first. Step-up Dose 1 of teclistamab was administered at least 20 hours after SC daratumumab. Subsequent step-up dose(s), if applicable, and first treatment dose of teclistamab were administered approximately 3 hours after SC daratumumab. Subsequent treatment doses of teclistamab was administered approximately 1 hour after SC daratumumab (when both study drugs are administered on the same day).

For treatments involving a combination of daratumumab SC, teclistamab SC and pomalidomide, 4 mg pomalidomide was orally self-administered once per day. Pomalidomide can be taken before or after study drugs in the treatment combination. To minimize the potential for increased risk of cytokine release syndrome (CRS) with concurrent administration of a bispecific antibody and pomalidomide, the initial cohort of subjects would receive a delayed dosing schedule of pomalidomide. If deemed appropriate by the SET, a decreased starting dose or later start date (e.g., Cycle 2 Day 1 start) could be implemented for pomalidomide for future cohorts, based on a review of safety data for the regimen. Dexamethasone will be given concurrently with the first 3 full IMiD-containing cycles. During the first week of Cycle 1, dexamethasone 20 mg would be given on Cycle 1 Day 1 prior to daratumumab SC and 2 additional doses of dexamethasone 16 mg would be given, 1 each prior to Step-up Dose 1 and Step-up Dose 2 of the bispecific antibody. For the remainder of Cycle 1 and subsequent required cycles, dexamethasone would be given at 40 mg (oral or IV) weekly (except for subjects >75 years of age or who have body mass index [BMI]<18.5, who should receive 20 mg of dexamethasone prior to daratumumab SC administration only). Dexamethasone is given approximately 1 to 3 hours prior to daratumumab SC (or the bispecific antibody on days on which daratumumab SC is not administered). After the required dexamethasone cycles indicated above, the continuation of and the administration schedule for dexamethasone to enhance IMiD-driven antimyeloma effects would be based on the clinical judgment of the investigator. If pomalidomide is permanently discontinued due to toxicity or intolerance, then high dose dexamethasone may also be discontinued based on the clinical judgment of the investigator.

To minimize the potential for increased risk of cytokine release syndrome (CRS) with concurrent administration of a bispecific antibody and pomalidomide, the initial cohort of subjects received a delayed dosing schedule of pomalidomide (C2D1 (cycle 2, day 1) or CID15 (cycle 1, day 15)). The first subject in each cohort in Part 1 was observed for at least 36 hours after the first administration of teclistamab or before treating subsequent subjects at the treatment dose.

The treatment also includes required and optional pretreatment and posttreatment medication associated with SC daratumumab and pomalidomide. The required and optional pretreatment and posttreatment medications for daratumumab can be 2-week Glucocorticoid Taper. It can be, for example, the required treatment with IV or oral glucocorticoid (e.g., methylprednisolone 20 to 100 mg, dexamethasone 4 to 12 mg) before and after daratumumab administration for subjects not receiving pomalidomide; the required IV or oral antihistamine (e.g., diphenhydramine 25 to 50 mg or equivalent) or antipyretic (acetaminophen 650 to 1000 mg) before daratumumab administration for all subjects; and the optional IV or oral glucocorticoid (methylprednisolone 60 mg (or dexamethasone 12 mg), or oral leukotriene inhibitor (e.g., montelukast 10 mg) before daratumumab administration for all subjects. IV or oral glucocorticoid (e.g., dexamethasone, 8 to 16 mg), antihistamine (e.g., diphenhydramine 25 to 50 mg or equivalent) or antipyretic (acetaminophen 650 to 1000 mg) could also be required as pre-treatments for teclistamab, e.g., before all step-up doses and first treatment dose, or for subjects who experience Grade ≥2 CRS/IRR for the next 2 subsequent doses of teclistamab.

For subjects in any treatment combination with a higher risk of respiratory complications (e.g., subjects with mild asthma or subjects with COPD who have an FEV1<80% at screening or developed FEV1<80% during the study without any medical history), the following postinjection medications should be considered: antihistamine, short-acting 32 adrenergic receptor agonist such as salbutamol, control medications for lung disease (e.g., inhaled corticosteroids ±long-acting 32 adrenergic receptor agonists for subjects with asthma; long-acting bronchodilators such as tiotropium or salmeterol ±inhaled corticosteroids for subjects with COPD).

Study Assessments

Safety, pharmacokinetics, immunogenicity, biomarkers, efficacy, and other measurements would be performed.

Safety would be assessed by, e.g., physical examinations (including neurological assessment), Eastern Cooperative Oncology Group (ECOG) performance status, clinical laboratory tests, vital signs, adverse event monitoring, and concomitant medication usage. All adverse events and special reporting situations, whether serious or non-serious, will be reported from the time a signed and dated ICF is obtained until 100 days after the last dose of study drug or until the start of subsequent systemic anticancer therapy, if earlier, and may include contact for follow-up of safety. Adverse events (AEs) are assessed by NCI-CTCAE v5.0, except for cytokine release syndrome (CRS) and immune effector cell-associated neurotoxicity syndrome (ICANS), which were graded per American Society for Transplantation and Cellular Therapy (ASTCT) guidelines. Events of CRS (any grade) must be followed until recovery or until there is no further improvement.

Blood and serum or plasma samples were collected for assessments of pharmacokinetics and immunogenicity (e.g., antibodies to daratumumab, rHuPH20, or teclistamab). Selection of the dose regimen (dose level and frequency) for dose expansion was determined based on the pharmacokinetic and pharmacodynamic information obtained during dose escalation. A sample for the pharmacokinetic and immunogenicity analysis was collected at scheduled time and any time a suspected IRR or CRS event (in case of a CRS event, samples were collected at onset, 24 hours and 72 hours) was observed during the study.

Each serum sample was evenly divided into 3 aliquots (1 for pharmacokinetics and immunogenicity of daratumumab, 1 for pharmacokinetics and immunogenicity of teclistamab, and 1 backup). Each plasma sample for anti-rHuPH20 antibodies were divided into 5 aliquots (3 for anti-rHuPH20 antibodies and 2 for neutralizing antibodies against rHuPH20). Samples collected for analyses of pharmacokinetics and immunogenicity may be used to evaluate sBCMA or to evaluate safety or efficacy aspects that address concerns arising during or after the study period for further characterization of immunogenicity. For the pharmacokinetics analysis, serum samples were analyzed to determine concentrations of daratumumab and teclistamab using validated, specific, and sensitive assay methods. Pharmacokinetic parameters include, but are not limited to, area under the curve $(AUC)_{(0-t)}$, $AUC_{tau}$, $C_{max}$, and $T_{max}$ would be calculated if sufficient data were available for estimation. For immunogenicity analysis, the detection and characterization of antibodies to daratumumab, rHuPH20, and teclistamab were performed using validated assay methods. Positive samples for binding antibodies were tested for neutralizing antibodies to daratumumab or teclistamab. For the rHuPH20 immunogenicity assessments, plasma samples were screened for antibodies binding to rHuPH20 and were assessed in confirmatory and titer assays as necessary.

Biomarker assessments were conducted in both Part 1 and Part 2. The biomarker assessments focused on several main objectives: (1) immune responses indicative of T cell redirection for potential contributions to response to study drug; (2) the ability of each treatment combination to induce MRD negativity in subjects with multiple myeloma who have achieved a CR; (3) serum proteomic profiling of cytokines (such as IL-6, IL-2, and IL-10) or other serum proteins indicative of immune response; (4) biomarkers of response/resistance on myeloma cells (such as BCMA, CD38, and PD-L1); (5) the clinical benefit (ORR, duration of response [DOR], and time to response) of each treatment combination in subjects with cytogenetic modifications (del17p, t(4;14), t(14;16), or other high-risk molecular subtypes); and (6) immunophenotypes of immune cells subsets such as CD4+ and CD8+ T cells, and regulatory T cells that could directly impact the mechanisms of action. Additional biomarker samples could be collected to help understand an unexplained adverse event. Additional sample(s) for cytokines could also be collected any time a suspected IRR or CRS event was observed or reported during the study.

Disease evaluations would be performed by a central laboratory (additional samples may be collected for analysis by the local laboratory) until disease progression. This study would use the IMWG-based response criteria (2016) as described by Kumar et al. (*Lancet Oncol.* 2016;17(8):e328-346.) For subjects with suspected daratumumab interference on serum immunofixation electrophoresis (IFE), a second reflex assay using the anti-idiotype monoclonal antibody will be used to confirm daratumumab migration on the IFE. Subjects that meet all other IMWG criteria for CR, and whose positive IFE is confirmed to be daratumumab interference, are considered complete responders. For subjects with light chain multiple myeloma, both serum and urine IFE and serum FLC assay would be performed every 4 weeks. Additional serum samples may be utilized to monitor for potential daratumumab interference with the IFE and response adjudicated per IMWG-based response criteria. Quantitative immunoglobulin (QIg, e.g., IgG, IgA, IgM, IgE, and IgD), M-protein by electrophoresis (SPEP), FLC and IFE measurements in serum and urine and serum β-microglobulin would be analyzed by the central laboratory. Disease progression based on one of the laboratory tests alone must be confirmed by at least 1 repeat investigation performed 1 to 3 weeks later. Disease evaluations would continue beyond relapse from CR until disease progression was confirmed. Serum and urine IFE and serum FLC assays would be performed at screening and thereafter when a CR or sCR is suspected (when serum or 24-hour urine M-protein electrophoresis [by SPEP or UPEP] are 0 or non-quantifiable). Development of hypercalcemia (corrected serum calcium >11 mg/dL) may indicate disease progression or relapse if it is not attributable to any other cause. Thus, corrected serum calcium or free ionized calcium was also analyzed in blood samples until the development of confirmed disease progression.

Bone marrow aspirate or biopsy would be performed for clinical assessments and biomarker evaluations. Clinical staging (morphology, cytogenetics, and immunohistochemistry or immunofluorescence or flow cytometry) may be done by a local laboratory. A portion of the bone marrow aspirate was used for immunophenotyping and to monitor BCMA, CD38, and checkpoint ligand expression in CD138-positive multiple myeloma cells, and checkpoint expression on T cells. A bone marrow aspirate sample was required to confirm CR and sCR before the next scheduled dose of study drug. MRD negativity is being evaluated in the field as a potential surrogate for progression-free survival (PFS) and OS. Baseline bone marrow aspirates was used to define the myeloma clones, and posttreatment samples will be used evaluate MRD negativity in those subjects who experience a CR/sCR. Bone marrow aspirate DNA can be used to monitor MRD using next generation sequencing, while serum MRD negativity will be assessed via mass spectrometry.

A complete skeletal survey (including skull, entire vertebral column, pelvis, chest, humeri, femora, and any other bones for which the investigator suspects involvement by disease) was performed during the screening period and evaluated by either roentgenography or low-dose computed tomography (CT) scans (or positron emission tomography [PET]/CT) without the use of IV contrast. The same methodology that was used at baseline should be used when assessing for progression during the treatment period. MRI may also be included for evaluation of bone disease.

Statistical Analysis

No formal statistical hypothesis testing was conducted in this study. Part 1 (dose escalation) would be supported by a modified continual reassessment method (mCRM) based on a statistical model, Bayesian Logistic Regression Model (BLRM), with Escalation with Overdose Control (EWOC) principle. One or more RP2D(s) for each treatment combination may be identified. In Part 2 (dose expansion), subjects would be treated at each RP2D(s) to further assess the safety and antitumor activity of selected treatment combination(s).

Endpoint Definitions

ORR is defined as the proportion of subjects who have a PR or better according to the IMWG criteria. Response to treatment will be evaluated by investigator.

Clinical benefit rate (ORR+MR) is defined as the proportion of subjects who have a MR or better according to the IMWG criteria, as evaluated by investigator.

MRD negativity rate is defined as the proportion of subjects who achieve MRD negative status.

DOR is defined as the time from the date of initial documentation of a response (PR or better) to the date of first documented evidence of progressive disease, as defined in the IMWG criteria or death due to progressive disease, whichever occurs first. Relapse from CR is not considered as disease progression. For subjects who have not progressed, data will be censored at the last disease evaluation before the start of any subsequent antimyeloma therapy.

Time to response is defined as the time between date of first dose of study drug and the first efficacy evaluation that the subject has met all criteria for PR or better.

PFS is defined as the time from the date of first dose of study drug to the date of first documented disease progression, as defined in the IMWG criteria, or death due to any cause, whichever occurs first. For subjects who have not progressed and are alive, data will be censored at the last disease evaluation before the start of any subsequent antimyeloma therapy.

Preliminary Results for weight-based cohorts (Cut-off Date for Analyses Apr. 6, 2022)

The study is ongoing and as of the cut-off date for the analysis, 65 patients treated with teclistamab and daratumumab were evaluated.

Teclistamab SC (1.5 mg/kg QW and 3.0 mg/kg Q2W)+ Daratumumab SC Cohorts

SC treatment with daratumumab and teclistamab was administered in 28-day cycles (with step-up dosing for teclistamab). Preliminary data as of Apr. 6, 2022, included results for 65 subjects treated with 1800 mg SC daratumumab and teclistamab (1.5 mg/kg (1500 µg/kg) weekly+3 mg/kg (3000 µg/kg) weekly or biweekly). A summary of the teclistamab and daratumumab dosing cohorts is shown in Table 12.

TABLE 12

Teclistamab and Daratumumab Dosing Cohorts (n = 65).

| Teclistamab[a] | Daratumumab SC | Patients enrolled to date (n) |
|---|---|---|
| 1.5 mg/kg SC QW | 1800 mg SC | 21 |
| 3 mg/kg SC Q2W | Cycles 1-2: QW | 39 |
| 3 mg/kg SC QW | Cycles 3-6: Q2W | 5 |
| | Cycles 7+: monthly | |

[a]Step-up dosing was used for teclistamab (including a PI and IMiD) and 1-3 step-up doses were given within 1 week before the full dose. Note: Nine patients were switched from 1.5 mg/kg SC QW to 3 mg/kg SC Q2W in Cycles 4-9. Premedications (glucocorticoid, antihistamine, and antipyretic) were limited to the step-up dose and first full dose of teclistamab. There were no steroid requirements for teclistamab after the first full dose.

IMiD, immunomodulatory drug; PI, proteasome inhibitor; QW, once weekly; Q2W, once every 2 weeks Median age range for the 65 subjects evaluated was 67 years (range 40-81) and 30 subjects were female (46.2%). Median number of prior therapies was 5 (range 1-15), 80% of subjects were refractory to last line of therapy, 58.5% triple-class refractory, 55.4% penta-drug exposed, and 30.8% penta-drug refractory. A summary of the subjects' demographics and baseline characteristics is shown in Table 13.

TABLE 13

Patient demographics and baseline characteristics.

| Characteristic | Dara + Tec[a] (n = 65) |
|---|---|
| Age, median (range), years | 67 (40-81) |
| Female, n % | 30 (46.2) |
| Male, n % | 35 (53.8) |
| Race, n (%) | |
| White | 53 (81.5) |
| Black/African American | 4 (6.2) |
| Other[b] | 8 (12.3) |
| Extramedullary plasmacytomas ≥1[c], n (%) | 15 (23.1) |
| High cytogenic risk[d], n (%) | 7 (25.9) |
| ISS stage[e], n (%) | |
| I | 30 (55.6) |
| II | 11 (20.4) |
| III | 13 (24.1) |
| Time since diagnosis, years, median (range) | 6.6 (0.7-20.9) |
| Prior lines of therapy, n, median (range) | 5 (1-15) |
| Prior stem cell transplantation, n (%) | 47 (72.3) |
| Exposure status, n (%) | |
| Prior BCMA therapy[f] | 8 (12.3) |
| Anti-CD38[g] | 49 (75.4) |
| IMiD[h] | 65 (100.0) |
| Triple-class[i] | 49 (75.4) |
| Penta-drug[j] | 36 (55.4) |
| Refractory status, n (%) | |
| Anti-CD38[g] | 41 (63.1) |
| IMiD[h] | 54 (83.1) |
| Triple-class[i] | 38 (58.5) |

TABLE 13-continued

Patient demographics and baseline characteristics.

| Characteristic | Dara + Tec[a] (n = 65) |
|---|---|
| Penta-drug[j] | 20 (30.8) |
| To last line of therapy | 52 (80.0) |

[a]Daratumumab SC 1800 mg plus teclistamab SC (1.5 mg/kg QW or 3 mg/kg QW or 3 mg/kg Q2W)
[b]includes one patient reported as Asian and patients whose race was not reported
[c]Soft-tissue plasmacytomas not associated with the bone were included;
[d]del(17p), t(4: 14), and/or t(14; 16); percentages calculated from n = 48;
[e]Percentages calculated from n = 54;
[f]BCMA CAR-T therapy or BCMA non-CAR-T therapy;
[g]Daratumumab or isatuximab;
[h]Thalidomide, lenalidomide, and/or pomalidomide;
[i]≥1 PI, ≥1 IMiD, and ≥1 anti-CD38 mAb;
[j]≥2 PI, ≥2 IMiD, and ≥1 anti-CD38 mAb;
BCMA, B-cell maturation antigen;
CAR-T, chimeric antigen T cell;
IMiD, immunomodulatory drug;
ISS, International Staging System;
PI, proteasome inhibitor;
QW, weekly;
Q2W, every other week;
SC, subcutaneous;
mAb, monoclonal antibody The combination of teclistamab and daratumumab exhibited a manageable safety profile that was well tolerated, with no new safety signals observed compared to single agents and no overlapping toxicities. No treatment discontinuations occurred due to AEs and there were no observed overlapping toxicities. All CRS events were limited to grade 1 or 2. Infections occurred in 44 (67.7%) patients (grade ≥3: 27.7%). One patient (1.5%) had a grade 1 ICANS event, which fully resolved in 1 day. Most common all-grade hematologic AEs were neutropenia (49.2% at any grade, 41.5% at grade 3 or 4), anemia (41.5% at any grade, 27.7% at grade 3 or 4), and thrombocytopenia (32.3% at any grade, 24.6% at grade 3 or 4). Most common all-grade nonhematologic AEs were CRS (67.7% at any grade, 0 at grade 3 or 4), diarrhea (32.3% at any grade, 1.5% at grade 3 or 4), nausea (27.7% at any grade, 0 at grade 3 or 4), and asthenia (20.0% at any grade, 1.5% at grade 3 or 4). A summary of the AEs for patients treated with teclistamab and daratumumab is shown in Table 14.

TABLE 14

Adverse events (AEs). Teclistamab + Daratumumab[a] SC (n = 65)

| AE (≥20%), n (%) | Any Grade | Grade 3/4 |
|---|---|---|
| Hematologic | | |
| Neutropenia | 32 (49.2) | 27 (41.5) |
| Anemia | 27 (41.5) | 18 (27.7) |
| Thrombocytopenia | 21 (32.3) | 16 (24.6) |
| Nonhematologic | | |
| CRS | 44 (67.7) | 0 (0) |
| Diarrhea | 21 (32.3) | 1 (1.5) |
| Nausea | 18 (27.7) | 0 (0) |
| Asthenia | 13 (20.0) | 1 (1.5) |
| Fatigue | 19 (29.2) | 2 (3.1) |
| Pyrexia | 19 (29.2) | 0 (0) |
| Headache | 13 (20.0) | 1 (1.5) |
| Decreased appetite | 13 (20.0) | 0 |

[a]Daratumumab SC 1800 mg + teclistamab SC (1.5 mg/kg QW or 3 mg/kg QW or 3 mg/kg Q2W).
QW, weekly; Q2W, every other week; SC, subcutaneous; CRS, cytokine release syndrome; ICANs, immune effector cell-associated neurotoxicity syndrome; AEs were graded by CTCAE v 5 with CRS and ICANS events graded per American Society for Transplantation and Cellular Therapy 2019 criteria; AE: adverse event.

There were 51 response evaluable subjects. The overall response rate (ORR) was improved compared to the recommended phase 2 dose for teclistamab monotherapy. The ORR for patients (n=27) treated with daratumumab SC 1800 mg and teclistamab SC Q2W 3 mg/kg was 74.1%. The ORR for patients (n=20) treated with daratumumab SC 1800 mg and teclistamab SC QW 1.5 mg/kg was 75.0%. The ORR for patients (n=4) treated with daratumumab SC 1800 mg and teclistamab SC 3 mg/kg was 100%. The median follow-up time was 8.6 months (range: 0.3-19.6) and the median time to first confirmed response was 1 month (range: 0.9-3.5). A summary of the ORRs is shown in Table 15.

TABLE 15

Overall response rates (ORRs) in response evaluable subjects (n = 51).
Evaluable patients[a], (n = 51)

| | Daratumumab 1800 mg SC: Cycles 1-2; QW, Cycles 3-6; Q2W, Cycles 7+: Monthly | | |
|---|---|---|---|
| Response Categories | Tec SC Q2W 3 mg/kg (n = 27) | Tec SC QW 1.5 mg/kg (n = 20) | Tec SC QW 3 mg/kg (n = 4) |
| ORR[b] | 20 (74.1) | 15 (75.0) | 4 (100.0) |
| CR/sCR | 3 (11.1) | 6 (30.0) | 2 (50.0) |
| VGPR | 15 (55.6) | 8 (40.0) | 2 (50.0) |
| PR | 2 (7.4) | 1 (5.0) | 0 (0) |
| SD | 5 (18.5) | 3 (15.0) | 0 (0) |
| PD | 2 (7.4) | 2 (10.0) | 0 (0) |

[a]Patients have received at least one study treatment and have at least one postbaseline response evaluation by investigator; includes unconfirmed responses;
[b]PR or better in response-evaluable patients, includes unconfirmed responses;
CR, complete response; ORR, overall response rate; PR, partial response; QW, weekly; Q2W, every other week; SC, subcutaneous; SD, stable disease; PD, progressive disease; RP2D, recommended phase 2 dose; tec, teclistamab; VGPR, very good partial response.

Figure 2:
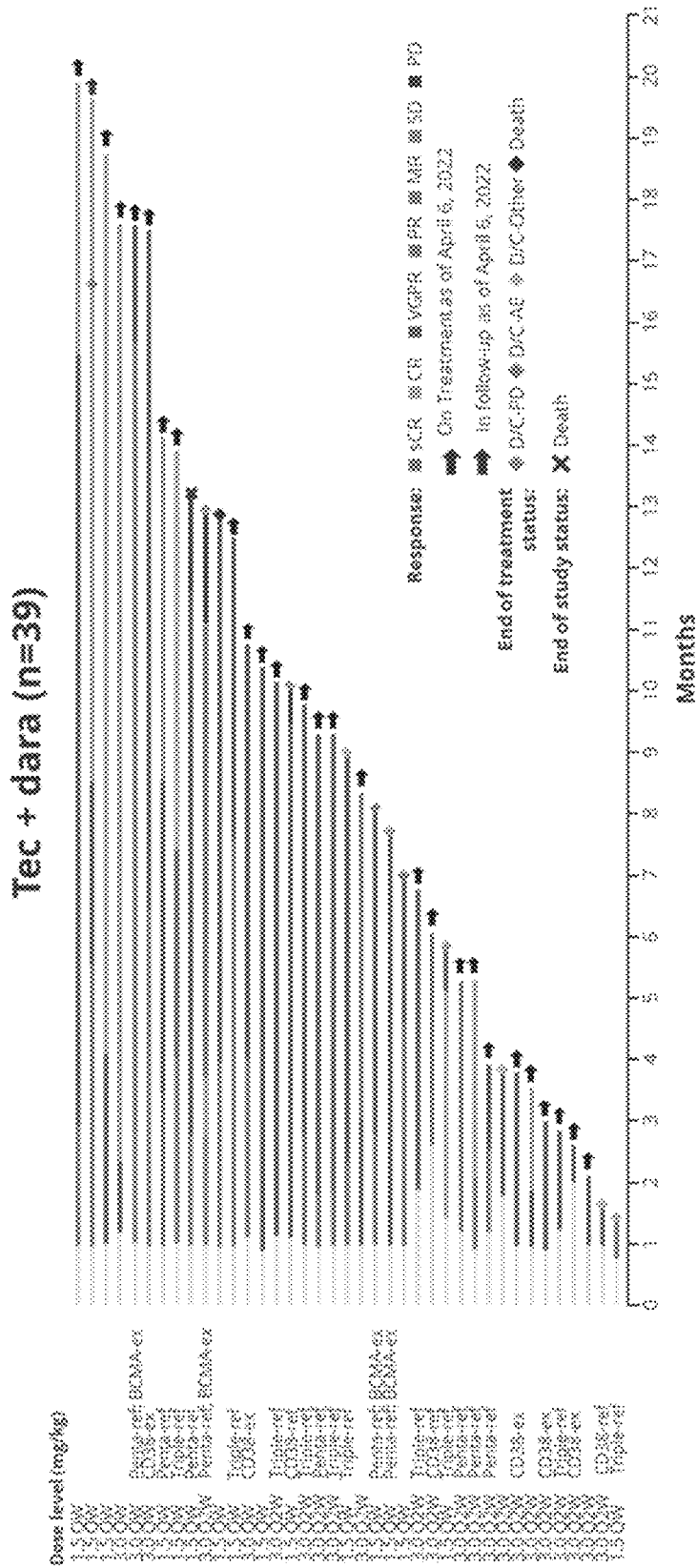
FIG. 2 shows response rates of patients treated with daratumumab and teclistamab in Part 1 and Part 2 of the study (cut-off date for the analysis Apr. 6, 2022). Dara SC 1800 mg+Tec SC (1.5 mg/kg QW or 3 mg/kg QW or 3 mg/kg Q2W); CR, complete response; D/C, discontinued; dara, daratumumab; MR, minimal response; PD, progressive disease; PR, partial response; QW, weekly; Q2W, every other week; sCR, stringent complete response; SD, stable disease; tec, teclistamab; TR, triple-class refractory; VGPR, very good partial response.

The responses were durable and deepened over time as shown in FIG. 2. Responses were observed in heavily pretreated patients, including those who were either CD38 exposed or refractory. The median follow-up time for responders was 9.6 months (range 1.5-19.6) and 26 responses were ongoing treatment at time of cutoff. In addition, there was one participant who at time of cutoff continued response after discontinuing treatment due to an adverse event.

A detailed summary of the overall response rate for patients treated with 1800 mg daratumumab and teclistamab (1500 µg/kg or 3000 µg/kg weekly and 300 mg and 3000 µg/kg biweekly) in combination with daratumumab with or without pomalidomide is shown in Table 16. Sixty-three participants across all teclistamab dose levels had ≥1 post dose disease evaluation as of Apr. 6, 2022 (i.e., were evaluable for efficacy). Patients receiving 300 mg SC teclistamab biweekly in combination with 1800 mg daratumumab SC were treated weekly starting on cycle 1 day 15 through cycle 2 followed by biweekly starting on cycle 3 day 1 (C3D1). Patients receiving 3000 µg/kg SC teclistamab biweekly in combination with 1800 mg daratumumab were treated biweekly starting on cycle 1 day 15. Patients receiving 720 µg/kg or 750 µg/kg SC teclistamab weekly in combination with 1800 mg SC daratumumab and 2 or 4 mg of pomalidomide were treated weekly starting on cycle 1 day 15.

TABLE 16

Summary of overall best response based on Investigator Assessment (response evaluable subjects by investigators) for indicated cohorts.
Summary of Overall Best Response based on Investigator Assessment; Response Evaluable Subjects by Investigators

| | teclistamab | | | | | | | | | |
|---|---|---|---|---|---|---|---|---|---|---|
| | SC QW | | | | SC Q2W | | SC QW (C1-C2)/Q2W (C3-C6)/Q4W | | IV QW | |
| | Tec 1500 µg/kg + Dara 1800 mg | Tec 3000 µg/kg + Dara 1800 mg | Tec 720 µg/kg + Dara 1800 mg + Pom 4 mg | Tec 750 µg/kg + Dara 1800 mg + Pom 2 mg | Tec 300 mg + Dara 1800 mg | Tec 3000 µg/kg + Dara 1800 mg | Tec 6000 µg/kg + Dara 1800 mg | Total Tec SC | Tec 270 µg/kg + Dara 1800 mg | Total Tec |
| Analysis set: Response evaluable subjects by investigators Response category | 20 | 4 | 9 | 1 | 2 | 27 | 10 | 73 | 5 | 78 |
| Stringent complete response (sCR) | 0 | 1 (25.0%) | 2 (22.2%) | 0 | 0 | 1 (3.7%) | 0 | 4 (5.5%) | 0 | 4 (5.1%) |
| Unconfirmed | 0 | 0 | 0 | 0 | 0 | 0 | 0 | 0 | 0 | 0 |
| Complete response (CR) | 6 (30.0%) | 1 (25.0%) | 3 (33.3%) | 0 | 0 | 2 (7.4%) | 1 (10.0%) | 13 (17.8%) | 1 (20.0%) | 14 (17.9%) |
| Unconfirmed | 0 | 0 | 0 | 0 | 0 | 1 | 0 | 1 | 0 | 1 |
| Very good partial response (VGPR) | 8 (40.0%) | 2 (50.0%) | 2 (22.2%) | 0 | 2 (100.0%) | 15 (55.6%) | 6 (60.0%) | 35 (47.9%) | 0 | 35 (44.9%) |
| Unconfirmed | 0 | 0 | 0 | 0 | 1 | 4 | 1 | 6 | 0 | 6 |
| Partial response (PR) | 1 (5.0%) | 0 | 0 | 0 | 0 | 2 (7.4%) | 1 (10.0%) | 4 (5.5%) | 0 | 4 (5.1%) |
| Unconfirmed | 1 | 0 | 0 | 0 | 0 | 1 | 1 | 3 | 0 | 3 |
| Minimal response (MR) | 0 | 0 | 0 | 0 | 0 | 0 | 0 | 0 | 0 | 0 |
| Stable disease (SD) | 3 (15.0%) | 0 | 0 | 1 (100.0%) | 0 | 5 (18.5%) | 2 (20.0%) | 11 (15.1%) | 3 (60.0%) | 14 (17.9%) |
| Progressive disease (PD) | 2 (10.0%) | 0 | 2 (22.2%) | 0 | 0 | 2 (7.4%) | 0 | 6 (8.2%) | 1 (20.0%) | 7 (9.0%) |
| Not evaluable (NE) | 0 | 0 | 0 | 0 | 0 | 0 | 0 | 0 | 0 | 0 |
| Overall response (sCR + CR + VCPR + PR) | 15 (75.0%) | 4 (100.0%) | 7 (77.8%) | 0 | 2 (100.0%) | 20 (74.1%) | 8 (80.0%) | 56 (76.7%) | 1 (20.0%) | 57 (73.1%) |
| Clinical benefit (Overall response + MR) | 15 (75.0%) | 4 (100.0%) | 7 (77.8%) | 0 | 2 (100.0%) | 20 (74.1%) | 8 (80.0%) | 56 (76.7%) | 1 (20.0%) | 57 (73.1%) |
| VGPR or better (sCR + CR + VGPR) | 14 (70.0%) | 4 (100.0%) | 7 (77.8%) | 0 | 2 (100.0%) | 18 (66.7%) | 7 (70.0%) | 52 (71.2%) | 1 (20.0%) | 53 (67.9%) |
| CR or better (sCR + CR) | 6 (30.0%) | 2 (50.0%) | 5 (55.6%) | 0 | 0 | 3 (11.1%) | 1 (10.0%) | 17 (23.3%) | 1 (20.0%) | 18 (23.1%) |

Keys: Dara = daratumumab, IV = intravenous, QW = weekly, Q2W = biweekly, Q4W = every 4 weeks, SC = subcutaneous, Tec = teclistamab, Pom = pomalidomide.
Response evaluable subjects by investigators: Subjects have received at least one study treatment and have at least one post-baseline response evaluation by investigator.
Note:
Response was assessed by investigators, based on IMWG Criteria. Confirmed response require at least two consecutive identical investigators' response assessments.
Unconfirmed responders do not have two consecutive investigators' response assessments to confirm the response at the time of this data review.
Percentages are calculated with the number of subjects in each group as denominator.

For subjects who received 3000 μg/kg SC teclistamab weekly in combination with 1800 mg SC daratumumab (n=4 evaluable subjects), the responses included 2 subjects (50.0%) with a CR/sCR and 2 subjects (50.0%) with a VGPR. For subjects who received 720 μg/kg SC teclistamab weekly in combination with 1800 mg SC daratumumab and 4 mg of pomalidomide (n=9 response evaluable subjects), the responses include 2 subjects with a sCR (22.2%), 3 subjects with a CR (33.3%), 2 subjects with a VGPR (22.2%), 1 subject with a PR (11.1%), and 2 subjects with progressive disease (22.2%). There was one response evaluable subject who received 750 μg/kg SC teclistamab weekly in combination with 1800 mg SC daratumumab and 2 mg of pomalidomide with SD. For subjects who received 300 mg SC teclistamab biweekly in combination with 1800 mg SC daratumumab (n=2 response evaluable subjects), the responses include 2 subjects with VGPR (100%).

Figure 3:
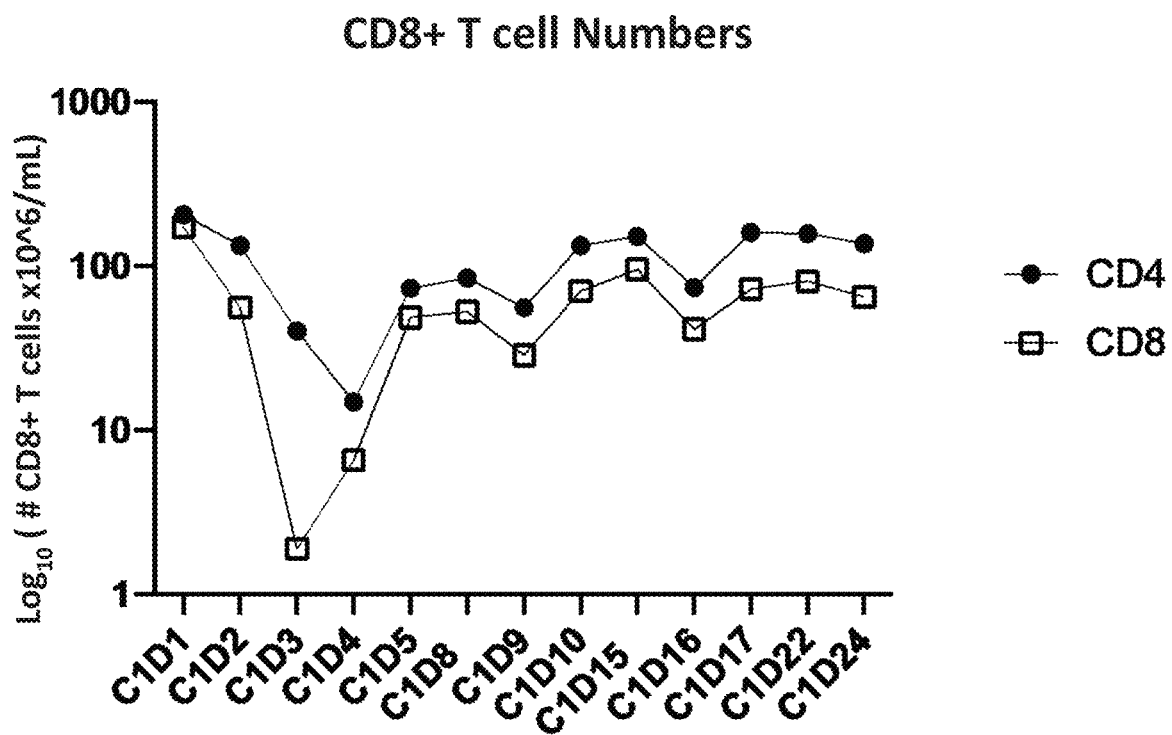
FIG. 3 shows CD8+ and CD4+ T cell numbers in a patient with RRMM treated weekly with 1800 mg SC daratumumab and 1.5 mg/kg SC teclistamab according to an embodiment of the application.
Figure 4:
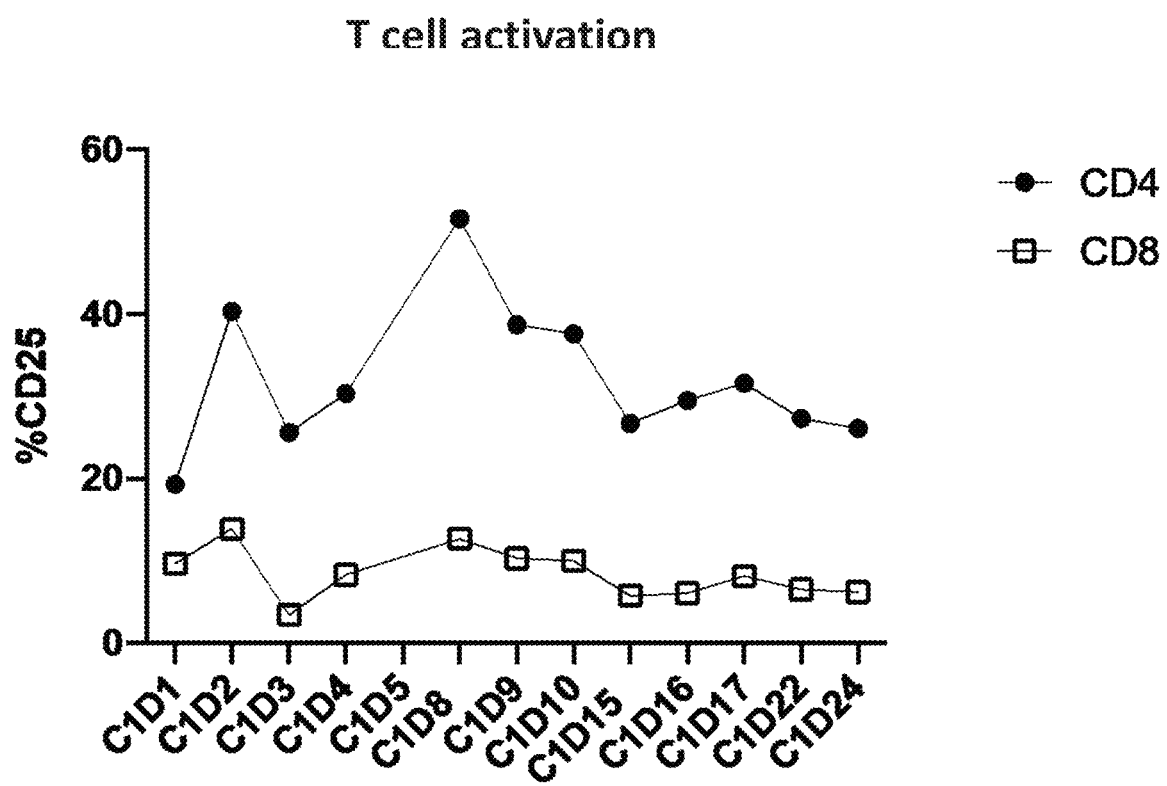
FIG. 4 shows T cell activation (CD25+) in a patient with RRMM treated weekly with 1800 mg SC daratumumab and SC teclistamab according to an embodiment of the application.
Figure 5:
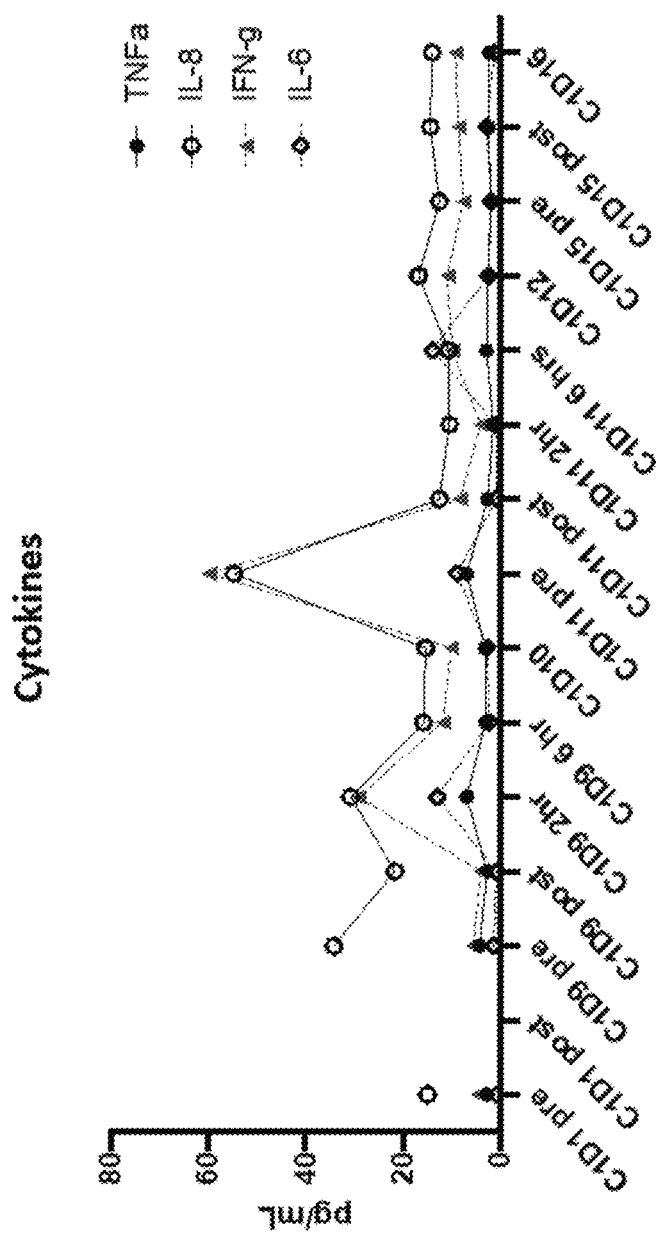
FIG. 5 shows cytokine induction in a patient with RRMM treated weekly with 1800 mg SC daratumumab and SC teclistamab according to an embodiment of the application. TNF-α=tumor necrosis factor-alpha; IL-8=interleukin-8; IFN-g=interferon-gamma; IL-6=interleukin-6.

Biomarker data indicated that the pharmacodynamic profile of teclistamab in the presence of daratumumab was consistent with the mechanism of action of these agents and with the profile observed in the teclistamab monotherapy trial (MajesTEC-1). As of the cut-off date for the biomarker analysis (Apr. 6, 2022), biomarkers were evaluated for 35 subjects [1500 μg/kg QW (n=21) and 3000 μg/kg QW (n=5); 3000 ptg/kg Q2W (n=9)]). There was a transient reduction in T cell numbers early after teclistamab and daratumumab dosing, which was followed by recovery in T cell numbers within one week (FIG. 3). There was also a 2-fold expansion in T cell numbers by Cycle 3 Day 1 (C3D1). Moreover, T cell activation was induced by teclistamab combination with daratumumab (FIG. 4). Induction of pro-inflammatory cytokines occurred following daratumumab and teclistamab (step-up and full dose) treatment (FIG. 5). In two subjects, CD38+ T cell subsets decreases after the first dose of daratumumab.

Figure 6:
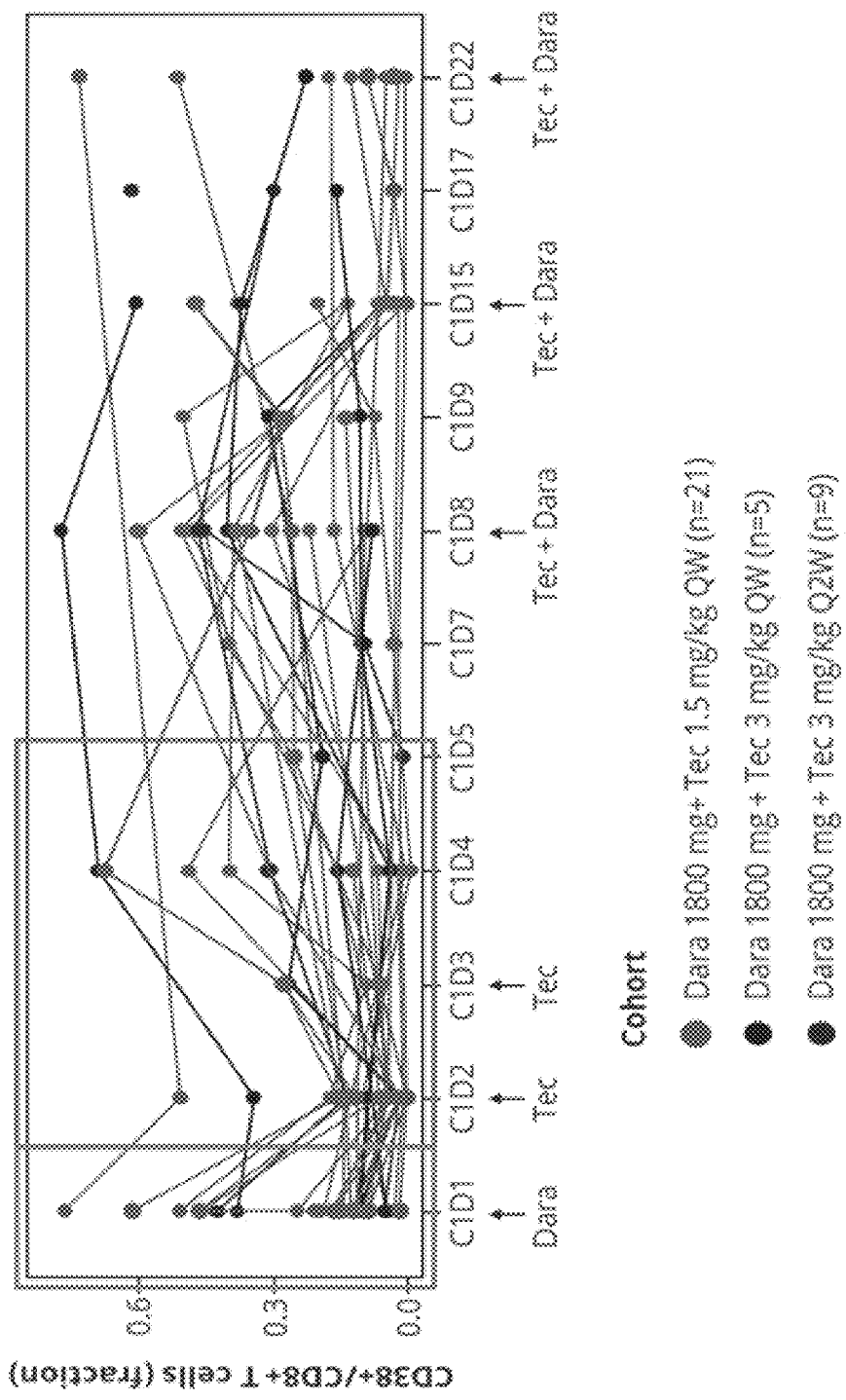
FIG. 6 shows increases in frequency of CD38+ T cells in four subjects with RRMM treated with 1800 mg SC daratumumab and SC teclistamab according to an embodiment of the application.

Teclistamab plus daratumumab administration led to peripheral T cell activation as demonstrated by induction of CD38+/CD8+ T cells (FIG. 6). The proportion of CD38+/CD8+ T cells declined after initial daratumumab dosing on Cycle 1 Day 1 (C1D1), which was consistent with previous data, but notably teclistamab administration led to induction of CD38+ T cells after the first step-up dose of teclistamab (C1D2).

Teclistamab SC (6.0 mg/kg)+Daratumumab SC Cohorts

SC treatment with daratumumab and teclistamab was administered in 28-day cycles (with step-up dosing for teclistamab). Preliminary data as of Apr. 6, 2022, included results for 12 subjects treated with 1800 mg SC daratumumab and teclistamab 6.0 mg/kg (6000 μg/kg). A summary of the teclistamab and daratumumab dosing cohorts is shown in Table 17

The median number of prior lines of therapy was 6.0 (range, 2-15 lines), and median duration of follow-up was 5.39 months (range 1.0-6.0 months). Participants had received a median of 2.0 cycles of Tec-Dara treatment (range: 1-4 cycles). Two participants had discontinued treatment due to death. One of these participants died due to grade 5 Hemophagocytic Syndrome (related to both study drugs) and the other participant died due to COVID-19 pneumonia (not related to study drugs. One participant discontinued study treatment due to a TEAE of grade 4 COVID-19 pneumonia and subsequently died due to grade 5 COVID-19 Pneumonia.

All participants (100.0%) experienced ≥1 TEAE. Four participants (33.3%) experienced any TEAE with maximum severity of Grade 3; 5 participants (41.7%) experienced any TEAE with maximum severity of Grade 4. Two participants had a Grade 5 TEAE. Seven participants (58.3%) reported serious TEAEs. One participant experienced a DLT of grade 5 fatal Hemophagocytic Syndrome.

The most frequently reported TEAEs (≥20% of participants) were fatigue (75%; all Grade 1 or 2) CRS (58.3%; all Grade 1 or 2), neutropenia (58,3%; Grade 3/4: 50%), decreased appetite (50%; all Grade 1 or 2), Cytomegalovirus infection reactivation (41.7%; Grade 3/4: 25%), pyrexia, nausea and diarrhea (all 41.7%; all Grade 1 or 2), Chills (33.3%; all Grade 1 or 2), dry mouth, dyspnoea, weight decreased, vomiting, hypocalcaemia and dysgeusia (25%; all Grade 1 or 2), hypokalaemia (25%; Grade 3/4: 8.3%) and anaemia (25%; Grade 3/4: 16.7%). ICANS was not reported. Four participants (33.3%) experienced a local injection-site reaction; none experienced systemic infusion/injection-related reactions.

Overall, the data for the Phase 1b study was promising as preliminary efficacy data suggested promising ORRs (70-100%) in heavily pretreated patients. Moreover, the teclistamab-mediated induction of cytotoxic T cells (CD38+/CD8+) in the presence of daratumumab supports the rationale for the combination regimen. Consequently, further investigation of the combination of teclistamab and daratumumab in patients with RRMM is warranted. For instance, a randomized phase 3 MajesTEC-3 trial (NCT05083169) will evaluate patients with RRMM treated with teclistamab and daratumumab SC (Tec-Dara) versus daratumumab SC, pomalidomide, and dexamethasone (DPd), or daratumumab, bortezomib, and dexamethasone (DVd).

Example 2 Phase 3 randomized study comparing teclistamab in combination with daratumumab SC (Tec-Dara) versus daratumumab SC, pomalidomide, and dexamethasone (DPd) or daratumumab SC, bortezomib, and dexamethasone (DVd) in participants with RRMM

TABLE 17

Dosing Schedule

| | | |
|---|---|---|
| Teclistamab SC (28-day cycle) | Cycle 1 | Step-up Dose 1: 60 μg/kg on Day 2<br>Step-up dose 2: 300 μg/kg on Day 4<br>Step-up dose 3: 1500 μg/kg on Day 8<br>Treatment Dose: 6000 μg/kg (Days 15, 22) |
| | Cycle 2 | Treatment Dose: 6000 μg/kg (Days 1, 8, 15, 22) |
| | Cycles 3-6 | Treatment Dose: 6000 μg/kg (Days 1, 15) |
| | Cycles 7+ | Treatment Dose: 6000 μg/kg (Day 1) |
| Daratumumab SC (28-day cycle) | Cycles 1-2 | 1800 mg (Days 1, 8, 15, 22) |
| | Cycles 3-6 | 1800 mg (Days 1, 15) |
| | Cycles 7+ | 1800 mg (Day 1) |

A phase 3 randomized study will be conducted comparing teclistamab in combination with daratumumab SC (Tec-Dara) versus daratumumab SC, pomalidomide, and dexamethasone (DPd) or daratumumab SC, bortezomib, and dexamethasone (DVd) in participants with relapsed or refractory multiple myeloma (RRMM). The participants must have received 1 to 3 prior lines of prior therapy, including a PI and lenalidomide.

Objective and Endpoints

Figure 7:
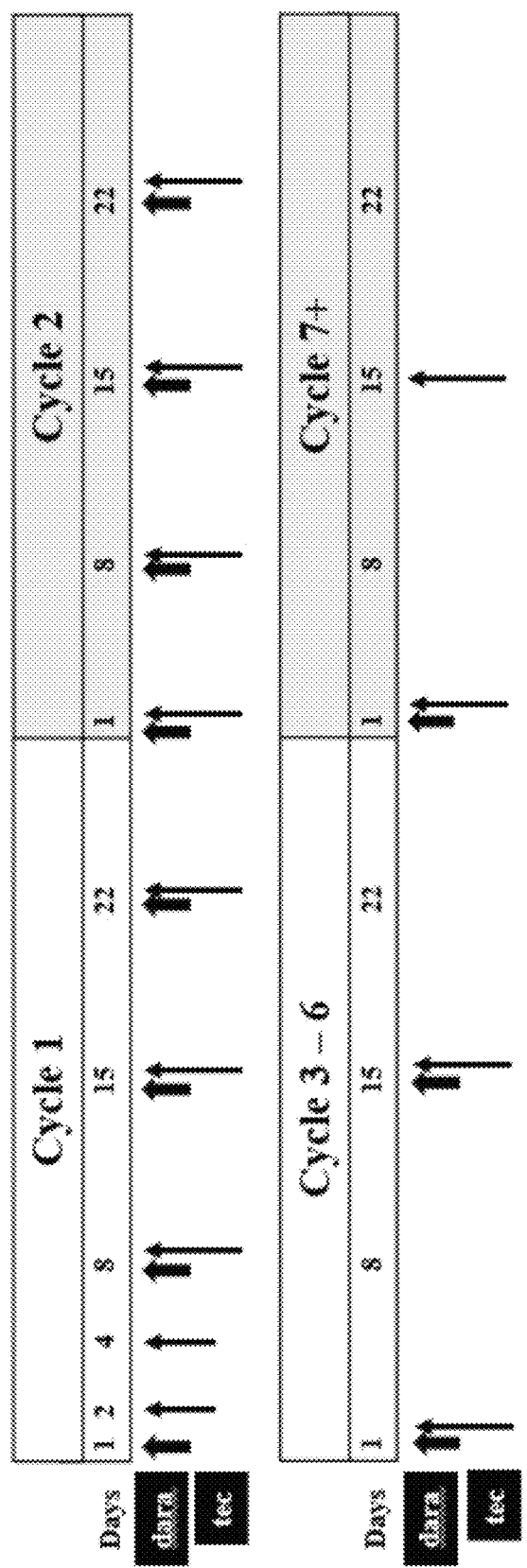
FIG. 7 is a Schematic of Dose Schedule of Arm A (Tec-Dara) of a clinical study according to an embodiment of the application, where the thicker arrow indicates a daratumumab SC dosing day and a thinner arrow indicates a teclistamab dosing day (the shorter of which are step-up doses). Dara, daratumumab; Tec, teclistamab.

The primary objective of the study is to compare the efficacy of teclistamab in combination with daratumumab SC (Tec-Dara; Arm A, FIG. 7) with that of an investigator's choice of DPd or DVd (Arm B; termed DPd/DVd hereafter) as assessed by PFS. Key secondary objectives include further comparison of efficacy as assessed by overall response (PR or better) rate, CR or better rate, MRD (minimal residual disease) —negativity rate, PFS2 (progression-free survival on next-line therapy), and OS (overall survival). The study will be conducted in 3 phases for each participant: Screening (up to 28 days), Treatment (until confirmed progressive disease, death, intolerable toxicity, withdrawal of consent, or end of the study, whichever occurs first), and Follow-up (until death, withdrawal of consent, loss to follow-up, or end of the study, whichever occurs first). Participants who discontinue study treatment for any reason other than progressive disease or withdrawal of consent will continue to be followed for response assessment until confirmed progressive disease or start of subsequent antimyeloma therapy. After confirmed progressive disease, participants will be followed for survival status, subsequent antimyeloma therapies, and the occurrence of second primary malignancies every 16 weeks until the end of the study.

Subject Population

The study is conducted with multiple myeloma patients who have previously received 1 to 3 prior line(s) of therapy including a PI and lenalidomide. If a participant has received only 1 prior line of therapy, his or her disease must be lenalidomide refractory. The inclusion and exclusion criteria for enrolling subjects in this study are described below.

Inclusion Criteria

1. ≥18 years of age.
2. Documented multiple myeloma as defined by the criteria below:
  a. Multiple myeloma diagnosis according to the IMWG diagnostic criteria
  b. Measurable disease at screening as defined by any of the following:
    1) Serum M-protein level ≥0.5 g/dL (central laboratory); or
    2) Urine M-protein level ≥200 mg/24 hours (central laboratory); or
    3) Serum immunoglobulin free light chain ≥10 mg/dL (central laboratory) and abnormal serum immunoglobulin kappa lambda free light chain ratio.

NOTE: All attempts should be made to determine eligibility of the participant based on the central laboratory results of screening blood and urine M-protein measurements. In exceptional circumstances and after discussion with and written approval by the sponsor, the local laboratory results of blood and urine M-protein measurements may be used to determine initial eligibility, but only if the results are ≥25% above the thresholds for measurability. In such cases, central laboratory results should still be obtained prior to the start of administration of study treatment in order to establish baseline central laboratory values and confirm the results from the local laboratory.

3. Received 1 to 3 prior line(s) of antimyeloma therapy including a PI and lenalidomide.
  a. Participants who have received only 1 line of prior line of antimyeloma therapy must be lenalidomide refractory (i.e., have demonstrated progressive disease by IMWG criteria during treatment or within 60 days of completion of lenalidomide-containing regimen). Progression on or within 60 days of the last dose of lenalidomide given as maintenance will meet this criterion.

NOTE: Participant must have undergone 1 complete cycle of treatment for each regimen, unless progressive disease was the best response to the regimen.

NOTE: A single line of therapy may consist of 1 or more agents and may include induction, hematopoietic stem cell transplantation, and maintenance therapy. Radiotherapy, bisphosphonate, or a single short course of corticosteroids (no more than the equivalent of dexamethasone 40 mg/day for 4 days) would not be considered prior lines of therapy.

4. Documented evidence of progressive disease based on investigator's determination of response by IMWG criteria on or after their last regimen.
5. Have an ECOG performance status score of 0, 1, or 2 at screening and immediately prior to the start of administration of study treatment.
6. Have clinical laboratory values meeting the following criteria during the Screening Phase and also at start of administration of study treatment:

TABLE 18

Criteria for clinical laboratory values.

| Hematology | |
| --- | --- |
| Hemoglobin | ≥7.5 g/dL (≥4.65 mmol/L; without prior RBC transfusion within 7 days before the laboratory test; recombinant human erythropoietin use is permitted) |
| Platelets | ≥75 × 10$^9$/L in participants in whom <50% of bone marrow nucleated cells are plasma cells and ≥50 × 10$^9$/L in participants in whom ≥50% of bone marrow nucleated cells are plasma cells (without transfusion support or thrombopoietin receptor agonist within 7 days before the laboratory test) |
| Absolute neutrophil count | ≥1.0 × 10$^9$/L (prior growth factor support is permitted but must be without support for 7 days for G-CSF or GM-CSF and for 14 days for pegylated-G-CSF) |

TABLE 18-continued

Criteria for clinical laboratory values.

Chemistry

| | |
|---|---|
| AST and ALT | ≤2.5 × ULN |
| eGFR | ≥30 mL/min based on Modified Diet in Renal Disease Formula calculation or creatine clearance measured by a 24-hour urine collection |
| Total bilirubin | ≤2.0 × ULN; except in participants with congenital bilirubinemia, such as Gilbert syndrome (in which case direct bilirubin ≤1.5 × ULN is required) |
| Serum calcium corrected for albumin | ≤14 mg/dL (≤3.5 mmol/L) or free ionized calcium ≤6.5 mg/dL (≤1.6 mmol/L) |

ALT = alanine aminotransferase;
AST = aspartate aminotransferase;
CrCl = creatinine clearance;
G-CSF = granulocyte colony-stimulating factor;
GM-CSF = granulocyte-macrophage colony-stimulating factor;
RBC = red blood cell;
ULN = upper limit of normal In addition, these laboratory values must be re-evaluated within the 72 hours prior to the first dose and the participant must also meet all criteria. If one or more criteria are not met 72 hours prior to dosing, one repeat of laboratory testing is permitted. If >1 repeat laboratory test is necessary, the sponsor must be consulted prior to dosing.

7. A woman of childbearing potential must have a negative highly sensitive serum pregnancy test at screening and again within 24 hours of the start of study treatment and must agree to further serum or urine pregnancy tests during the study.

8. A woman must be:
   a. Not of childbearing potential, or
   b. Of childbearing potential and
      1) Practicing true abstinence; or
      2) Practicing 2 effective methods of contraception (at least one must be a highly effective method such as tubal ligation, intrauterine device (IUD), hormonal (birth control pills, hormonal patches, injections, etc.)).

NOTE: Participant must agree to continue the above throughout the study and for 90 days after the last dose of study treatment.

NOTE: If a woman becomes of childbearing potential after start of the study the woman must comply with point (b) as described above.

NOTE: An interaction between hormonal contraception and teclistamab has not been formally studied. Therefore, if a woman randomized to Arm A is using hormonal contraceptives, an additional barrier method must be used.

NOTE: Sexual abstinence is considered a highly effective method only if defined as refraining from heterosexual intercourse during the entire period of risk associated with the study treatment. The reliability of sexual abstinence needs to be evaluated in relation to the duration of the study and the preferred and usual lifestyle of the participant.

9. A woman must agree not to donate eggs (ova, oocytes) or freeze for future use, for the purposes of assisted reproduction during the study and for 90 days after receiving the last dose of study treatment.

10. A man must wear a condom (with spermicidal foam/gel/film/cream/suppository) when engaging in any activity that allows for passage of ejaculate to another person during the study and for a minimum of 90 days after receiving the last dose of study treatment. If a female partner is of childbearing potential, she must also be practicing a highly effective method of contraception.

NOTE: If the male participant is vasectomized, he still must wear a condom (with spermicidal foam/gel/film/cream/suppository), but his female partner is not required to use contraception.

11. A male participant must agree not to donate sperm for the purpose of reproduction during the study and for a minimum of 90 days after receiving the last dose of study treatment.

12. Must be willing and able to adhere to the lifestyle restrictions specified in this protocol.

13. Must sign an ICF (or their legally acceptable representative must sign) indicating that the participant understands the purpose of, and procedures required for, the study and is willing to participate in the study.

Exclusion Criteria

Any potential subject who meets any of the following criteria will be excluded from participating in the study:

1. Contraindications or life-threatening allergies, hypersensitivity, or intolerance to any study drug or its excipients (refer to the teclistamab Investigator's Brochure and appropriate package inserts). Additional exclusion criteria pertaining to specific study drugs include:
   a. A participant is not eligible to receive DPd as control therapy if any of the following are present:
      1) Contraindications or life-threatening allergies, hypersensitivity, or intolerance to pomalidomide (intolerance defined as prior therapy discontinued due to any AE related to pomalidomide)
      2) Disease that is considered refractory to pomalidomide per IMWG (progression during treatment or within 60 days of completing treatment with pomalidomide).
   b. A participant is not eligible to receive DVd as control therapy if any of the following are present:
      1) Contraindications or life-threatening allergies, hypersensitivity, or intolerance to bortezomib (intolerance defined as prior therapy discontinued due to any AE related to bortezomib)
      2) Grade 1 peripheral neuropathy with pain or Grade ≥2 peripheral neuropathy as defined by NCI-CTCAE Version 5.0
      3) Disease that is considered refractory to bortezomib per IMWG (progression during treatment or within 60 days of completing treatment with bortezomib)

4) Received a strong CYP3A4 inducer within 5 half-lives prior to randomization
  c. A participant is not eligible for this study if they are refractory to both pomalidomide and bortezomib.
2. Received any prior BCMA-directed therapy.
3. Has disease that is considered refractory to an anti-CD38 monoclonal antibody per IMWG (progression during treatment or within 60 days of completing therapy with an anti-CD38 monoclonal antibody).
4. Received the following prior antimyeloma therapy, in the specified time frame prior to randomization:
  a. Targeted therapy, epigenetic therapy, or treatment with an investigational drug or an invasive investigational medical device within 21 days or ≥5 half-lives, whichever is less
  b. Investigational vaccine within 4 weeks
  c. Monoclonal antibody therapy within 21 days
  d. Cytotoxic therapy within 21 days
  e. PI therapy within 14 days
  f. IMiD agent therapy within 14 days
  g. Radiotherapy within 14 days or focal radiation within 7 days
  h. Gene-modified adoptive cell therapy (e.g., chimeric antigen receptor modified T cells, NK cells) within 3 months.
5. Stem cell transplant:
  a. An allogeneic stem cell transplant within 6 months before randomization. Participants who received an allogeneic transplant must be off all immunosuppressive medications for ≥42 days without signs of graft-versus-host disease before randomization.
  b. An autologous stem cell transplant within 12 weeks before randomization.
6. Received a cumulative dose of corticosteroids equivalent to ≥140 mg of prednisone within 14 days before randomization.
7. Received a live, attenuated vaccine within 4 weeks before randomization.
8. Myelodysplastic syndrome or active malignancies (i.e., progressing or requiring treatment change in the last 24 months) other than relapsed/refractory multiple myeloma. The only allowed exceptions are:
  a. Non-muscle invasive bladder cancer treated within the last 24 months that is considered completely cured
  b. Skin cancer (non-melanoma or melanoma) treated within the last 24 months that is considered completely cured
  c. Noninvasive cervical cancer treated within the last 24 months that is considered completely cured
  d. Localized prostate cancer (NOMO):
    1) With a Gleason score of ≤6, treated within the last 24 months, or untreated and under surveillance
    2) With a Gleason score of 3+4 that has been treated >6 months prior to full study screening and considered to have a very low risk of recurrence, or
    3) History of localized prostate cancer and receiving androgen deprivation therapy and considered to have a very low risk of recurrence.
  e. Breast cancer: adequately treated lobular carcinoma in situ or ductal carcinoma in situ, or history of localized breast cancer and receiving antihormonal agents and considered to have a very low risk of recurrence
  f. Other malignancy that is considered cured with minimal risk of recurrence.
9. Plasma cell leukemia at the time of screening, Waldenstrom's macroglobulinemia, POEMS syndrome (polyneuropathy, organomegaly, endocrinopathy, M-protein, and skin changes), or primary amyloid light chain amyloidosis.
10. CNS involvement or clinical signs of meningeal involvement of multiple myeloma. If either is suspected, negative whole brain MRI and lumbar cytology are required.
11. Stroke or seizure within 6 months prior to signing ICF.
12. Participant is pregnant, breast-feeding, or planning to become pregnant while enrolled in this study or within 90 days after the last dose of study treatment.
13. Participant plans to father a child while enrolled in this study or within 90 days after the last dose of study treatment.
14. Presence of the following cardiac conditions:
  a. New York Heart Association stage III or IV congestive heart failure
  b. Myocardial infarction or coronary artery bypass graft <6 months prior to randomization
  c. History of clinically significant ventricular arrhythmia or unexplained syncope, not believed to be vasovagal in nature or due to dehydration
  d. Uncontrolled cardiac arrhythmia or clinically significant ECG abnormalities
15. Any of the following:
  a. Seropositive for human immunodeficiency virus.
  b. Hepatitis B infection (i.e., HBsAg or HBV-DNA positive). In the event the infection status is unclear, quantitative viral levels are necessary to determine the infection status.
  c. Active hepatitis C infection as measured by positive HCV-RNA testing. Participants with a history of HCV antibody positivity must undergo HCV-RNA testing. If a participant with history of chronic hepatitis C infection (defined as both HCV antibody and HCV-RNA positive) completed antiviral therapy and has undetectable HCV-RNA 12 weeks following the completion of therapy, the participant is eligible for the study.
  d. COPD with a FEV1<50% of predicted normal. Note that FEV1 testing is required for participants with known or suspected of having COPD or asthma and participants must be excluded if FEV1<50% of predicted normal.
  e. Moderate or severe persistent asthma within the past 2 years or uncontrolled asthma of any classification. Note that FEV1 testing is required for participants known or suspected asthma and participants must be excluded if FEV1<50% of predicted normal.
NOTE: Participants who currently have controlled intermittent asthma or controlled mild persistent asthma are allowed to participate in the study.
16. Concurrent medical or psychiatric condition or disease that is likely to interfere with study procedures or results, or that in the opinion of the investigator would constitute a hazard for participating in this study, such as:
  a. Uncontrolled diabetes
  b. Acute diffuse infiltrative pulmonary disease
  c. Evidence of active systemic viral, fungal, or bacterial infection, requiring systemic antimicrobial therapy
  d. Active autoimmune disease or a documented history of autoimmune disease with the exception of vitiligo, type I diabetes, and prior autoimmune thyroiditis that is currently euthyroid based on clinical symptoms and laboratory testing
  e. Disabling psychiatric conditions (e.g., alcohol or drug abuse), severe dementia, or altered mental status
  f. Any other issue that would impair the ability of the participant to receive or tolerate the planned treatment at the investigational site, to understand informed consent or any condition for which, in the opinion of the investigator, participation would not be in the best interest of the participant (e.g., compromise the well-being) or that could prevent, limit, or confound the protocol-specified assessments g. History of non-compliance with recommended medical treatments 17. Major surgery within 2 weeks prior to the start of administration of study treatment, or will not have fully recovered from surgery, or has major surgery planned during the time the participant is expected to be treated in the study or within 2 weeks after administration of the last dose of study treatment.

NOTE: Participants with planned surgical procedures to be conducted under local anesthesia may participate. Kyphoplasty or vertebroplasty are not considered major surgery. If there is a question whether a procedure is considered a major surgery, the investigator must consult with the appropriate sponsor representative and resolve any issues before enrolling a participant in the study.

Study Interventions

Approximately 560 participants will be randomized in a 1:1 ratio to Tec-Dara (Arm A) or investigator's choice of DPd/DVd (Arm B). Study treatment will be administered on 28-day cycles for Tec-Dara (Arm A) and DPd (Arm B). For DVd (Arm B), study treatment will be administered on 21-day cycles for Cycles to 8 and 28-day cycles for Cycles 9+. Participants in Arm A and Arm B will be treated with dosing regimens shown in Table 19.

Randomization will be stratified by investigator's choice of DPd or DVd, stage of screening per ISS (I vs II vs III), prior anti-CD38 monoclonal antibody exposure, and number of prior lines of therapy (1 vs 2 or 3).

Study Assessment

Efficacy Evaluations

Efficacy assessments will occur per IMWG criteria (2016) as defined in the protocol using data from serum, urine, bone marrow, and imaging (if applicable). Responses or progression will be evaluated by investigators, use of a validated algorithm, and by an Independent Review Committee (IRC).

Pharmacokinetic and Immunogenicity Evaluations

Sparse blood samples will be collected for the measurement of serum concentrations of teclistamab (Arm A [Tec-Dara] only) and daratumumab (both treatment arms) for PK analyses. Population PK analysis may be conducted, and the results reported separately. The detection and characterization of anti-drug antibodies to teclistamab and daratumumab will be performed using validated or appropriately qualified assay methods.

Pharmacodynamic and Exploratory Biomarker Evaluations

Peripheral blood and bone marrow aspirate will be collected from participants in both treatment arms. Biomarker assessments will focus on the following objectives: 1) evaluate pharmacodynamic biomarkers indicative of mechanism of action of teclistamab and daratumumab; 2) determine the ability of study treatment to induce and sustain MRD —negativity; 3) investigate biomarkers of response/

TABLE 19

Dosing regimens for the phase 3 study.

| Arm A: Tec-Dara (28-day cycle) | |
|---|---|
| Teclistamab | Cycle 1:<br>Step-up Dose 1 (0.06 mg/kg): Day 2<br>Step-up Dose 2 (0.3 mg/kg): Day 4<br>Treatment Dose (1.5 mg/kg): Days 8, 15, and 22<br>Cycle 2:<br>Treatment Dose (1.5 mg/kg): Days 1, 8, 15, and 22<br>Cycle 3+:<br>Treatment Dose (3 mg/kg): Days 1 and 15<br>Note: Participants receiving 1.5 mg/kg teclistamab weekly treatment beyond Cycle 3 Day 1 should switch to the 3 mg/kg teclistamab SC biweekly dose on Day 1 of the next planned cycle. |
| Daratumumab SC 1800 mg | Cycles 1-2: Days 1, 8, 15, and 22<br>Cycles 3-6: Days 1 and 15<br>Cycle 7+: Day 1 |
| Arm B: Dpd (28-day cycle) | |
| Daratumumab SC 1800 mg | Cycles 1-2: Days 1, 8, 15, and 22<br>Cycles 3-6: Days 1 and 15<br>Cycle 7+: Day 1 |
| Pomalidomide (oral) 4 mg | All cycles: daily on Days 1-21 |
| Dexamethasone (oral/IV) 40 mg (≤75 years of age) or 20 mg weekly (≥75 years of age and BMI <18.5) | All cycles: Days 1, 8, 15, and 22 |
| Arm B: DVd (21-day cycle for 8 cycles: 28-day cycle for Cycle 9+) | |
| Daratumumab SC 1800 mg | Cycles 1-3, Days 1, 8, 15<br>Cycles 4-8: Day 1<br>Cycle 9+: Day 1 |
| Bortezomib (SC) 1.3 mg/m² | Cycles 1-8 only: Days 1, 4, 8, and 11 |
| Dexamethasone (oral/IV) 20 mg | Cycles 1-8 only: Days 1, 2, 4, 5, 8, 9, 11, and 12 |

The teclistamab SC dosing schedule is the RP2D dose, consisting of 2 step-up doses (0.06 and 0.3 mg/kg) followed by a weekly treatment dose of 1.5 mg/kg.

resistance on myeloma cells (e.g., levels of BCMA, CD38, and PD-L1 expression) and on immune cells (e.g., activation/exhaustion markers on T cells); and 4) determine the clinical benefit of study treatment in participants with cytogenetic alterations or other high-risk molecular subtypes.

Safety Evaluations

The safety of teclistamab in combination with daratumumab SC will be assessed by physical examinations, neurologic examinations, ECOG performance status, clinical laboratory tests, vital signs, and AE monitoring. The severity of AEs will be assessed using NCI-CTCAE Version 5.0, except for grading of CRS and ICANS, which will be assessed based on ASTCT guidelines. Concomitant medication use will be recorded.

Statistical Methods

The primary population for efficacy analysis is the Intent-to-Treat (ITT) Population, which will include all randomized participants. The Safety Set consists of all participants randomized who received any study treatment. Stratified log-rank test, Kaplan-Meier methods, and stratified Cox regression with treatment as the sole explanatory variable will be used for analysis of the primary efficacy endpoint of PFS. For binary-type secondary endpoints (e.g., overall response, VGPR or better, CR, and MRD negativity), stratified Cochran Mantel Haenszel tests will be used. For time-to-event secondary endpoints (e.g., OS, PFS2, time to worsening of PROs, and time to next treatment), similar methods to PFS will be adopted. One interim analysis is planned for PFS after 218 PFS events (O'Brien & Fleming type alpha spending). The final analysis for PFS will be performed after 335 PFS events are reported. The end of study is defined by the final OS (overall survival) analysis, which will occur at the earlier of 335 events or 5 years after the last participant is randomized.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

```
                         SEQUENCE LISTING

Sequence total quantity: 69
SEQ ID NO: 1            moltype = AA  length = 184
FEATURE                 Location/Qualifiers
source                  1..184
                        mol_type = protein
                        organism = Homo sapiens
SEQUENCE: 1
MLQMAGQCSQ NEYFDSLLHA CIPCQLRCSS NTPPLTCQRY CNASVTNSVK GTNAILWTCL     60
GLSLIISLAV FVLMFLLRKI NSEPLKDEFK NTGSGLLGMA NIDLEKSRTG DEIILPRGLE    120
YTVEECTCED CIKSKPKVDS DHCFPLPAME EGATILVTTK TNDYCKSLPA ALSATEIEKS    180
ISAR                                                                 184

SEQ ID NO: 2            moltype = AA  length = 207
FEATURE                 Location/Qualifiers
source                  1..207
                        mol_type = protein
                        organism = Homo sapiens
SEQUENCE: 2
MQSGTHWRVL GLCLLSVGVW GQDGNEEMGG ITQTPYKVSI SGTTVILTCP QYPGSEILWQ     60
HNDKNIGGDE DDKNIGSDED HLSLKEFSEL EQSGYYVCYP RGSKPEDANF YLYLRARVCE    120
NCMEMDVMSV ATIVIVDICI TGGLLLLVYY WSKNRKAKAK PVTRGAGAGG RQRGQNKERP    180
PPVPNPDYEP IRKGQRDLYS GLNQRRI                                        207

SEQ ID NO: 3            moltype = AA  length = 104
FEATURE                 Location/Qualifiers
source                  1..104
                        mol_type = protein
                        organism = Homo sapiens
SEQUENCE: 3
DGNEEMGGIT QTPYKVSISG TTVILTCPQY PGSEILWQHN DKNIGGDEDD KNIGSDEDHL     60
SLKEFSELEQ SGYYVCYPRG SKPEDANFYL YLRARVCENC MEMD                     104

SEQ ID NO: 4            moltype = AA  length = 300
FEATURE                 Location/Qualifiers
source                  1..300
                        mol_type = protein
                        organism = Homo sapiens
SEQUENCE: 4
MANCEFSPVS GDKPCCRLSR RAQLCLGVSI LVLILVVVLA VVVPRWRQQW SGPGTTKRFP     60
ETVLARCVKY TEIHPEMRHV DCQSVWDAFK GAFISKHPCN ITEEDYQPLM KLGTQTVPCN    120
KILLWSRIKD LAHQFTQVQR DMFTLEDTLL GYLADDLTWC GEFNTSKINY QSCPDWRKDC    180
SNNPVSVFWK TVSRRFAEAA CDVVHVMLNG SRSKIFDKNS TFGSVEVHNL QPEKVQTLEA    240
WVIHGGREDS RDLCQDPTIK ELESIISKRN IQFSCKNIYR PDKFLQCVKN PEDSSCTSEI    300

SEQ ID NO: 5            moltype = AA  length = 509
FEATURE                 Location/Qualifiers
source                  1..509
                        mol_type = protein
                        organism = Homo sapiens
SEQUENCE: 5
MGVLKFKHIF FRSFVKSSGV SQIVFTFLLI PCCLTLNFRA PPVIPNVPFL WAWNAPSEFC     60
```

```
LGKFDEPLDM SLFSFIGSPR INATGQGVTI FYVDRLGYYP YIDSITGVTV NGGIPQKISL    120
QDHLDKAKKD ITFYMPVDNL GMAVIDWEEW RPTWARNWKP KDVYKNRSIE LVQQQNVQLS    180
LTEATEKAKQ EFEKAGKDFL VETIKLGKLL RPNHLWGYYL FPDCYNHHYK KPGYNGSCFN    240
VEIKRNDDLS WLWNESTALY PSIYLNTQQS PVAATLYVRN RVREAIRVSK IPDAKSPLPV    300
FAYTRIVFTD QVLKFLSQDE LVYTFGETVA LGASGIVIWG TLSIMRSMKS CLLLDNYMET    360
ILNPYIINVT LAAKMCSQVL CQEQGVCIRK NWNSSDYLHL NPDNFAIQLE KGGKFTVRGK    420
PTLEDLEQFS EKFYCSCYST LSCKEKADVK DTDAVDVCIA DGVCIDAFLK PPMETEEPQI    480
FYNASPSTLS ATMFIVSILF LIISSVASL                                      509

SEQ ID NO: 6             moltype = AA   length = 122
FEATURE                  Location/Qualifiers
source                   1..122
                         mol_type = protein
                         organism = Homo sapiens
SEQUENCE: 6
EVQLLESGGG LVQPGGSLRL SCAVSGFTFN SFAMSWVRQA PGKGLEWVSA ISGSGGGTYY     60
ADSVKGRFTI SRDNSKNTLY LQMNSLRAED TAVYFCAKDK ILWFGEPVFD YWGQGTLVTV    120
SS                                                                   122

SEQ ID NO: 7             moltype = AA   length = 107
FEATURE                  Location/Qualifiers
source                   1..107
                         mol_type = protein
                         organism = Homo sapiens
SEQUENCE: 7
EIVLTQSPAT LSLSPGERAT LSCRASQSVS SYLAWYQQKP GQAPRLLIYD ASNRATGIPA     60
RFSGSGSGTD FTLTISSLEP EDFAVYYCQQ RSNWPPTFGQ GTKVEIK                  107

SEQ ID NO: 8             moltype = AA   length = 5
FEATURE                  Location/Qualifiers
source                   1..5
                         mol_type = protein
                         organism = Homo sapiens
SEQUENCE: 8
SFAMS                                                                  5

SEQ ID NO: 9             moltype = AA   length = 17
FEATURE                  Location/Qualifiers
source                   1..17
                         mol_type = protein
                         organism = Homo sapiens
SEQUENCE: 9
AISGSGGGTY YADSVKG                                                    17

SEQ ID NO: 10            moltype = AA   length = 13
FEATURE                  Location/Qualifiers
source                   1..13
                         mol_type = protein
                         organism = Homo sapiens
SEQUENCE: 10
DKILWFGEPV FDY                                                        13

SEQ ID NO: 11            moltype = AA   length = 11
FEATURE                  Location/Qualifiers
source                   1..11
                         mol_type = protein
                         organism = Homo sapiens
SEQUENCE: 11
RASQSVSSYL A                                                          11

SEQ ID NO: 12            moltype = AA   length = 7
FEATURE                  Location/Qualifiers
source                   1..7
                         mol_type = protein
                         organism = Homo sapiens
SEQUENCE: 12
DASNRAT                                                                7

SEQ ID NO: 13            moltype = AA   length = 9
FEATURE                  Location/Qualifiers
source                   1..9
                         mol_type = protein
                         organism = Homo sapiens
SEQUENCE: 13
QQRSNWPPT                                                              9

SEQ ID NO: 14            moltype = AA   length = 452
FEATURE                  Location/Qualifiers
source                   1..452
```

```
                          mol_type = protein
                          organism = Homo sapiens
SEQUENCE: 14
EVQLLESGGG LVQPGGSLRL SCAVSGFTFN SFAMSWVRQA PGKGLEWVSA ISGSGGGTYY      60
ADSVKGRFTI SRDNSKNTLY LQMNSLRAED TAVYFCAKDK ILWFGEPVFD YWGQGTLVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKRV EPKSCDKTHT CPPCPAPELL     240
GGPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
EEMTKNQVSL TCLVKGFYPS DIAVEWESNG QPENNYKTTP PVLDSDGSFF LYSKLTVDKS     420
RWQQGNVFSC SVMHEALHNH YTQKSLSLSP GK                                   452

SEQ ID NO: 15             moltype = AA  length = 214
FEATURE                   Location/Qualifiers
source                    1..214
                          mol_type = protein
                          organism = Homo sapiens
SEQUENCE: 15
EIVLTQSPAT LSLSPGERAT LSCRASQSVS SYLAWYQQKP GQAPRLLIYD ASNRATGIPA      60
RFSGSGSGTD FTLTISSLEP EDFAVYYCQQ RSNWPPTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 16             moltype = AA  length = 330
FEATURE                   Location/Qualifiers
source                    1..330
                          mol_type = protein
                          organism = Homo sapiens
SEQUENCE: 16
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPELLGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPGK                                      330

SEQ ID NO: 17             moltype = AA  length = 327
FEATURE                   Location/Qualifiers
source                    1..327
                          mol_type = protein
                          organism = Homo sapiens
SEQUENCE: 17
ASTKGPSVFP LAPCSRSTSE STAALGCLVK DYFPEPVTVS WNSGALTSGV HTFPAVLQSS      60
GLYSLSSVVT VPSSSLGTKT YTCNVDHKPS NTKVDKRVES KYGPPCPSCP APEFLGGPSV     120
FLFPPKPKDT LMISRTPEVT CVVVDVSQED PEVQFNWYVD GVEVHNAKTK PREEQFNSTY     180
RVVSVLTVLH QDWLNGKEYK CKVSNKGLPS SIEKTISKAK GQPREPQVYT LPPSQEEMTK     240
NQVSLTCLVK GFYPSDIAVE WESNGQPENN YKTTPPVLDS DGSFFLYSRL TVDKSRWQEG     300
NVFSCSVMHE ALHNHYTQKS LSLSLGK                                         327

SEQ ID NO: 18             moltype = AA  length = 7
FEATURE                   Location/Qualifiers
source                    1..7
                          mol_type = protein
                          organism = Homo sapiens
SEQUENCE: 18
SGSYFWG                                                                 7

SEQ ID NO: 19             moltype = AA  length = 16
FEATURE                   Location/Qualifiers
source                    1..16
                          mol_type = protein
                          organism = Homo sapiens
SEQUENCE: 19
SIYYSGITYY NPSLKS                                                      16

SEQ ID NO: 20             moltype = AA  length = 11
FEATURE                   Location/Qualifiers
source                    1..11
                          mol_type = protein
                          organism = Homo sapiens
SEQUENCE: 20
HDGAVAGLFD Y                                                           11

SEQ ID NO: 21             moltype = AA  length = 11
FEATURE                   Location/Qualifiers
source                    1..11
                          mol_type = protein
                          organism = Homo sapiens
SEQUENCE: 21
```

```
GGNNIGSKSV H                                                                  11

SEQ ID NO: 22            moltype = AA   length = 7
FEATURE                  Location/Qualifiers
source                   1..7
                         mol_type = protein
                         organism = Homo sapiens
SEQUENCE: 22
DDSDRPS                                                                        7

SEQ ID NO: 23            moltype = AA   length = 11
FEATURE                  Location/Qualifiers
source                   1..11
                         mol_type = protein
                         organism = Homo sapiens
SEQUENCE: 23
QVWDSSSDHV V                                                                  11

SEQ ID NO: 24            moltype = AA   length = 121
FEATURE                  Location/Qualifiers
source                   1..121
                         mol_type = protein
                         organism = Homo sapiens
SEQUENCE: 24
QLQLQESGPG LVKPSETLSL TCTVSGGSIS SGSYFWGWIR QPPGKGLEWI GSIYYSGITY              60
YNPSLKSRVT ISVDTSKNQF SLKLSSVTAA DTAVYYCARH DGAVAGLFDY WGQGTLVTVS             120
S                                                                            121

SEQ ID NO: 25            moltype = AA   length = 111
FEATURE                  Location/Qualifiers
source                   1..111
                         mol_type = protein
                         organism = Homo sapiens
SEQUENCE: 25
SYVLTQPPSV SVAPGQTARI TCGGNNIGSK SVHWYQQPPG QAPVVVVYDD SDRPSGIPER              60
FSGSNSGNTA TLTISRVEAG DEAVYYCQVW DSSSDHVVFG GGTKLTVLGQ P                      111

SEQ ID NO: 26            moltype = AA   length = 448
FEATURE                  Location/Qualifiers
source                   1..448
                         mol_type = protein
                         organism = Homo sapiens
SEQUENCE: 26
QLQLQESGPG LVKPSETLSL TCTVSGGSIS SGSYFWGWIR QPPGKGLEWI GSIYYSGITY              60
YNPSLKSRVT ISVDTSKNQF SLKLSSVTAA DTAVYYCARH DGAVAGLFDY WGQGTLVTVS             120
SASTKGPSVF PLAPCSRSTS ESTAALGCLV KDYFPEPVTV SWNSGALTSG VHTFPAVLQS             180
SGLYSLSSVV TVPSSSLGTK TYTCNVDHKP SNTKVDKRVE SKYGPPCPPC PAPEAAGGPS             240
VFLFPPKPKD TLMISRTPEV TCVVVDVSQE DPEVQFNWYV DGVEVHNAKT KPREEQFNST             300
YRVVSVLTVL HQDWLNGKEY KCKVSNKGLP SSIEKTISKA KGQPREPQVY TLPPSQEEMT             360
KNQVSLTCLV KGFYPSDIAV EWESNGQPEN NYKTTPPVLD SDGSFFLYSR LTVDKSRWQE             420
GNVFSCSVMH EALHNHYTQK SLSLSLGK                                                448

SEQ ID NO: 27            moltype = AA   length = 214
FEATURE                  Location/Qualifiers
source                   1..214
                         mol_type = protein
                         organism = Homo sapiens
SEQUENCE: 27
SYVLTQPPSV SVAPGQTARI TCGGNNIGSK SVHWYQQPPG QAPVVVVYDD SDRPSGIPER              60
FSGSNSGNTA TLTISRVEAG DEAVYYCQVW DSSSDHVVFG GGTKLTVLGQ PKAAPSVTLF             120
PPSSEELQAN KATLVCLISD FYPGAVTVAW KGDSSPVKAG VETTTPSKQS NNKYAASSYL             180
SLTPEQWKSH RSYSCQVTHE GSTVEKTVAP TECS                                         214

SEQ ID NO: 28            moltype = AA   length = 5
FEATURE                  Location/Qualifiers
source                   1..5
                         mol_type = protein
                         organism = Homo sapiens
SEQUENCE: 28
TYAMN                                                                          5

SEQ ID NO: 29            moltype = AA   length = 19
FEATURE                  Location/Qualifiers
source                   1..19
                         mol_type = protein
                         organism = Homo sapiens
SEQUENCE: 29
RIRSKYNNYA TYYAASVKG                                                          19
```

```
SEQ ID NO: 30             moltype = AA   length = 14
FEATURE                   Location/Qualifiers
source                    1..14
                          mol_type = protein
                          organism = Homo sapiens
SEQUENCE: 30
HGNFGNSYVS WFAY                                                          14

SEQ ID NO: 31             moltype = AA   length = 14
FEATURE                   Location/Qualifiers
source                    1..14
                          mol_type = protein
                          organism = Homo sapiens
SEQUENCE: 31
RSSTGAVTTS NYAN                                                          14

SEQ ID NO: 32             moltype = AA   length = 7
FEATURE                   Location/Qualifiers
source                    1..7
                          mol_type = protein
                          organism = Homo sapiens
SEQUENCE: 32
GTNKRAP                                                                   7

SEQ ID NO: 33             moltype = AA   length = 9
FEATURE                   Location/Qualifiers
source                    1..9
                          mol_type = protein
                          organism = Homo sapiens
SEQUENCE: 33
ALWYSNLWV                                                                 9

SEQ ID NO: 34             moltype = AA   length = 125
FEATURE                   Location/Qualifiers
source                    1..125
                          mol_type = protein
                          organism = Homo sapiens
SEQUENCE: 34
EVQLVESGGG LVQPGGSLRL SCAASGFTFN TYAMNWVRQA PGKGLEWVAR IRSKYNNYAT         60
YYAASVKGRF TISRDDSKNS LYLQMNSLKT EDTAVYYCAR HGNFGNSYVS WFAYWGQGTL        120
VTVSS                                                                   125

SEQ ID NO: 35             moltype = AA   length = 112
FEATURE                   Location/Qualifiers
source                    1..112
                          mol_type = protein
                          organism = Homo sapiens
SEQUENCE: 35
QTVVTQEPSL TVSPGGTVTL TCRSSTGAVT TSNYANWVQQ KPGQAPRGLI GGTNKRAPGT         60
PARFSGSLLG GKAALTLSGV QPEDEAEYYC ALWYSNLWVF GGGTKLTVLG QP               112

SEQ ID NO: 36             moltype = AA   length = 452
FEATURE                   Location/Qualifiers
source                    1..452
                          mol_type = protein
                          organism = Homo sapiens
SEQUENCE: 36
EVQLVESGGG LVQPGGSLRL SCAASGFTFN TYAMNWVRQA PGKGLEWVAR IRSKYNNYAT         60
YYAASVKGRF TISRDDSKNS LYLQMNSLKT EDTAVYYCAR HGNFGNSYVS WFAYWGQGTL        120
VTVSSASTKG PSVFPLAPCS RSTSESTAAL GCLVKDYFPE PVTVSWNSGA LTSGVHTFPA        180
VLQSSGLYSL SSVVTVPSSS LGTKTYTCNV DHKPSNTKVD KRVESKYGPP CPPCPAPEAA        240
GGPSVFLFPP KPKDTLMISR TPEVTCVVVD VSQEDPEVQF NWYVDGVEVH NAKTKPREEQ        300
FNSTYRVVSV LTVLHQDWLN GKEYKCKVSN KGLPSSIEKT ISKAKGQPRE PQVYTLPPSQ        360
EEMTKNQVSL TCLVKGFYPS DIAVEWESNG QPENNYKTTP PVLDSDGSFL LYSKLTVDKS        420
RWQEGNVFSC SVMHEALHNH YTQKSLSLSL GK                                     452

SEQ ID NO: 37             moltype = AA   length = 215
FEATURE                   Location/Qualifiers
source                    1..215
                          mol_type = protein
                          organism = Homo sapiens
SEQUENCE: 37
QTVVTQEPSL TVSPGGTVTL TCRSSTGAVT TSNYANWVQQ KPGQAPRGLI GGTNKRAPGT         60
PARFSGSLLG GKAALTLSGV QPEDEAEYYC ALWYSNLWVF GGGTKLTVLG QPKAAPSVTL        120
FPPSSEELQA NKATLVCLIS DFYPGAVTVA WKADSSPVKA GVETTTPSKQ SNNKYAASSY        180
LSLTPEQWKS HRSYSCQVTH EGSTVEKTVA PTECS                                  215

SEQ ID NO: 38             moltype = AA   length = 122
FEATURE                   Location/Qualifiers
```

```
source                  1..122
                        mol_type = protein
                        organism = Homo sapiens
SEQUENCE: 38
QVQLVQSGAE VKKPGSSVKV SCKASGGTFS SYAFSWVRQA PGQGLEWMGR VIPFLGIANS        60
AQKFQGRVTI TADKSTSTAY MDLSSLRSED TAVYYCARDD IAALGPFDYW GQGTLVTVSS       120
AS                                                                     122

SEQ ID NO: 39           moltype = AA  length = 107
FEATURE                 Location/Qualifiers
source                  1..107
                        mol_type = protein
                        organism = Homo sapiens
SEQUENCE: 39
DIQMTQSPSS LSASVGDRVT ITCRASQGIS SWLAWYQQKP EKAPKSLIYA ASSLQSGVPS        60
RFSGSGSGTD FTLTISSLQP EDFATYYCQQ YNSYPRTFGQ GTKVEIK                    107

SEQ ID NO: 40           moltype = AA  length = 122
FEATURE                 Location/Qualifiers
source                  1..122
                        mol_type = protein
                        organism = Homo sapiens
SEQUENCE: 40
EVQLVQSGAE VKKPGESLKI SCKGSGYSFS NYWIGWVRQM PGKGLEWMGI IYPHDSDARY        60
SPSFQGQVTF SADKSISTAY LQWSSLKASD TAMYYCARHV GWGSRYWYFD LWGRGTLVTV       120
SS                                                                     122

SEQ ID NO: 41           moltype = AA  length = 107
FEATURE                 Location/Qualifiers
source                  1..107
                        mol_type = protein
                        organism = Homo sapiens
SEQUENCE: 41
EIVLTQSPAT LSLSPGERAT LSCRASQSVS SYLAWYQQKP GQAPGLLIYD ASNRASGIPA        60
RFSGSGSGTD FTLTISSLEP EDFAVYYCQQ RSNWPLTFGG GTKVEIK                    107

SEQ ID NO: 42           moltype = AA  length = 120
FEATURE                 Location/Qualifiers
source                  1..120
                        mol_type = protein
                        organism = Homo sapiens
SEQUENCE: 42
QVQLVESGGG LVQPGGSLRL SCAASGFTFS SYYMNWVRQA PGKGLEWVSG ISGDPSNTYY        60
ADSVKGRFTI SRDNSKNTLY LQMNSLRAED TAVYYCARDL PLVYTGFAYW GQGTLVTVSS       120

SEQ ID NO: 43           moltype = AA  length = 109
FEATURE                 Location/Qualifiers
source                  1..109
                        mol_type = protein
                        organism = Homo sapiens
SEQUENCE: 43
DIELTQPPSV SVAPGQTARI SCSGDNLRHY YVYWYQQKPG QAPVLVIYGD SKRPSGIPER        60
FSGSNSGNTA TLTISGTQAE DEADYYCQTY TGGASLVFGG GTKLTVLGQ                  109

SEQ ID NO: 44           moltype = AA  length = 120
FEATURE                 Location/Qualifiers
source                  1..120
                        mol_type = protein
                        organism = Homo sapiens
SEQUENCE: 44
QVQLVQSGAE VAKPGTSVKL SCKASGYTFT DYWMQWVKQR PGQGLEWIGT IYPGDGDTGY        60
AQKFQGKATL TADKSSKTVY MHLSSLASED SAVYYCARGD YYGSNSLDYW GQGTSVTVSS       120

SEQ ID NO: 45           moltype = AA  length = 107
FEATURE                 Location/Qualifiers
source                  1..107
                        mol_type = protein
                        organism = Homo sapiens
SEQUENCE: 45
DIVMTQSHLS MSTSLGDPVS ITCKASQDVS TVVAWYQQKP GQSPRRLIYS ASYRYIGVPD        60
RFTGSGAGTD FTFTISSVQA EDLAVYYCQQ HYSPPYTFGG GTKLEIK                    107

SEQ ID NO: 46           moltype = AA  length = 7
FEATURE                 Location/Qualifiers
source                  1..7
                        mol_type = protein
                        organism = Homo sapiens
SEQUENCE: 46
GFTFNSF                                                                  7
```

```
SEQ ID NO: 47           moltype = AA  length = 6
FEATURE                 Location/Qualifiers
source                  1..6
                        mol_type = protein
                        organism = Homo sapiens
SEQUENCE: 47
SGSGGG                                                                    6

SEQ ID NO: 48           moltype = AA  length = 10
FEATURE                 Location/Qualifiers
source                  1..10
                        mol_type = protein
                        organism = Homo sapiens
SEQUENCE: 48
GFTFNSFAMS                                                               10

SEQ ID NO: 49           moltype = AA  length = 10
FEATURE                 Location/Qualifiers
source                  1..10
                        mol_type = protein
                        organism = Homo sapiens
SEQUENCE: 49
AISGSGGGTY                                                               10

SEQ ID NO: 50           moltype = AA  length = 8
FEATURE                 Location/Qualifiers
source                  1..8
                        mol_type = protein
                        organism = Homo sapiens
SEQUENCE: 50
GFTFNSFA                                                                  8

SEQ ID NO: 51           moltype = AA  length = 8
FEATURE                 Location/Qualifiers
source                  1..8
                        mol_type = protein
                        organism = Homo sapiens
SEQUENCE: 51
ISGSGGGT                                                                  8

SEQ ID NO: 52           moltype = AA  length = 15
FEATURE                 Location/Qualifiers
source                  1..15
                        mol_type = protein
                        organism = Homo sapiens
SEQUENCE: 52
AKDKILWFGE PVFDY                                                         15

SEQ ID NO: 53           moltype = AA  length = 6
FEATURE                 Location/Qualifiers
source                  1..6
                        mol_type = protein
                        organism = Homo sapiens
SEQUENCE: 53
QSVSSY                                                                    6

SEQ ID NO: 54           moltype = AA  length = 9
FEATURE                 Location/Qualifiers
source                  1..9
                        mol_type = protein
                        organism = Homo sapiens
SEQUENCE: 54
GGSISSGSY                                                                 9

SEQ ID NO: 55           moltype = AA  length = 5
FEATURE                 Location/Qualifiers
source                  1..5
                        mol_type = protein
                        organism = Homo sapiens
SEQUENCE: 55
YYSGI                                                                     5

SEQ ID NO: 56           moltype = AA  length = 7
FEATURE                 Location/Qualifiers
source                  1..7
                        mol_type = protein
                        organism = Homo sapiens
SEQUENCE: 56
```

-continued

```
GFTFNTY                                                              7

SEQ ID NO: 58          moltype = AA   length = 8
FEATURE                Location/Qualifiers
source                 1..8
                       mol_type = protein
                       organism = Homo sapiens SEQUENCE: 57
RSKYNNYA                                                             8

SEQ ID NO: 58          moltype = AA   length = 12
FEATURE                Location/Qualifiers
source                 1..12
                       mol_type = protein
                       organism = Homo sapiens SEQUENCE: 58
GGSISSGSYF WG                                                       12

SEQ ID NO: 59          moltype = AA   length = 9
FEATURE                Location/Qualifiers
source                 1..9
                       mol_type = protein
                       organism = Homo sapiens SEQUENCE: 59
SIYYSGITY                                                            9

SEQ ID NO: 60          moltype = AA   length = 10
FEATURE                Location/Qualifiers
source                 1..10
                       mol_type = protein
                       organism = Homo sapiens SEQUENCE: 60
GFTFNTYAMN                                                          10

SEQ ID NO: 61          moltype = AA   length = 12
FEATURE                Location/Qualifiers
source                 1..12
                       mol_type = protein
                       organism = Homo sapiens SEQUENCE: 61
RIRSKYNNYA TY                                                       12

SEQ ID NO: 62          moltype = AA   length = 10
FEATURE                Location/Qualifiers
source                 1..10
                       mol_type = protein
                       organism = Homo sapiens SEQUENCE: 62
GGSISSGSYF                                                          10

SEQ ID NO: 63          moltype = AA   length = 7
FEATURE                Location/Qualifiers
source                 1..7
                       mol_type = protein
                       organism = Homo sapiens SEQUENCE: 63
IYYSGIT                                                              7

SEQ ID NO: 64          moltype = AA   length = 13
FEATURE                Location/Qualifiers
source                 1..13
                       mol_type = protein
                       organism = Homo sapiens SEQUENCE: 64
ARHDGAVAGL FDY                                                      13

SEQ ID NO: 65          moltype = AA   length = 6
FEATURE                Location/Qualifiers
source                 1..6
                       mol_type = protein
                       organism = Homo sapiens SEQUENCE: 65
NIGSKS                                                               6

SEQ ID NO: 66          moltype = AA   length = 8
FEATURE                Location/Qualifiers
source                 1..8
                       mol_type = protein
                       organism = Homo sapiens
```

```
SEQUENCE: 66
GFTFNTYA                                                                              8

SEQ ID NO: 67           moltype = AA   length = 10
FEATURE                 Location/Qualifiers
source                  1..10
                        mol_type = protein
                        organism = Homo sapiens
SEQUENCE: 67
IRSKYNNYAT                                                                           10

SEQ ID NO: 68           moltype = AA   length = 16
FEATURE                 Location/Qualifiers
source                  1..16
                        mol_type = protein
                        organism = Homo sapiens
SEQUENCE: 68
ARHGNFGNSY VSWFAY                                                                    16

SEQ ID NO: 69           moltype = AA   length = 9
FEATURE                 Location/Qualifiers
source                  1..9
                        mol_type = protein
                        organism = Homo sapiens
SEQUENCE: 69
TGAVTTSNY                                                                             9
```

We claim:

1. A method of treating multiple myeloma in a human subject in need thereof, comprising administering to the subject a BCMAxCD3 bispecific antibody and an anti-CD38 antibody in 28-day treatment cycles, wherein the method comprises:
   subcutaneously administering to the subject the BCMAxCD3 bispecific antibody in step-up doses of 0.06 mg/kg and 0.3 mg/kg followed by a dose of 1.5 mg/kg once per week during treatment cycle 1, a dose of 1.5 mg/kg once per week during treatment cycle 2, and a dose of 3 mg/kg once every two weeks beginning in treatment cycle 3, and
   subcutaneously administering to the subject the anti-CD38 antibody at a dose of 1800 mg once per week during treatment cycles 1 and 2, once every two weeks during treatment cycles 3-6 and once every 4 weeks beginning in treatment cycle 7,
   wherein the BCMAxCD3 bispecific antibody comprises:
   (1) a BCMA binding domain comprising a heavy chain variable region (VH) having heavy chain complementarity determining regions (HCDRs) HCDR1, HCDR2 and HCDR3 of the amino acid sequences of SEQ ID NO: 18, SEQ ID NO: 19, and SEQ ID NO: 20, respectively, and a light chain variable region (VL) having light chain complementarity determining regions (LCDRs) LCDR1, LCDR2 and LCDR3 of the amino acid sequences of SEQ ID NO: 21, SEQ ID NO: 22, and SEQ ID NO: 23, respectively, and
   (2) a CD3 binding domain comprising a VH having HCDR1, HCDR2 and HCDR3 of the amino acid sequences of SEQ ID NO: 28, SEQ ID NO: 29, and SEQ ID NO: 30, respectively, and a VL having LCDR1, LCDR2 and LCDR3 of the amino acid sequences of SEQ ID NO: 31, SEQ ID NO: 32, and SEQ ID NO: 33, respectively,
   wherein the method is effective in treating the multiple myeloma.

2. The method of claim 1, wherein the anti-CD38 antibody is administered or provided for administration together with rHuPH20.

3. The method of claim 2, wherein rHuPH20 is administered or provided for administration at a dose of about 30,000 U.

4. The method of claim 1, wherein the BCMA binding domain comprises the VH having the amino acid sequence of SEQ ID NO: 24 and the VL having the amino acid sequence of SEQ ID NO: 25; the CD3 binding domain comprises the VH having the amino acid sequence of SEQ ID NO: 34 and the VL having the amino acid sequence of SEQ ID NO: 35.

5. The method of claim 1, wherein the BCMAxCD3 bispecific antibody comprises a first heavy chain (HC1) having the amino acid sequence of SEQ ID NO: 26, a first light chain (LC1) having the amino acid sequence of SEQ ID NO: 27, a second heavy chain (HC2) having the amino acid sequence of SEQ ID NO: 36, and a second light chain (LC2) having the amino acid sequence of SEQ ID NO: 37.

6. The method of claim 1, wherein the anti-CD38 antibody comprises a VH having HCDR1, HCDR2 and HCDR3 of the amino acid sequences of SEQ ID NO: 8, SEQ ID NO: 9, and SEQ ID NO: 10, respectively, and a VL having LCDR1, LCDR2 and LCDR3 of the amino acid sequences of SEQ ID NO: 11, SEQ ID NO: 12, and SEQ ID NO: 13, respectively.

7. The method of claim 6, wherein the CD38 antibody comprises the VH having the amino acid sequence of SEQ ID NO: 6, and the VL having the amino acid sequence of SEQ ID NO: 7.

8. The method of claim 1 comprising administering the BCMAxCD3 bispecific antibody once every 4 weeks beginning in treatment cycle 7.

9. The method of claim 1, wherein the subject is relapsed or refractory to at least one prior treatment for multiple myeloma, wherein the at least one prior treatment comprises at least one of a proteasome inhibitor (PI) or an immunomodulatory agent (IMiD).

10. The method of claim 9, wherein the subject is refractory or relapsed to treatment with a proteasome inhibitor (PI) and lenalidomide.

* * * * *